United States Patent [19]
Deninno

[11] Patent Number: 5,939,398
[45] Date of Patent: Aug. 17, 1999

[54] HYPOCHOLESTEROLEMIC AGENTS

[75] Inventor: Michael Paul Deninno, Gales Ferry, Conn.

[73] Assignee: Pfizer Inc., New York, N.Y.

[21] Appl. No.: 09/009,037

[22] Filed: Jan. 20, 1998

Related U.S. Application Data

[63] Continuation of application No. 08/652,478, Jun. 18, 1996, filed as application No. PCT/IB94/00348, Nov. 10, 1994, abandoned, which is a continuation of application No. 08/174,099, Dec. 28, 1993, abandoned.

[51] Int. Cl.$^6$ .......................... A61K 31/705; C07J 71/00

[52] U.S. Cl. .................................. 514/26; 540/19; 540/20

[58] Field of Search ........................... 540/19, 20; 514/26

[56] References Cited

U.S. PATENT DOCUMENTS

| 4,602,003 | 7/1986 | Malinow | 514/26 |
| 5,629,295 | 5/1997 | Deninno et al. | 514/26 |
| 5,807,834 | 9/1998 | Morehouse | 514/26 |

FOREIGN PATENT DOCUMENTS

93/11150  6/1993  WIPO .

*Primary Examiner*—José G. Dees
*Assistant Examiner*—Barbara Badio
*Attorney, Agent, or Firm*—Peter C. Richardson; Gregg C. Benson; A. Dean Olson

[57] ABSTRACT

This invention relates to certain steroidal glycosides useful as hypocholesterolemic agents and antiatherosclerosis agents and certain protected intermediates useful in the preparation of said steroidal glycosides.

23 Claims, No Drawings

HYPOCHOLESTEROLEMIC AGENTS

This is a continuation of U.S. application Ser. No. 08/652,478 which was filed on Jun. 18, 1996, now abandoned, which was filed under 35 U.S.C. §371, based on PCT/ID94/00348, which was filed on Nov. 10, 1994 which is a continuation of U.S. application Ser. No. 08/174,099, which was filed on Dec. 28, 1993 and is now abandoned.

BACKGROUND OF THE INVENTION

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficiency. Thus, the effective hypocholesterolemic dose of these materials is excessive, typically 18–24 grams of formulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of non-useful chemical substances. Due to the variations in composition, it is difficult to set a standard dosage or predict the impurities present. Thus, such extracts are not well suited for use by humans. Furthermore purification of these extracts would be expensive. As an alternative certain synthetically produced, pure "sapogenin-derived" compounds e.g., substances compounded from spirostane, spirostene or sterol-derived compounds depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive amounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, Iu. K. Vasilenko, G. M. Gorianu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyramine. PCT publication WO 93/07167 discloses several steroidal glycosides in particular 3-O-(5-C-hydroxymethyl-L-arabino-hexopyranosyl)-tigogenin and 3-O-(5-C-hydroxymethyl-L-arabino-hexopyranosyl)-diosgenin and their use in the control of hypercholesterolemia.

Recently commonly assigned PCT publication WO 93/11150 has disclosed a number of steroidal glycosides including 11-ketotigogenyl-beta-O-cellobioside, hecogenin-beta-O-cellobioside, diosgenin-beta-O-cellobioside and their use as antihypercholesterolemic agents. Also commonly assigned PCT publication WO 94/00480, the disclosure of which is hereby incorporated by reference, discloses a variety of steroidal glycosides and their use as antihypercholesterolemic agents.

Although the hypocholesterolemic compounds described above make a significant contribution to the art there is a continuing search in this field of art for improved hypocholesterolemic pharmaceuticals.

SUMMARY OF THE INVENTION

This invention is directed to steroidal glycosides, particularly spirostanyl glycosides, that are useful as hypocholesterolemic agents and antiatherosclerosis agents. The compounds of this invention have the formula

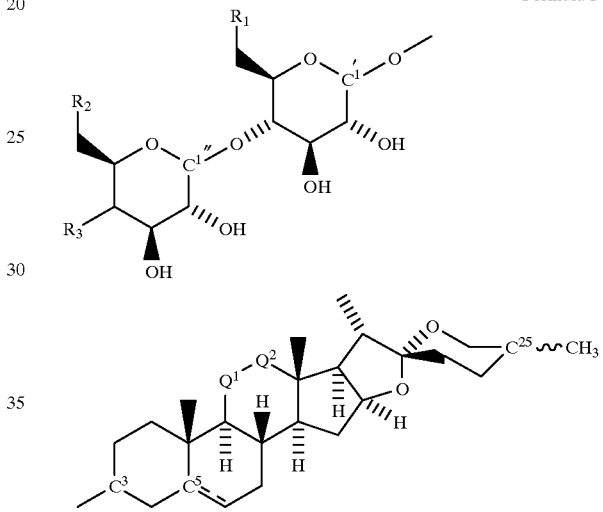

Formula I and the pharmaceutically-acceptable salts and hydrates thereof wherein $Q^1$ is carbonyl,

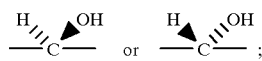

$Q^2$ is methylene, carbonyl,

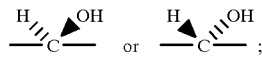

$R_1$, $R_2$, and $R_3$ are each independently hydrogen, hydroxy, halo, amino, azido, $(C_1-C_6)$alkoxy$(C_1-C_6)$alkoxy or —Z—$R_4$;

Z for each occurrence is independently —NH—C(=O)—, —O—C(=O)—, —O—C(=O)—N($R_5$)—, —NH—C(=O)—N($R^5$)— or —O—C(=S)—N($R^5$)—;

$R_4$ for each occurrence is independently aryl, aryl$(C_1-C_6)$alkyl, $(C_2-C_4)$alkenyl, $(C_1-C_6)$alkyl, cyclo$(C_3-C_7)$alkyl or cyclo$(C_3-C_7)$alkyl$(C_1-C_6)$alkyl; each $R_4$ optionally mono-, di-, or tri-substituted independently with halo, $(C_1-C_4)$alkyl, hydroxy, phenoxy, trifluoromethyl, nitro, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, dimethylamino, mono-or di-($C_1$–$C_4$)alkylaminocarbonyl, ($C_1$–$C_4$)alkylcarbonyl, ($C_1$–$C_4$)alkoxycarbonyl, pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and $R_5$ for each occurrence is independently hydrogen, ($C_1$–$C_4$)alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with ($C_1$–$C_4$) alkoxycarbonyl;

with the proviso that $R_1$, $R_2$ and $R_3$ are not all hydroxy.

A first group of preferred compounds of Formula I consists of those compounds wherein $R_1$, $R_2$ and $R_3$ are each independently hydroxy or -Z-$R_4$, Z is —O—C(=O)—N($R_5$)— and $R_5$ is hydrogen. Within this first group of preferred compounds are especially preferred compounds wherein the $C^{1'}$ anomeric oxy is beta, the $C^{1'''}$ anomeric oxy is beta, $R_3$ is alpha, the $C^5$ hydrogen is alpha, $C^{25}$ is (R), the $C^3$ oxy is beta, $Q^1$ is carbonyl, $Q^2$ is methylene and $R_1$ is hydroxy. Particularly preferred compounds within the above group of especially preferred compounds are compounds wherein $R_2$ and $R_3$ are —Z—$R_4$ and $R_4$ is 2-fluorophenyl, 2,4-difluorophenyl, 2-methylphenyl, 2-thienyl-methyl, 2-methoxycarbonyl-ethyl, thiazol-2-yl-methyl, 2-methoxycarbonyl-butyl or phenyl. Other particularly preferred compounds within the above group of especially preferred compounds are compounds wherein $R_2$ is -Z-$R_4$, $R_3$ is hydroxy and $R_4$ is 2,4-difluorophenyl, 2,6-dichlorophenyl or 2-fluorophenyl.

Other especially preferred compounds within the above first group of preferred compounds of Formula I are compounds wherein the $C^{1'}$ anomeric oxy is beta, the $C^{1'''}$ anomeric oxy is beta, $R_3$ is alpha, the $C^5$ hydrogen is alpha, $C^{25}$ is (R), the $C^3$ oxy is beta, $Q^1$ is carbonyl, $Q^2$ is

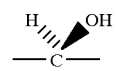

and $R_1$ is hydroxy. Particularly preferred compounds within this group are compounds wherein $R_2$ and $R_3$ are Z—$R_4$ and $R_4$ is 2-fluorophenyl, 2-thienyl-methyl, 2-methoxycarbonyl-ethyl or thiazol-2-yl-methyl.

A second group of preferred compounds of Formula I consists of those compounds wherein $Q^1$ is carbonyl, $R_1$ is hydroxy, hydrogen, halo, azido, or ($C_1$–$C_6$)alkoxy($C_1$–$C_6$) alkoxy, $R_2$ is hydrogen, halo, azido, or ($C_1$–$C_6$)alkoxy ($C_1$–$C_6$)alkoxy, $R_3$ is Z—$R_4$, Z is —O—C(=O)N($R_5$)— and $R_5$ is hydrogen. Within this second group of preferred compounds are especially preferred compounds wherein the $C^1$ anomeric oxy is beta, the $C^1$ anomeric oxy is beta, $R_3$ is alpha, the $C^5$ hydrogen Is alpha, $C^{25}$ is (R) and the $C^3$ oxy is beta. Particularly preferred compounds within the above group of especially preferred compounds are compounds wherein $R_1$ is hydroxy, $R_2$ is hydrogen and $R_4$ is 2-fluorophenyl.

A third group of preferred compounds of Formula I consists of those compounds wherein $R_1$, $R_2$ and $R_3$ are each independently hydroxy or —Z—$R_4$, Z is —O—C(=O)—, $R_4$ is independently ($C_1$–$C_6$)alkyl, aryl or aryl mono- or disubstituted with halo or ($C_1$–$C_6$)alkyl. Within this third group of preferred compounds are especially preferred compounds wherein $R_1$ and $R_2$ are —Z—$R_4$, $R_3$ is alpha hydroxy, $R_4$ is 2-furyl, the $C^{1'}$ anomeric oxy is beta, the $C^{1'''}$ anomeric oxy is beta, the $C^5$ hydrogen is alpha, $C^{25}$ is (R), the $C^3$ oxy is beta, $Q^1$ is carbonyl and $Q^2$ is methylene.

A fourth group of preferred compounds of Formula I consists of those compounds wherein $R_1$, $R_2$ and $R_3$ are each independently hydroxy or halo, $Q^1$ is carbonyl, the $C^{1'''}$ anomeric oxy is beta and $R_3$ is alpha.

Protected intermediates of the above Formula I compounds include compounds of Formula IIA Formula IIA

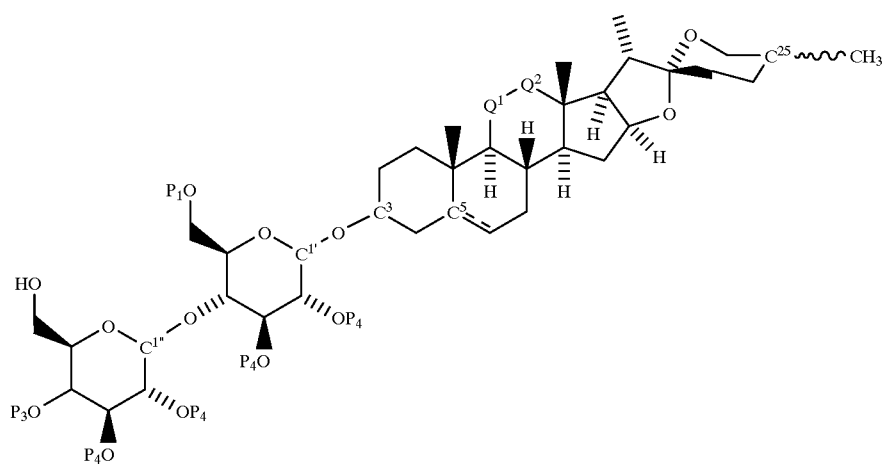

wherein wherein
Q¹ is carbonyl,

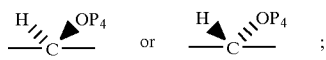

Q² is methylene, carbonyl,

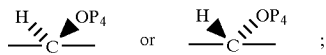

$P_4$ is an alcohol protecting group; and
$P_1$ is hydrogen and $P_3$ is an alcohol protecting group or $P_3$ is hydrogen and $P_1$ is an alcohol protecting group.

Preferred compounds of Formula IIA consists of these compounds wherein the alcohol protecting group is acetyl or chloroacetyl. Other protected intermediates of the above Formula I compounds include compounds of Formula IIB wherein
Q¹ is carbonyl,

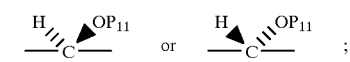

Q² is methylene, carbonyl,

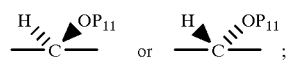

$P_{10}$ is a silyl protecting group; and
$P_{11}$ is an alcohol protecting group that is different from $P_{10}$.

Preferred compounds of Formula IIB consist of these compounds wherein the alcohol protecting group is acetyl and the silyl protecting group is t-butyldiphenylsilyl, triisopropylsilyl or t-butyldimethylsilyl.

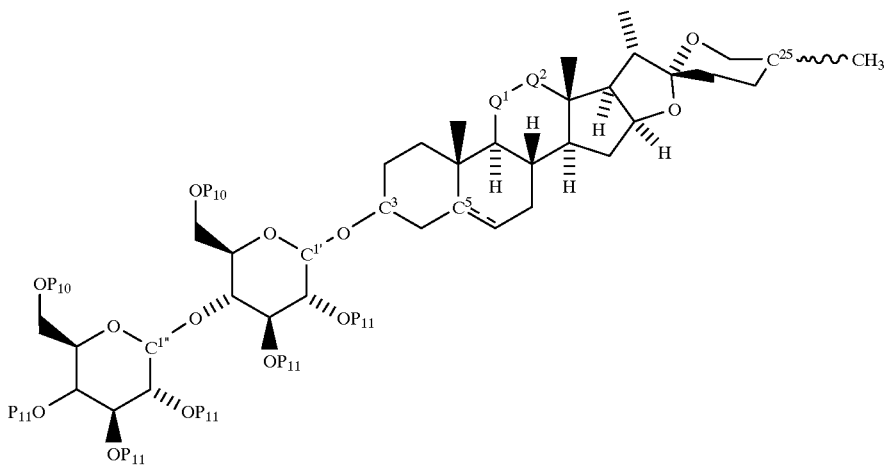

Formula IIB

Yet still other protected intermediates of the above Formula I compounds include compounds of Formula IIC

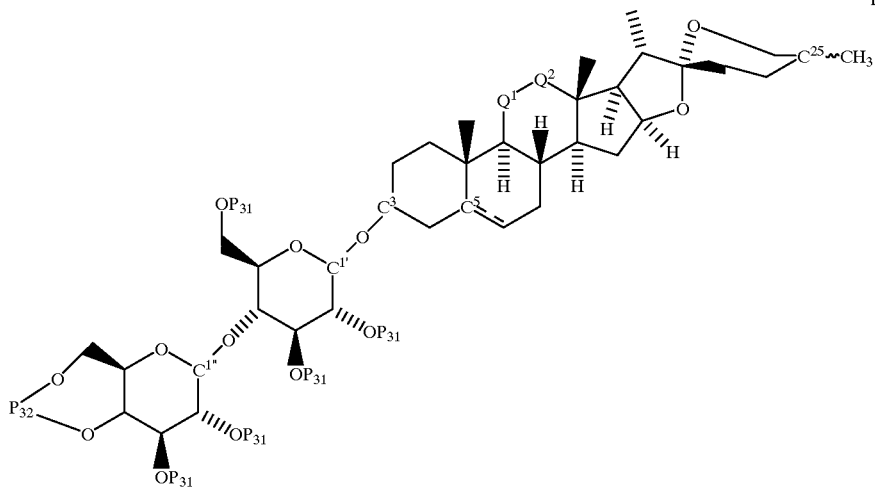

Formula IIC wherein

Q¹ is carbonyl,

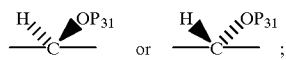

Q² is methylene, carbonyl,

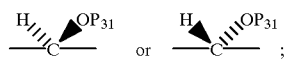

P$_{31}$ is an alcohol protecting group; and
P$_{32}$ forms a cyclic protecting group for a 1,3 diol.

Preferred compounds of Formula IIC consists of these compounds wherein P$_{31}$ is acetyl or chloroacetyl and P$_{32}$ is benzylidene or paramethoxybenzylidene.

Yet another aspect of this invention is directed to a method for treating hypercholesterolemia or atherosclerosis in a mammal by administering to a mammal suffering from hypercholesterolemia or atherosclerosis a hypercholesterolemia or atherosclerosis treating amount of a Formula I compound.

This invention is also directed to pharmaceutical compositions for the treatment of hypercholesterolemia or atherosclerosis in mammals which comprise a therapeutically effective amount of a compound of the Formula I and a pharmaceutically acceptable carrier.

The compounds of Formula I are herein defined as the single enantiomer having the absolute stereochemistry depicted in Formula I.

By alcohol protecting group is meant a conventional alcohol protecting group known to those skilled in the art. Such alcohol protecting groups are described in T. W. Greene, *Protective Groups in Organic Synthesis*, John Wiley & Sons, New York, New York, 1991, 2nd Edition, which is hereby incorporated by reference (e.g., see pages 10–13) and include for example, esters such as formyl, (C$_1$–C$_{10}$)alkanoyl optionally mono-, di- or tri-substituted with (C$_1$–C$_6$)alkoxy, halo, aryl, aryloxy or haloaryloxy; aroyl optionally mono-, di- or tri-substituted on carbon with halo, (C$_1$–C$_6$)alkyl, (C$_1$–C$_6$)alkoxy wherein aryl is phenyl, 2-furyl etc; carbonates; sulfonates; and ethers such as benzyl, paramethoxybenzyl, methoxymethyl etc.

By silyl protecting group is meant a conventional trisubstituted silyl protecting group known to those skilled in the art such as is used to protect a hydroxy group (not to protect a silyl group). Such silyl protecting groups are described in the above cited T. W. Greene book (e.g., page 12) and include for example, silyl compounds where each of the three silyl subtituents may be (C$_1$–C$_6$)alkyl optionally substituted with (C$_1$–C$_6$)alkoxy, halo or aryl; and aryl optionally substituted on carbon with halo, (C$_1$–C$_6$)alkyl, (C$_1$–C$_6$)alkoxy wherein aryl is phenyl, 2-furyl etc.

By forms a cyclic protecting group for a 1,3 diol is meant a conventional ketal or acetal protecting group known to those skilled in the art. Such cyclic protecting groups are described in the above cited T. W. Greene book (e.g., page 13 and 14) and include for example, wherein the protecting group is cyclic acetal, (C$_1$–C$_6$)alkylidene optionally substituted with (C$_1$–C$_6$)alkoxy or halo; and arylidene optionally substituted on carbon with halo, (C$_1$–C$_6$)alkyl, (C$_1$–C$_6$)alkoxy wherein arylidene is phenylidene, 2-furylidene etc. and their cyclic ketal analogs wherein the additional substitutent is (C$_1$–C$_6$)alkyl optionally substituted with (C$_1$–C$_6$)alkoxy or halo or aryl optionally substituted on carbon with halo, (C$_1$–C$_6$)alkyl or (C$_1$–C$_6$)alkoxy wherein aryl is phenyl, 2-furyl etc.

By halo is meant chloro, bromo, iodo, or fluoro.

By alkyl is meant straight chain or branched saturated hydrocarbon.

This invention describes steroidal glycosides in which the sugars are substituted (e.g., with carbamoyl, thiocarbamoyl acyl and silyl groups). In the nomenclature (see Examples and Preparations) all such groups are herein defined as substituted on oxygen unless otherwise designated as deoxy.

The Z moities described above are herein defined such that they are to be read from left to right (i.e., the left or first atom is attached to the sugar molecule and not to R$_4$).

The C$^5$–C$^6$ dotted line in the above steroidal moiety is herein defined as an optional carbon—carbon double bond.

Other features and advantages will be apparent from the specification and claims which describe the invention.

DETAILED DESCRIPTION OF THE INVENTION
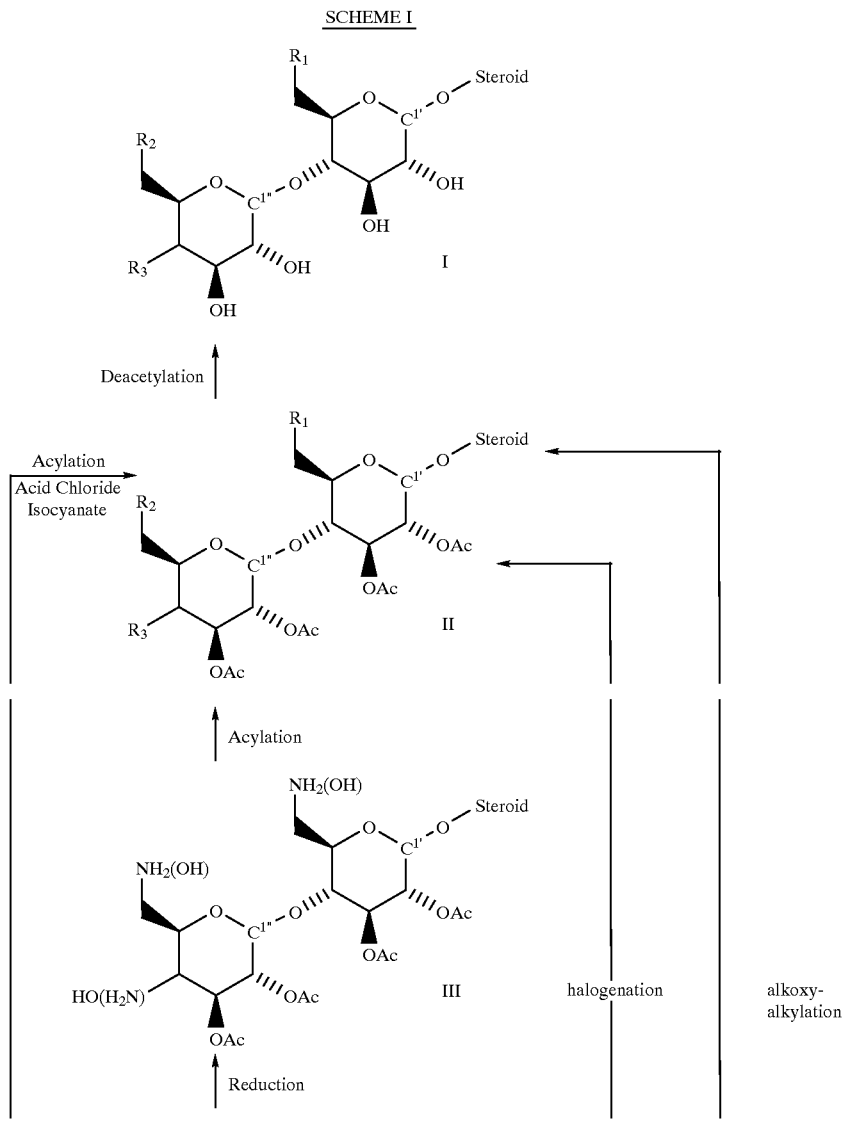

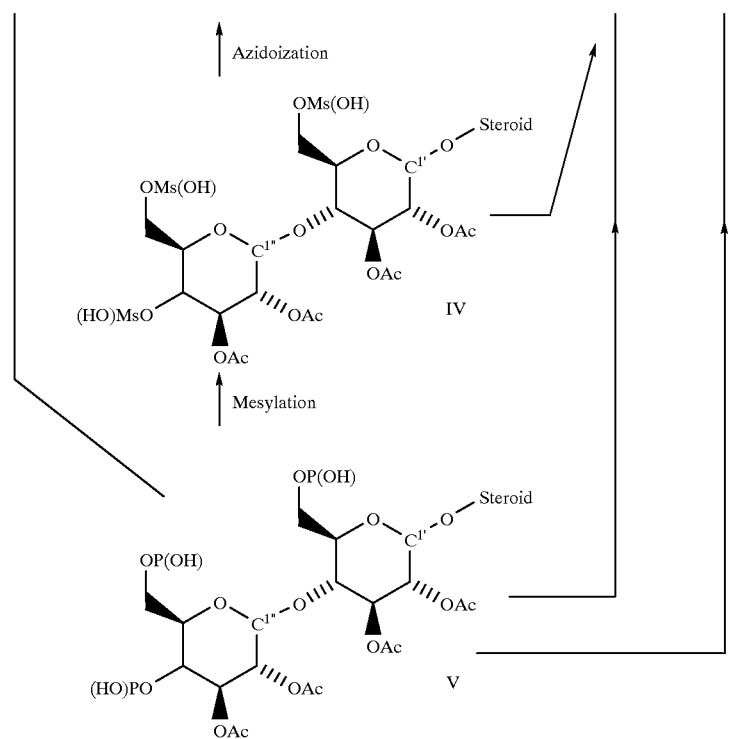
SCHEME II
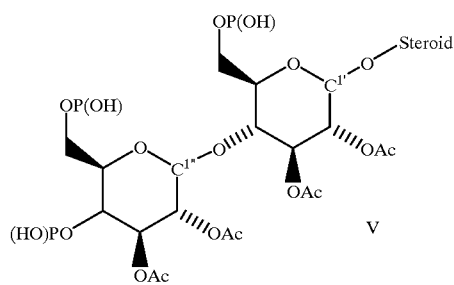

-continued
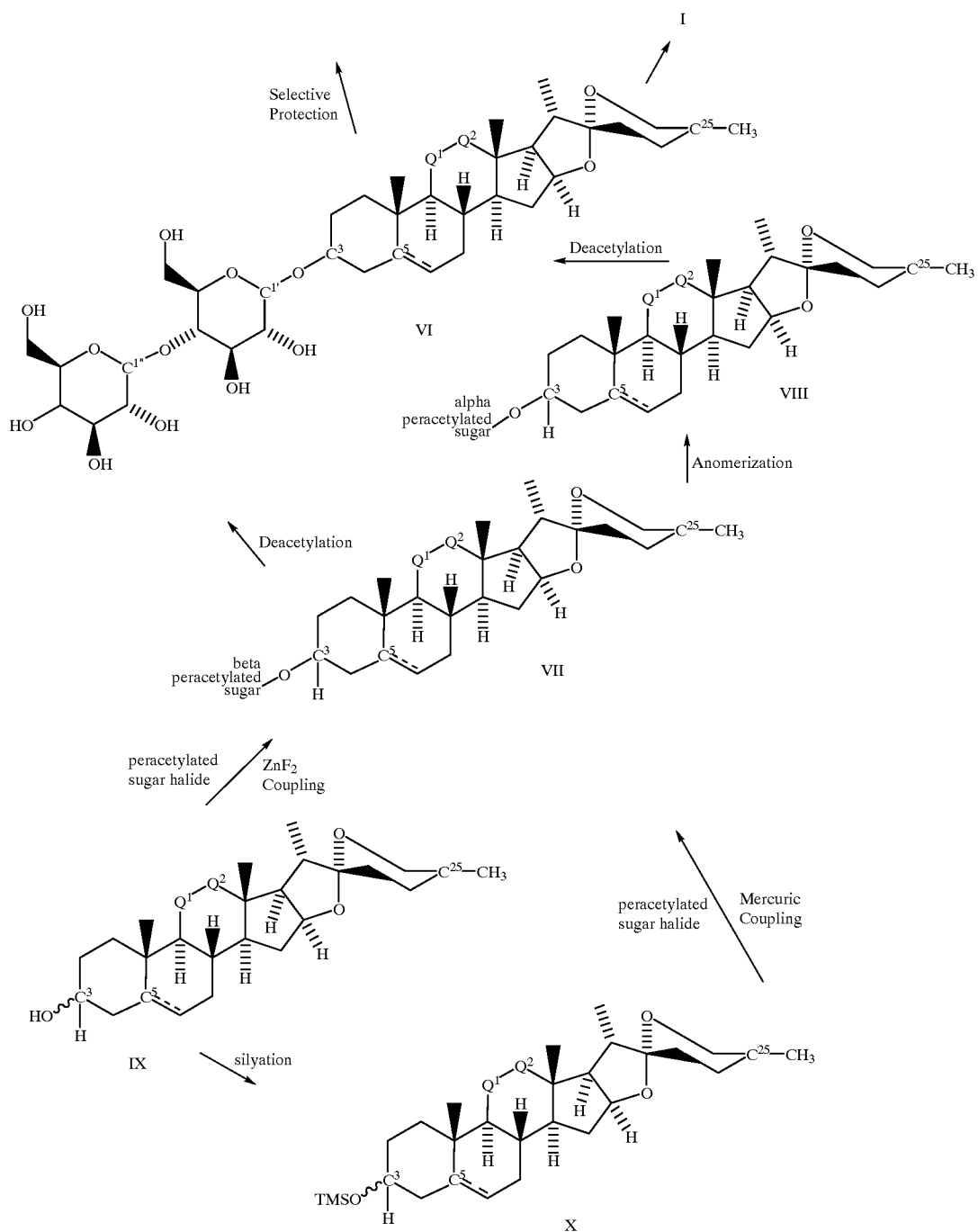

In general the compounds of this invention may be made by coupling the desired protected sugar halide and steroid followed by deprotection. The desired functionality/substituents are attached (following optional selective protection) and a final deprotection is performed. The following text (which is keyed to the above Schemes) provides a more detailed description.

According to reaction Scheme I, the desired Formula I compounds wherein Steroid is the steroidal moiety of the Formula I compound shown above (i.e., wherein $Q^1$, $Q^2$, $C^3$, $C^5$, $C^{25}$ are as defined above) and $C^{1'}$, $C^{1'''}$, $R_1$, $R_2$ and $R_3$ are as defined above may be prepared by deprotecting (e.g., deacetylating) the appropriate Formula II compound wherein Steroid is the steroidal moiety described above, (although hereinafter in the Detailed Description those skilled in the art will realize that in those instances wherein $Q^1$ and/or $Q^2$ is hydroxy the hydroxy may exist in a conventionally protected form as a result of protection of the sugar), $C^{1'}$ and $C^{1'''}$ are as defined above and $R_1$, $R_2$, and $R_3$ are as defined above or each independently is a conventionally protected hydroxyl group such as —OAc.

Typically the deprotection (preferably the deacetylation), is accomplished by combining the Formula II compound with a nucleophilic base such as sodium methoxide or potassium cyanide in a polar solvent such as methanol, tetrahydrofuran, n-propanol or mixtures thereof at temperatures of about 0° C. to about 100° C. (typically at ambient temperatures) and pressures of about 0.5 psi to about 50 psi (typically ambient) for about 0.25 hour to about 2 hours.

Additionally, the compounds may contain a silyl protecting group which can be removed by treating the deacylated product from above with a quaternary ammonium fluoride such as tetrabutyl ammonium fluoride in an anhydrous solvent such as tetrahydrofuran at temperatures of about 0° C. to about 50° C. (typically at ambient temperatures) for about 0.1 to about 3 hours.

The desired Formula II compounds wherein Steroid is the steroid moiety described above and $C^{1'}$ and $C^{1'''}$ are as defined above and at least one of $R_1$, $R_2$ and $R_3$ is hydrogen can be prepared by reduction of the corresponding halogenated compound. Typically, the reduction can be performed by treating the halogenated compound (Br and I preferred) with a reducing agent such as tri-n-butyl tin hydride and a radical initiator such as azoisobutylnitrile (AIBN) in an anhydrous aprotic solvent such as toluene at reflux temperature for about 1 hour to about 5 hours.

The desired Formula II compounds wherein Steroid is the steroidal moiety described above, $C^{1'}$ and $C^{1'''}$ are as described above and at least one of $R_1$, $R_2$ and $R_3$ is halogen may be prepared by halogenation of the appropriately protected Formula V compound wherein Steroid is the steroidal moiety described above, $C^{1'}$ and $C^{1'''}$ are as defined above and $R_1$, $R_2$, and $R_3$ are each independently hydroxy or a conventionally protected hydroxyl group such as —OAc.

Generally the halogenation can be performed by first preparing an appropriately activated and protected form of the Formula V compound (e.g., the Formula IV mesylate) followed by treatment with the desired lithium halide. Typically the mesylation can be performed by combining the Formula V compound and mesyl chloride in the presence of a base, preferably an amine base such as triethylamine and a catalytic amount of a catalyst such as dimethylaminopyridine in an aprotic, anhydrous solvent such as anhydrous dichloromethane at a temperature of about −20° C. to about 20° C. for about one hour to about four hours. The resulting mesylate is then treated with the appropriate lithium halide in a polar solvent such as N, N-dimethylformamide at a temperature of about 70° C. to about 100° C. for about one to about three hours.

Alternatively, the iodination can be performed by combining iodine and the appropriate Formula V compound in an anhydrous aprotic solvent such as toluene (in the presence of imidazole and triphenylphosphine) under reflux conditions and ambient pressure for about four to about eight hours.

Alternatively, the fluorination can be performed by combining the appropriate Formula V compounds with a fluorinating agent such as dialkylaminosulfur trifluoride (e.g., DAST) in an anhydrous, aprotic solvent such as dimethoxy ethane or dichloroethane at a temperature of about −10° C. to about 10° C. and then after about twenty minutes to about two hours raising the temperature to about 30° C. to about 60° C. for about one hour to about four hours.

Alternatively, a selective bromination (i.e., $R_2$=Br) can be accomplished by treating the appropriate Formula V compound (wherein $C^{6'''}$ and $C^{4'''}$ are substituted with OH and $C^6$ is substituted with a conventionally protected hydroxyl group such as —OAc) with carbon tetrabromide and triphenyl phosphine and an amine base such as pyridine in an anhydrous aprotic solvent such as dichloromethane at ambient temperature for about 6 hours to about 48 hours.

The desired Formula II compounds wherein Steroid is the steroidal moiety described above, $C^{1'}$ and $C^{1'''}$ are as described above and at least one of $R_1$, $R_2$ and $R_3$ is $(C_1-C_6)$alkoxy$(C_1-C_6)$alkoxy may be prepared by alkylating the appropriately protected Formula V compound wherein Steroid is the steroidal moiety described above, $C^{1'}$ and $C^1$ are as defined above and $C^{6'}$, $C^{6'''}$ and $C^{4'''}$ are each independently substituted with hydroxy or a conventionally protected hydroxyl group such as —OAc.

Typically, the appropriate Formula V compound is combined with an excess of the appropriate alkoxyalkyl halide and a trialkyl amine base such as diisopropylethylamine in the presence of an anhydrous, aprotic solvent such as dichloroethane at a temperature of about 15° C. to about 35° C. (typically ambient temperature) for about one to about eight hours followed by mixing for one to four hours at a temperature of about 40° C. to about 70° C.

The desired Formula II compounds wherein Steroid is the steroid moiety described above and $C^{1'}$ and $C^{1'''}$ are as defined above and at least one of $R_1$, $R_2$, and $R_3$ is Z—$R_4$ and $R_4$ contains a ketone group can be prepared by oxidation of the corresponding hydroxy substituted Formula II compound. Typically the oxidation is performed by treating the hydroxy compound with an oxidizing agent, such as pyridinium chlorochromate, in an anhydrous halogenated solvent such as dichloromethane at 0° C. to about 30° C., generally at ambient temperatures, for about 2 hours to about 24 hours.

Similarly, Formula II compounds described in the above paragraph wherein $R_4$ contains an alkylsulfinyl group may be prepared by oxidation of the corresponding alkylsulfanyl substituted Formula II compound. Typically the appropriate Formula II compound is treated with one equivalent of a peroxy acid such as meta-chloroperbenzoic acid in an anhydrous halogenated solvent such as dichloromethane at ambient temperature for 1 hour to about 6 hours. The corresponding alkylsulfonyl Formula II compounds can be prepared in an analogous manner using excess peroxy acid.

The desired Formula II compounds wherein Steroid is the steroid moiety described above, and $C^{1'}$ and $C^{1'''}$ are as defined above and at least one of $R_1$, $R_2$, and $R_3$ is Z—$R_4$ and $R_4$ is alkylaminocarbonylalkyl can be prepared from the corresponding carboxy alkyl Formula II compounds through an amide forming reaction. Typically the amide is formed by reacting the carboxylic acid with a carboxyl activating agent such as a substituted carbodiimide and hydroxybenzotriazole and a primary or secondary amine chosen to give the desired amide product. The reaction is typically performed in an anhydrous aprotic solvent such as dichloromethane at ambient temperature for about 0.5 hours to about 6 hours. The carboxy alkyl Formula II compounds used in this procedure are typically prepared from the corresponding benzyl ester (the preparation of the benzyl ester being described herein) by a hydrogenolysis reaction. Thus the ester is treated with a hydrogenation catalyst such as palladium on carbon in an alcoholic solvent such as methanol and placed under 1 to 4 atmospheres of hydrogen, typically 2 atmospheres, for about 0.5 to about 8 hours.

The desired Formula I compounds wherein Steroid is the steroidal moiety described above, $C^{1'}$ and $C^{1'''}$ are as described above and at least one of $R_1$, $R_2$ and $R_3$ is —O—C(=O)—$R_4$ or —O—C(=O)—N($R^5$)—$R_4$ may be prepared by acylating the appropriate Formula VI compound wherein $Q^1$, $Q^2$, $C^{1'}$ and $C^{1'''}$ are as defined above (See Scheme II). Alternatively, the desired formula 11 compounds wherein at least one of $R_1$, $R_2$ and $R_3$ is —O—C(=O)—$R_4$, —O—C(=O)—N($R^5$)—$R_4$ or —O—C(=S)—N($R^5$)—$R_4$ may be prepared by acylating the appropriately protected Formula V compound wherein Steroid is the steroidal moiety described above, $C^{1'}$ and $C^{1'''}$ are as defined above and $C^{6'}$, $C^{6'''}$ and $C^{4'''}$ are each independently substituted with hydroxy or a conventionally protected hydroxyl group such as —OAc (See Scheme I).

A nonselective mixture of esters and carbamoyloxy substitution at $R_1$ and $R_2$ is achieved by treating the appropriately protected perhydroxy sugar Formula VI compound with the appropriate acid chloride or isocyanate and an amine base that also acts as an anhydrous solvent such as pyridine in the presence of a drying agent such as molecular sieves at a temperature of about –60° C. to about 25° C. for about 5 minutes to about 24 hours while the reaction is allowed to warm to ambient temperature. Different products and product mixes result from the variation of the amount of acid chloride or isocyanate used, the length of reaction time and the reactivity of the acid chloride or isocyanate.

Alternatively, a more selective acylation is performed by treating the appropriately protected (e.g., OAc) steroidal glycoside Formula V compound with the appropriate isocyanate or acid chloride in the presence of a base, preferably an amine base such as triethylamine or pyridine and a catalytic amount of an acylation catalyst such as dimethylaminopyridine in an anhydrous, aprotic solvent such as dichloromethane at a temperature of about –20° C. to about 20° C. The reaction mixture is allowed to warm to ambient temperature for about 10 minutes to about two hours. The carbamoylation can also be achieved by treating the appropriately protected Formula V compound with the appropriate isocyanate in the presence of cuprous chloride in a polar aprotic solvent such as dimethylformamide at ambient temperature for two hours to about 10 hours.

The carbamoylation may also be achieved by treating the appropriately protected Formula V compound with the appropriate isocyanate in the presence of a organotin catalyst such as dibutyl tin dilaurate in an anhydrous aprotic solvent such as dichloromethane at ambient temperature for about 2 hours to about 24 hours.

In addition, the desired Formula II compounds wherein at least one of $R_1$,$R_2$ and $R_3$ is a carbamoyloxy or thiocarbamoyloxy moiety may be prepared by treatment of the appropriately protected (e.g., OAc) steroidal glycoside Formula V compound with a phosgene equivalent such as carbonyl diimidazole or a thiophosgene equivalent such as thiocarbonyl diimidazole in the presence of a base, preferably an amine base such as diisopropylethylamine in an aprotic, anhydrous solvent such as dichloroethane at a temperature of about 15° C. to about 30° C. (typically ambient temperature) for about one to about four hours. The appropriate amine is added and the reaction mixture is stirred at the same temperature for about one hour to about six hours, and heated if necessary to about 40° C. to about 60° C. for about one to about four hours.

The desired Formula II compounds wherein Steroid is the steroidal moiety described above, $C^{1'}$ and $C^{1'''}$ are as described above and at least one of $R_1$, $R_2$ and $R_3$ is —NH—C(=O)—$R_4$ or —NH—C(=O)—N($R^5$)—$R_4$ may be prepared by acylating the appropriately protected Formula III compound wherein Steroid is the steroidal moiety described above, $C^{1'}$ and $C^{1'''}$ are as defined above and at least one of $R_1$, $R_2$, and $R_3$ is amino or hydroxy.

Typically the amide may be prepared by the treatment of the appropriately protected (e.g., OAc) steroidal glycosidyl amine with the appropriate acid anhydride or acid chloride in the presence of a base, preferable an amine base such as triethylamine in an anhydrous, aprotic solvent such as dichloromethane for about one to about three hours at a temperature of about 0° C. to about 25° C.

Alternatively, the ureas may be prepared by the treatment of the appropriately protected (e.g., OAc) steroidal glycosidyl amine with the appropriate isocyanate in an anhydrous, aprotic solvent such as dichloromethane for about one to about three hours at a temperature of about 0° C. to about 25° C.

The desired Formula III compound (which happens in this case to be a Formula II compound) wherein Steroid is the steroidal moiety described above, $C^{1'}$ and $C^{1'''}$ are as defined above and at least one of $R_1$, $R_2$, and $R_3$ is amino or azido may be prepared from the corresponding Formula IV mesylated or halogenated compounds by azide displacement followed if necessary by reduction.

Typically the mesylate or halogen compound is exposed to a metal azide such as sodium azide in a polar, aprotic solvent such as N, N,-dimethylformamide (in an inert atmosphere) at a temperature of about 70° C. to about 150° C. for about two to about 10 hours. The preparation of such mesylate compounds are described above for the lithium halide halogenation. Typically the azido compounds are reduced to the corresponding amines by exposure to hydrogen gas in the presence of a noble metal catalyst such as palladium on carbon at ambient temperature for about four to about forty eight hours, under pressures of about one to about three atmospheres.

The desired Formula V compound (appropriately protected to yield the desired substitution described above) wherein Steroid is the steroidal moiety described above, $C^{1'}$ and $C^{1'''}$ are as defined above and $C^{6'}$, $C^{6'''}$ and $C^{4'''}$ are each independently substituted with hydroxy or a conventionally protected hydroxyl group such as —OAc may be prepared by conventional protecting group methods of organic synthesis known to those skilled in the art from the corresponding Formula VI compounds wherein $Q^1$, $Q^2$, $C^3$, $C^5$, $C^{25}$, $C^{1'}$ and $C^{1'''}$ are as defined above. For a general description of protecting groups and their use, see T. W. Greene, *Protective Groups in Organic Synthesis*, John Wiley & Sons, New York, 1991. In addition, as an aid to the preparation of the above protected steroidal glycosides, the following paragraphs describe the preparation of various protected steroidal glycosides from their hydroxy analogues using a combination of differentially selective protecting groups and sequential protection reactions.

For example, the desired Formula V compound wherein Steroid is the steroidal moiety described above, $C^{1'}$ and $C^{1'''}$ are as defined above, $C^{6'}$ and $C^{6'''}$ are substituted with hydroxy and $C^{4'''}$ is substituted with OP where P is acyl may be conveniently prepared from the corresponding perhydroxy steroidal glycoside by silylation, acylation and desilylation. The appropriate Formula VI compound is reacted with a base, preferably an amine base such as imidazole, a bulky silylating agent selected to afford the desired selective protection such as a trisubstitutedsilylhalide, preferably t-butyidiphenylsilyl chloride and a catalytic amount of a silylation catalyst such as dimethylaminopyridine in an anhydrous, aprotic solvent such as N, N-dimethylformamide at about –20° C. to about 10° C. followed by ambient temperature stirring for about one to about six hours. Upon completion of the silylation, a base, preferably an amine base such as pyridine and an acylating agent selected to afford the desired acyl protecting group defined above such as acetic anhydride are added at ambient temperature and pressure for about three to about twelve hours to achieve acetylation to prepare the desired protected compound (e.g., Formula IIB compound). The resulting product is treated with hydrogen fluoride in an anhydrous, aprotic solvent such as pyridine at about –20° C. to about 10° C. followed by ambient temperature stirring for about two to about six hours to prepare the desired selectively protected compound (e.g., Formula IIA compound). This product contains hydroxyl groups at the $C^{6'}$ and $C^{6'''}$ positions which can be further differentiated by reaction with one equivalent of a protecting group such as acetic anhydride in the presence of a base, such as pyridine at ambient temperatures for about 1 to about 4 hours. This procedure gives a mixture of Formula V compounds which contain a single hydroxyl group at either the $C^{6'}$ or the $C^{6'''}$ position which can be separated chromatographically.

In addition, the desired Formula V compound wherein Steroid is the steroidal moiety described above, $C^{1'}$ and $C^{1'''}$ are as defined above, $C^{6'}$ and $C^{4'''}$ are substituted with hydroxy and $C^{6'''}$ is substituted with OP where P is acyl may be conveniently prepared from the corresponding perhydroxy steroidal glycoside by ketalization, acylation and deketalization. The appropriate Formula VI compound is reacted with an acetal or ketal selected to afford the desired cyclic protecting group defined above such as benzaldehyde dimethyl acetal or anisaldehyde dimethyl acetal in the presence of a catalytic amount of a strong acid such as camphorsulfonic acid in an anhydrous, aprotic solvent such as chloroform or dichloroethane under reflux conditions for about two to about six hours at ambient pressure. Upon completion of the ketalization, a base preferably an amine base such as pyridine, a catalytic amount of an acylation catalyst such as dimethylaminopyridine and an acylating agent selected to afford the desired acyl protecting group defined above such as acetic anhydride or chloroacetic anhydride were added at a temperature of about –20° C. to about 10° C. followed by ambient temperature stirring for about one to about twelve hours to prepare the desired protected compound. The resulting product is treated with 80% acetic acid in water at about 50° C. to about reflux conditions for about one to about four hours or with trifluoroacetic acid in a mixture of dichloromethane and methanol at ambient temperature for about two to about eight hours to prepare the desired protected compound (e.g., Formula IIA compound).

This product can further be converted to the Formula V compound wherein $C^{6'}$ and $C^{6'''}$ are substituted with OP where P is an acyl or silyl protecting group and $C^{4'''}$ is substituted with OH by a selective silylation reaction. Typically the silylation is performed by treating the appropriate Formula V compound wherein $C^{4'''}$ and $C^{6'''}$ are substitued with OH and $C^{6'}$ is substituted with OP where P is an acyl protecting group with a silylating agent such as tert-butyldimethylsilyl chloride and a base preferably an amine base such as imidazole in a polar aprotic solvent such as dimethyl formamide at ambient temperature for about 12 hours to about 48 hours.

The desired Formula V compound wherein Steroid is the steroidal moiety described above, $C^{1'}$ and $C^{1'''}$ are as defined above, $C^{6'''}$ and $C^{4'''}$ are substituted with hydroxy and $C^{6'}$ is substituted with OP where P is an ether protecting group may be conveniently prepared from the corresponding perhydroxy steroidal glycoside by ketalization, etherification and deketalization. The ketalization is performed as described above. Upon completion, the solvent is removed and replaced with a polar aprotic solvent such as dimethylformamide. The appropriate alkyl halide is added such as benzyl bromide, followed by a strong base such as sodium hydride at a temperature of about –20° C. to about 0° C. for about 1 hour to about 12 hours. The deketalization is performed as described above.

The desired Formula VI compounds wherein $Q^1$, $Q^2$, $C^3$, $C^5$, $C^{25}$, $C^{1'}$ and $C^{1'''}$ are as defined above may be prepared from the corresponding Formula VII or Formula VIII peracetylated steroidal glycoside by the deacetylation process described above. For those Formula VI compounds wherein the $C^{1'}$ anomeric oxy is alpha an anomerization is performed on the corresponding Formula VII compound wherein the $C^{1'}$ anomeric oxy is beta prior to deacetylation. The stereochemical terms alpha and beta refer to the configuration of the attachment carbon of the sugar. Typically the anomerization is performed by treatment with a mineral acid such as hydrobromic acid in an anhydrous aprotic solvent such as methylene chloride at temperatures of 20° C. to about 40° C. (typically ambient) for at least 24 hours, typically to several days.

The desired Formula VII compounds wherein $Q^1$, $Q^2$, $C^3$, $C^5$ and $C^{25}$ are as described above may be prepared by coupling the appropriate acetylated sugar halide (e.g., bromide) and steroid. More specifically, for those Formula VII compounds where the sugar is other than beta-D-maltosyl, a zinc fluoride promoted coupling of the appropriate Formula IX compound (wherein $Q^1$, $Q^2$, $C^3$, $C^5$ and $C^{25}$ are as described above) and peracetylated sugar halide is used. For those Formula VII compounds where the sugar is beta-D-maltosyl, a mercuric bromide and mercuric cyanide promoted coupling of the appropriate Formula X compound (e.g., trimethyl silyl ether of the Formula IX compound wherein $Q^1$, $Q^2$, $C^3$, $C^5$ and $C^{25}$ are as described above) and peracetylated sugar halide is used.

Generally, the zinc fluoride promoted coupling of the Formula IX compound and the peracetylated sugar bromide occurs in a non-protic, anhydrous reaction-inert solvent (e.g., acetonitrile) at a temperature of about 20° C. to about 100° C. for about 0.5 to about 12 hours. Typically about 0.5 to about 4 equivalents (based on Formula IX compound) zinc fluoride is used and about 0.5 to about 3 equivalents acetylated sugar bromide is used. Preferably the coupling is acid catalyzed and it is especially preferred that hydrohalic acid generated during the reaction is used as the acid catalyst. The desired compounds may be prepared at pressures of 0.5 to 50 psi, although typically ambient pressures are used. In a preferred isolation technique the glycosides may be precipitated from the crude filtered reaction mixture (e.g., acetonitrile product solution) by the addition of about 25% to 75% water and the remainder alcohol (e.g., methanol). Precipitation of the product from aqueous methanol/acetonitrile requires less processing than an extractive isolation, and provides a product of greater purity. Generally, the mercuric bromide and mercuric cyanide promoted coupling of the Formula X compound and the acetylated beta-D-maltosyl bromide is performed in an aprotic, anhydrous solvent such as methylene chloride at a temperature of about 20° C. to about 100° C. for about 0.5 to about 6 hours. Typically about 0.5 to about 4 equivalents (based on acetylated beta-D-maltosyl bromide) mercuric bromide and mercuric cyanide is used and about 0.5 to about 3 equivalents peracetylated beta-D-maltosyl bromide is used. The desired compounds may be prepared at pressures of 0.5 to 50 psi, although typically ambient pressures are used. Preferably they are isolated as described for the zinc fluoride promoted coupling of the Formula IX compound.

The desired Formula X compounds wherein $Q^1$, $Q^2$, $C^3$, $C^5$ and $C^{25}$ are as described above may be prepared by silylating the appropriate Formula IX compound wherein $Q^1$, $Q^2$, $C^3$, $C^5$ and $C^{25}$ are as described above. Generally the Formula IX compound, a base such as triethylamine and an activated trialkylsilyl compound (e.g., trimethylsilyl trifluoromethane sulfonate of trimethylsilyl chloride) are reacted in an aprotic, anhydrous solvent such as methylene chloride at a temperature less than about 10° C. for about 0.5 hour to about two hours.

In general, the procedures described above may be combined thus providing Formula I compounds wherein the $R_1$, $R_2$ and/or $R_3$ groups are dissimilar (e.g.. halogenation followed by carbamoylation).

The starting materials for the above described reaction schemes (e.g., alkoxyalkyl halide, acid anhydride, peracetylated sugar halides, acid chlorides, isocyanates, steroids, amines, trialkylsilylchlorides, carbonyl diimidazoles, thiocarbonyl diimidazoles, acid derivatives, acetals, ketals, protecting groups) are readily available or can be easily synthesized by those skilled in the art using conventional methods of organic synthesis. For example some of the compounds of this invention require the synthesis of substituted amines and carboxylic acids which eventually will become $R_4$ groups. Such preparations are standard and known to those skilled in the art.

In addition, as an aid to the preparation of the above steroids, the following paragraphs describe the preparation of the various Formula IX compounds from 12-keto analogs (e.g., hecogenin). Literature references for the preparation of Formula IX steroid compounds (wherein $Q^1$ is methylene and $Q^2$ is carbonyl and the stereochemistry of the $C^5$ hydrogen (or lack of the $C^5$ hydrogen) and $C^{25}$ carbon are as defined below) are described in Table I.

TABLE I

Formula IX Compounds Where $Q^1$ is Methylene, $Q^2$ is carbonyl and the $C^3$ Hydroxy Group is Beta

| $C^5$ hydrogen | $C^{25}$ | $C^5$-$C^6$ double bond | Reference |
| --- | --- | --- | --- |
| α | R | No | Marker et. al., J. Am. Chem. Soc. (1947) 69, 2167. |
| α | S | No | Callow & James J. Chem. Soc. (1955) 1671. |
| β | R | No | Marker et. al., J. Am. Chem. Soc. (1947) 69, 2167. |
| β | S | No | Kenney & Wall J. Org. Chem. (1957) 22, 468. |
| — | R | Yes | Walens, et al., J. Org. Chem. (1957) 22, 182. |
| — | S | Yes | Walens, et al., J. Org. Chem. (1957) 22, 182. |

The following paragraphs describe and/or give literature references for the preparation of the various steroids used as starting materials (i.e., the alternative stereochemistry at the $C^3$ position and the oxygenation and different epimers at $C^{11}$ ($Q^1$) and $C^{12}$ ($Q^2$) from the above Formula IX compounds described in Table I. In general the preparation of the different oxygenated steroids is independent of the stereochemistry at the $C^3$, $C^5$ (or lack of the $C^5$ hydrogen) and $C^{25}$ positions. Thus, once the appropriate stereochemistry at the $C^3$, $C^5$ (or lack of the $C^5$ hydrogen) and $C^{25}$ positions are achieved where $Q^1$ is methylene and $Q^2$ is carbonyl, the various oxygenated compounds at $Q^1$ and $Q^2$ may be prepared therefrom.

Some of the preparation methods described herein will require protection of remote functionality (i.e., $C^{11}$ ($Q^1$) and $C^{12}$ ($Q^2$)). The need for these protecting groups will vary depending on the nature of the remote functionality and the conditions of the preparation methods. This need is readily determined by one skilled in the art. For a general description of protecting groups and their use, see T. W. Greene, *Protective Groups in Organic Synthesis*, John Wiley & Sons, New York, 1991.

The Formula IX compounds wherein $Q^1$ is methylene, $Q^2$ is carbonyl and the $C^3$ hydroxy is beta may be converted to the corresponding Formula IX compounds where the $C^3$ hydroxy is alpha by the following two procedures. These preparative methods may be used independent of the $C^{25}$ stereochemistry.

The carbonyl is protected as a ketal (e.g., ethylene ketal), by reacting the steroid with ethylene glycol and an acid catalyst according to the procedure of Engel and Rakhit, Can. J. Chem, 40, 2153, 1962. When the $C^5$ hydrogen is alpha, the $C^3$ hydroxy group is oxidized to the ketone using pyridinium chloro chromate (PCC) in methylene chloride at ambient conditions. Then the $C^3$ ketone is reduced with a sterically hindered reducing agent such as K-Selectride® reducing agent, at low temperature in tetrahydrofuran to give the $C^3$ alpha alcohol according to Gondos and Orr, J. Chem. Soc. Chem. Commun. 21, 1239, 1982. The $Q^2$ ($C^{12}$) protecting group is removed with acid, such as hydrochloric acid, in an appropriate solvent such as acetone.

For those compounds wherein the $C^5$ hydrogen is beta the same procedures are used as were used when the $C^5$ hydrogen is alpha except the $C^3$ ketone is reduced using sodium borohydride in ethanol to furnish the $C^3$ alpha alcohol.

Reaction Scheme III illustrates the reaction pathways to achieve the Formula IX compounds wherein $Q^1$ ($C^{11}$) and $Q^2$ ($C^{12}$) are defined above starting from the Formula IX compound wherein $Q^1$ is methylene and $Q^2$ is carbonyl.

In general, preparation methods for these compounds may be found in L. F. Fieser and M. Fieser, *Steroids*, Reinhold Pub. Corp., New York, 1959 and references therein, however, the following descriptive text (which is keyed to Reaction Scheme III) provides specific guidance.

Briefly according to Reaction Scheme III method 1, the starting material is acetylated and brominated according to the procedure described in *J. Chem. Soc.,* 1956, 4344. This intermediate is then reduced with lithium aluminum hydride and treated with silver oxide by a procedure similar to that described in *Helv. Chim. Act.,* 1953, 36, 1241. The resulting β-11,12-epoxide is opened with trichloroacetic acid, saponified and reduced with zinc and acetic acid using the procedure described in *J. Chem. Soc.,* 1956, 4330 to give the product shown for method 1.

In method 2, the starting material is selectively acetylated using the procedure described in *J. Chem. Soc.,* 1956, 430. Using the procedure described in *Org. Syn.,* 1976, 55, 84, the resulting product is oxidized with chromium trioxide and pyridine. Using the procedure described in *Synthesis,* 1973, 790, the resulting product is saponified with potassium cyanide in water, methanol and THF to give the product shown for method 2. In method 3, the starting material is converted to the corresponding toluenesulfonylhydrazone which is in turn treated with sodium methoxide using a procedure similar to that described in *J. Am. Chem. Soc.,* 1954, 76, 4013. The resulting 11-ene product is oxidized with osmium tetroxide and N-methylmorpholine-N-oxide according to the procedure describe in *Tetrahedron Letters,* 1976, 1973 to give the product shown for method 3.

In method 4, the starting material is monobrominated using a procedure described in U.S. Pat. No. 3,178,418. Hydrolysis of this intermediate using the procedure described in *J. Chem. Soc.,* 1956, 4330 gives the product shown for method 4.

In method 5, the starting material is reduced with lithium aluminum hydride according to the procedure described in *J. Am. Chem. Soc.,* 1951, 73, 1777 to give the product shown.

In method 6, the starting material is reduced with lithium and ammonia according to the procedure described in *J. Am. Chem. Soc.,* 1953, 75, 1282 to give the product shown.

In method 7, the starting material is acetylated according to the procedure described in *J. Am. Chem. Soc.,* 1955, 77, 1632 to give a mixture of acetates from which the 3,11-diacetate can be isolated. The unprotected 12-alcohol is then oxidized with chromium trioxide and pyridine according to the procedure described in *Org. Syn.,* 1976, 55, 84. Saponification of the acetates gives the product shown for method 7.

In method 8, the starting material is diacetylated using the procedure described in *J. Chem. Soc.,* 1956, 4330. The diacetate is reduced with calcium and ammonia using the procedure described in *J. Chem. Soc.,* 1956, 4334 to give the product shown for method 8.

In method 9, the starting material is reduced with lithium and ammonia according to the procedure described in. *J. Am. Chem. Soc.,* 1953, 75, 1282 to give the product shown.

In method 10, the starting material is reduced with lithium aluminum hydride according to the procedure described in *J. Am. Chem. Soc.,* 1951, 73, 1777 to give the product shown. In method 11, the starting material is selectively protected at the 3-alcohol with t-butyldimethylchlorosilane and imidazole using the procedure described in *J. Am. Chem. Soc.,* 1972, 94, 6190. Using the procedure described in *Org. Syn.,* 1976, 55, 84, the product is oxidized with chromium trioxide and pyridine. The 3-alcohol is then desilylated with hydrofluoric acid in acetonitrile using the procedure described in *J. Am. Chem. Soc.,* 1972, 94, 6190 to give the product shown for method 11.

In method 12, the starting material is selectively protected at the 3-alcohol with t-butyldimethylchlorosilane and imidazole using the procedure described in *J. Am. Chem. Soc.,* 1972, 94, 6190. The resulting intermediate is reduced with lithium aluminum hydride using the procedure described in *J. Am. Chem. Soc.,* 1951, 73, 1777. The resulting intermediate is selectively acetylated on the 12-alcohol, silylated on the 11-alcohol with trimethylsilyltriflate and 2,6-lutidine using the procedure described in *Tetrahedron Letters,* 1981, 22, 3455, and then deacetylated at the 12-alcohol with lithium aluminum hydride and an aqueous ammonium chloride quench. The 12-alcohol is oxidized with chromium trioxide and pyridine in methylene chloride using the procedure described in *Org. Syn.,* 1976, 55, 84, and then desilylated with hydrofluoric acid in acetonitrile using the procedure described in *J. Am. Chem. Soc.,* 1972, 94, 6190 to give the product shown in method 12.

The compounds of Formula I which have been obtained and have asymmetric carbon atoms (e.g., some of the components of the carbamoyl moieties such as substituted amino groups) can be separated into their diastereomers and enantiomers on the basis of their physical chemical differences or optical qualities by methods known per se., for example, by chromatography and/or fractional crystallization. All such isomers, including diastereomers and enantiomers are considered as part of this invention.

The compounds of this invention where $R_4$ contains an amine group are basic and they form acid salts. All such acid salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, In the case of aqueous solutions, by lyophilization, as appropriate.

In addition, many of the compounds of this invention may be isolated as hydrates.

The compounds of this invention are potent inhibitors of cholesterol absorption and thus are all adapted to therapeutic use as hypercholesterolemia controlling agents in mammals, particularly humans. Since hypercholesterolemia is closely related to the development of generalized cardiovascular, cerebral vascular or peripheral vascular disorders, secondarily these compounds prevent the development of atherosclerosis particularly arteriosclerosis.

The hypercholesterolemia controlling activity of these compounds may be demonstrated by methods based on standard procedures. For example, the in vivo activity of these compounds in inhibiting intestinal absorption of cholesterol may be determined by the procedure of Melchoir and Harwell (*J. Lipid Res.,* 1985, 26, 306–315).

Activity can be determined by the amount of hypocholesterolemic agent that reduces the cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day the animals are fasted for 18 hours, then administered a 1.5 ml oral bolus of water containing 0.25% methylcellulose, 0.6% Tween™ 80 and 10% ethanol (control animals) or an oral bolus that contains, in addition, the desired concentration of the compound to be tested. Immediately following bolus administration, the animals receive a second 1.5 ml oral bolus of liquid hamster diet containing 1% [$^3$H] cholesterol (2.0 μCi/animal; 210 dpm/nmol) and 0.5% cholic acid, and are fasted for an additional 24 hours. At the end of this second fasting period animals are sacrificed, livers are excised, saponified and aliquots are decolorized by addition of hydrogen peroxide, and assessed for radioactivity. Total hepatic radioactivity is calculated based on measured liver weights. The degree of cholesterol absorption is expressed as a percentage of the total radioactivity administered as an oral bolus that is present in the liver 24 hours following bolus administration.

Anti-atherosclerosis effects of the compounds can be determined by the amount of agent that reduces the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean ±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention can be via any method which delivers the compounds to the intestinal lumen. These methods include oral routes, intraduodenal routes etc.

The amount of steroidal glycoside administered will, of course, be dependent on the subject being treated, on the severity of the affliction, on the manner of administration and on the judgement of the prescribing physician. However, an effective dosage is in the range of 0.005 to 20 mg/kg/day, preferably 0.01 to 5 mg/kg/day, most preferably 0.01 to 1 mg/kg/day. For an average 70 kg human, this would amount to 0.00035 to 1.4 g/day, preferably 0.0007 to 0.35 g/day, most preferably 0.0007 to 0.07 g/day. In one mode of administration the compounds of this invention are taken with meals.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition orformulation to be administered will contain a quantity of a compound according to the invention in an amount effective to alleviate the signs of the subject being treated, i.e., hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see *Remington's Pharmaceutical Sciences*, Mack Publishing Company, Easter, Pa., 15th Edition (1975).

It should be understood that the invention is not limited to the particular embodiments shown and described herein, but that various changes and modifications may be made without departing from the spirit and scope of this novel concept as defined by the following claims.

EXAMPLE 1

(3β,5α, 25R)-3-[(4"-[2-fluoro-phenylcarbamoyl]-β-D-cellobiosyl)oxy]-spirostan-11-one Desilylation Tetra-n-butyl ammonium fluoride (0.92 mL of a 1 M solution in THF, 0.92 mmol) was added to a solution (3β,5α, 25R)-3-[(4"-[2-fluoro-phenylcarbamoyl]-6"-triisopropylsilyl-β-D-cellobiosyl)oxy]-spirostan-11-one (321 mg, 0.31 mmol) in THF (5 mL) at room temperature. After 30 min, the mixture was concentrated in vacuo and the residue was dissolved in methanol (1 mL) and the product was precipitated by the addition of water (5 mL). The solid was collected by vacuum filtration, washed with water and dried to afford 190 mg of the title product as a colorless solid (70%). m.p. >265° C. FAB MS: 914 (M+Na)$^+$. Analysis calc. for C$_{46}$H$_{66}$FNO$_{15}$+0.4 H$_2$O: C 61.44; H 7.49; N 1.56. Found: C 61.14; H 7.45; N 1.59.

EXAMPLE 2

(3β,5α,25R)-3-[(6',6"-Bis-[phenylcarbamoyl]-β-D-cellobiosyl)oxy]-spirostan-11-one Deacetylation Using Sodium Methylate To a solution of (3β,5α,25R)-3-[(6',6"-bis-[phenylcarbamoyl]-penta acetyl-β-D-cellobiosyl)oxy] spirostan-1 1-one (0.67 g, 0.56 mmol) in tetrahydrofuran (4 mL) and methanol (4 mL), sodium methylate (37 mg) was added. The reaction was stirred for 45 minutes at room temperature under nitrogen atmosphere. Upon completion, the reaction was quenched with acetic acid (2–3 drops) and concentrated in vacuo. The crude material was purified via flash chromatography (95% chloroform: 5% methanol). The isolated product was concentrated in vacuo to partial dryness and water was added causing a precipitate to form. The precipitated product was filtered, washed with water and oven-dried to afford 189 mg (33.9% yield) of the title compound. $^1$HNMR (250 MHz, DMSO-d$_6$) δ 9.65 (2, 1H); 8.35 (s, 1H); 7.6–7.9 (m, 10 H); 5.4–5.1 (m, 4H); 4.65–2.95 (m, 19H); 2.6–1.0 (m, 25H); 0.9 (d, 3H, J=8 Hz); 0.87 (s, 3H); 0.75 (d, 3H, J=8 Hz); 0.6 (2, 3H). FAB MS: 1015 (M+Na)$^+$; Analysis: calculated for C$_{53}$H$_{72}$N$_2$O$_{16}$.1 H$_2$O C 61.85, H 7.44, N 2.72; found C 62.23, H 7.29, N 2.59; m.p. 244–246° C. (dec).

EXAMPLES 3–77

The following compounds were prepared from the appropriate starting material in an analogous manner using the above procedure.

| Example) m.p. | Name M.S. | formula | elemental analysis | |
|---|---|---|---|---|
| 3) | (3β,5α, 25R)-3-[(6',6"-dideoxy-6',6"-difluoro-β-D-cellobiosyl)oxy]-spirostan-11-one | | | |
| >270° C. | 759(M + H)$^+$ | C$_{39}$H$_{60}$F$_2$O$_{12}$ +1.0 H$_2$O | calc. found | C 60.29; H 8.04 C 60.12; H 8.11 |
| 4) | (3β,5α,25R)-3-[(6"-deoxy-6"-fluoro-β-D-cellobiosyl)oxy]-spirostan-11-one | | | |
| 268–269° C. | 757(M + H)$^+$ | C$_{39}$H$_{61}$FO$_{13}$ | calc. found | C 61.89; H 8.12 C 61.68; H 7.77 |
| 5) | (3β,5α,25R)-3-[(6',6"-dideoxy-6',6"-difluoro-β-D-maltosyl)-spirostan-11-one | | | |
| >250° C. | 759(M + H)$^+$ | C$_{39}$H$_{60}$F$_2$O$_{12}$ +0.5 H$_2$O | calc. found | C 61.00; H 8.01 C 60.81; H 7.93 |
| 6) | (3β,5α,25R)-3-[(6',6"-ethoxymethyl-β-D-cellobiosyl)oxy]-spirostan-11-one | | | |
| 216–218° C. (dec) | 893(M + Na)$^+$ | C$_{45}$H$_{74}$O$_{16}$ +0.5 H$_2$O | calc. found | C 61.42; H 8.59 C 61.58; H 8.76 |
| 7) | (3β,5α, 25R)-3-[(6',6"-dideoxy-6',6"-dichloro-β-D-cellobiosyl)oxy]-spirostan-11-one | | | |
| 260° C. (dec) | 791(M + H)$^+$ | C$_{39}$H$_{60}$Cl$_2$O$_{12}$ +0.5 H$_2$O | calc. found | C 58.50; H 7.68 C 58.59; H 7.69 |
| 8) | (3β,5α, 25R)-3-[(6',6"-dideoxy-6',6"-diiodo-β-D-cellobiosyl)oxy]-spirostan-11-one | | | |
| 200° C. (dec) | 975(M + H)$^+$ | C$_{39}$H$_{60}$I$_2$O$_{12}$ +0.5 H$_2$O | calc. found | C 47.62; H 6.25 C 47.73; H 5.99 |
| 9) | (3β,5α,25R)-3-[(6',6"-Bis[2,4-difluoro-phenylcarbamoyl]-β-D-cellobiosyl)oxy]-spirostan-11-one | | | |
| 250° C. | 1087(M + Na)$^+$ | C$_{53}$H$_{68}$F$_4$N$_2$O$_{16}$ +0.6 H$_2$O | calc. found | C 59.17; H 6.48; N 2.60 C 58.92; H 6.61; N 2.59 |
| 10) | (3β,5α,25R)-3-[(6',6"-dideoxy-β-D-cellobiosyl)oxy]-spirostan-11-one | | | |
| >275° C. | 724(M + H)$^+$ | C$_{39}$H$_{62}$O$_{12}$ +0.75 H$_2$O | calc. found | C 63.60; H 8.69 C 63.61; H 8.94 |
| 11) | (3β,5α,25R)-3-[(6',6"-Bis[pivaloyl]-β-D-cellobiosyl)oxy]-spirostan-11-one | | | |
| 224–226° C. (dec) | 923(M + H)$^+$ | HRMS calc. for C$_{49}$H$_{79}$O$_{16}$ | found | 923.5368 923.5284 |
| 12) | (3β,5α,25R)-3-[(6"-[2,4-difluoro-phenylcarbamoyl]-β-D-cellobiosyl)oxy]-spirostan-11-one | | | |
| >265° C. | 910(M + H)$^+$ | C$_{46}$H$_{65}$F$_2$NO$_{15}$ | calc. found | C 60.71; H 7.20; N 1.54 C 60.36; H 6.89; N 1.28 |
| 13) | (3β,5α,25R)-3-[(4",6"-Bis[2-methoxy-phenylcarbamoyl]-β-D-cellobiosyl)oxy]-spirostan-11-one | | | |
| >265° C. | 1075(M + Na)$^+$ | C$_{55}$H$_{76}$N$_2$O$_{18}$ +2.5 H$_2$O | calc. found | C 60.15; H 7.43; N 2.55 C 60.23; H 7.14; N 2.36 |
| 14) | (3β,5α,25R)-3-[(6"-[2-methoxy-phenylcarbamoyl]-β-D-cellobiosyl)oxy]-spirostan-11-one | | | |
| 247–248° C. | 926(M + Na)$^+$ | C$_{47}$H$_{67}$NO$_{16}$ +1 H$_2$O | calc. found | C 61.22; H 7.76; N 1.52 C 61.33; H 7.56; N 1.32 |
| 15) | (3β,5α,25R)-3-[(4",6"-Bis[4-hydroxy-butylcarbamoyl]-β-D-cellobiosyl)oxy]-spirostan-11-one | | | |
| 228–230° C. | 1007(M + Na)$^+$ | C$_{47}$H$_{80}$N$_2$O$_{18}$ +2.5 H$_2$O | calc. found | C 57.13; H 8.31; N 2.72 C 56.98; H 8.42; N 2.34 |
| 16) | (3β,5α,25R)-3-[(4",6"-Bis[2,6-dimethyl-phenylcarbamoyl]-β-D-cellobiosyl)oxy]-spirostan-11-one | | | |
| >250° C. | 1071((M + Na)$^+$ | C$_{57}$H$_{80}$N$_2$O$_{16}$ +2 H$_2$O | calc. found | C 63.12; H 7.75; N 2.58 C 62.98; H 7.88; N 2.60 |
| 17) | (3β,5α,25R)-3-[(4",6"-Bis[2,5-difluoro-phenylcarbamoyl]-β-D-cellobiosyl)oxy]-spirostan-11-one | | | |
| >250° C. | 1087(M + Na)$^+$ | C$_{53}$H$_{68}$F$_4$N$_2$O$_{16}$ +2 H$_2$O | calc. found | C 57.84; H 6.54; N 2.54 C 57.54; H 6.73; N 2.52 |
| 18) | (3β,5α,25R)-3-[(6',6"-dideoxy-6',6"-dichloro-β-D-lactosyl)oxy]-spirostan-11-one | | | |
| 243–244° C. | 813(M + Na)$^+$ | C$_{39}$H$_{60}$Cl$_2$O$_{12}$ +1.5 H$_2$O | calc. found | C 57.21; H 7.75 C 57.49; H 7.52 |
| 19) | (3β,5α,12β,25R)-3-[(4",6"-Bis[2-fluoro-phenylcarbamoyl]-β-D-cellobiosyl)oxy]12-hydroxy-spirostan-11-one | | | |
| 211.5–212° C. | 1067(M + Na)$^+$ | C$_{53}$H$_{70}$F$_2$O$_{17}$ +2 H$_2$O | calc. found | C 58.88 H 6.90 N 2.59 C 59.09 H 6.81 N 2.86 |
| 20) | (3β,5α,12β,25R)-3-[(6',6"-dideoxy-6',6"-difluoro-β-D-cellobiosyl)oxy]-12-hydroxy-spirostan-11-one | | | |
| 239–40° C. (dec) | 797(M + Na)$^+$ | HRMS calc. for C$_{39}$H$_{60}$F$_2$O$_{13}$Na: | found | Na 797.3825 797.3900 |
| 21) | (3β,5α,25R)-3-[(6'-deoxy-6'-fluoro-β-D-cellobiosyl)oxy]12-hydroxy-spirostan-11-one | | | |
| 268–69° C. | 794(M + Na)$^+$ | HRMS calc. for C$_{39}$H$_{61}$FO$_{14}$Na: | | 795.3943 |

-continued

| Example) m.p. | Name M.S. | formula | elemental analysis |
|---|---|---|---|
| (dec) | | | found 795.3881 |
| 22) (3β,5α,25R)-3-[(4",6"-Bis[2-methoxycarbonyl-phenylcarbamoyl]-β-D cellobiosyl)oxy]-spirostan-11-one | | | |
| 245–246° C. dec | 1131 (M + Na)+ | $C_{57}H_{76}N_2O_{20}$ +1 $H_2O$ | calc. C 60.73; H 6.97; N 2.49 found C 60.45; H 6.81; N 2.38 |
| 23) (3β,5',25R)-3-[(6Δ-[4-phenoxy-phenylcarbamoyl-β-D-cellobiosyl)oxy]-spirostan-11-one | | | |
| 264–265° C. | 988 (M + Na)+ | $C_{52}H_{71}NO_{16}$ +1.5$H_2O$ | calc. C 62.89; H 7.51; N 1.41 found C 62.97; H 7.20; N 1.65 |
| 24) (3β,5α,25R)-3-[(4",6"-Bis[allylcarbamoyl]-β-D-cellobiosyl)oxy]-spirostan-11-one | | | |
| 255–260° C. dec | 943 (M + Na)+ | $C_{47}H_{72}N_2O_{16}$ +1.5 $H_2O$ | calc. C 59.54; H 7.97; N 2.95 found C 59.74; H 8.28; N 2.91 |
| 25) (3β,5α,25R)-3-[(4",6"-Bis[3.5-dimethoxy-phenylcarbamoyl]-β-D-cellobiosyl)oxy]-spirostan-11-one | | | |
| 263–264° C. | 1135 (M + Na)+ | $C_{57}H_{80}N_2O_{20}$ +1.8 $H_2O$ | calc. C 59.76; H 7.35; N 2.45 found C 59.93; H 7.00; N 2.26 |
| 26) (3β,5α,25R)-3-[(6"-acetamido-6"-deoxy-4"-[2-fluoro-phenylcarbamoyl]-β-D-cellobiosyl)oxy]-spirostan-11-one | | | |
| >265° C. | 955 (M + Na)+ | $C_{48}H_{69}FN_2O_{15}$ +1 $H_2O$ | calc. C 60.62; H 7.52; N 2.95 found C 60.62; H 7.30; N 2.89 |
| 27) (3β,5α,25R)-3-[(6"-acetamido-6"-deoxy-β-D-cellobiosyl)oxy]-spirostan-11-one | | | |
| >265° C. | 818 (M + Na)+ | $C_{41}H_{65}NO_{14}$ +1 $H_2O$ | calc. C 60.50; H 8.30; N 1.72 found C 60.36; H 7.96; N 1.67 |
| 28) (3β,5α,25R)-3-[(4",6"-Bis[phenyl-thiocarbamoyl]-β-D-cellobiosyl)oxy]-spirostan-11-one | | | |
| 265–268° C. dec | 1047 (M + Na)+ | $C_{53}H_{72}N_2O_{14}S_2$ +1.5 $H_2O$ | calc. C 60.49; H 7.18; N 2.66 found C 60.60; H 7.08; N 2.57 |
| 29) (3β,5α,25R)-3-[(6"-phenyl-thiocarbamoyl-β-D-cellobiosyl)oxy]-spirostan-11-one | | | |
| 252–253° C. dec | 912 (M + Na)+ | HRMS Calc for: $C_{46}H_{67}NO_{14}SNa$ | 912.4180 found 912.4257 |
| 30) (3β,5α,25R)-3-[(6"-deoxy-6"-[3-(2-fluorophenyl)-ureido-]-β-D-cellobiosyl)oxy]-spirostan-11-one | | | |
| 252–254° C. dec | 913 (M + Na)+ | HRMS Calc for: $C_{46}H_{69}FN_2O_{14}Na$ | 914.4550 found 914.4631 |
| 31) (3β,5α,25R)-3-[(4",6"-Bis[pyrrolidin-1-yl carbonyl]-β-D-cellobiosyl)oxy]-spirostan-11-one | | | |
| >265° C. | 971 (M + Na)+ | $C_{49}H_{76}N_2O_{16}$ +1.3 $H_2O$ | calc. C 60.51; H 8.15; N 2.88 found C 60.37; H 8.02; N 3.06 |
| 32) (3β,5α,25R)-3-[(4",6"-Bis[morpholin-1-yl carbonyl]-β-D-cellobiosyl)oxy]-spirostan-11-one | | | |
| >265° C. | 1003 (M + Na)+ | $C_{49}H_{76}N_2O_{18}$ +1.3 $H_2O$ | calc. C 58.59; H 7.89; N 2.79 found C 58.33; H 7.60; N 2.98 |
| 33) (3β,5α,25R)-3-[(6"-[2-fluoro-phenylcarbamoyl]-β-D-lactosyl)oxy]-spirostan-11-one | | | |
| >265° C. | 914 (M + Na)+ | $C_{46}H_{66}NO_{15}$ +1.5$H_2O$ | calc. C 60.12; H 7.57; N 1.52 found C 60.20; H 7.71: N 1.63 |
| 34) (3β,5α,25R)-3-[(4",6"-Bis[3-nitro-phenylcarbamoyl]-β-D-cellobiosyl)oxy]-spirostan-11-one | | | |
| 247–251° C. | 1105 (M + Na)+ | $C_{53}H_{70}N_4O_{20}$ +2 $H_2O$ | calc. C 56.88; H 6.66; N 5.01 found C 56.79; H 6.86; N 5.07 |
| 35) (3β,5α,25R)-3-[(6"-deoxy-6"-(2,6-dichloro-benzamido)-β-D-cellobiosyl)oxy]-spirostan-11-one | | | |
| >265° C. | 949 (M + Na)+ | $C_{46}H_{65}Cl_2NO_{14}$ | calc. C 59.47; H 6.96; N 1.41 found C 59.61; H 7.07; N 1.51 |
| 36) (3β,5α,25R)-3-[(6"-deoxy-6"-benzamido-β-D-cellobiosyl)oxy]-spirostan-11-one | | | |
| >265° C. | 880 (M + Na)+ | $C_{46}H_{67}NO_{14}$ | calc. C 64.21; H 8.11; N 1.69 found C 64.39; H 7.87; N 1.63 |
| 37) (3β,5α,25R)-3-[(6"-deoxy-6"-azido-β-D-cellobiosyl)oxy]-spirostan-11-one | | | |
| 252–254° C. dec | 802 (M + Na)+ | $C_{39}H_{61}N_3O_{13}$ +0.5 $H_2O$ | calc. C 59.38; H 7.92; N 5.33 found C 59.41; H 7.81; N 5.13 |
| 38) (3β,5α,25R)-3-[(6"-deoxy-6"-phenylacetamido-β-D-cellobiosyl)oxy]-spirostan-11-one | | | |
| >265° C. | 894 (M + Na)+ | $C_{47}H_{69}NO_{14}$ +0.4 $H_2O$ | calc. C 64.20; H 8.00; N 1.59 found C 64.04; H 8.00; N 1.72 |
| 39) (3β,5α,25R)-3-[(6"-[α-methoxycarbonyl-benzylcarbamoyl]-β-D-cellobiosyl)oxy]-spirostan-11-one | | | |
| >265° C. | 968 (M + Na)+ | $C_{49}H_{71}NO_{17}$ +0.8 $H_2O$ | calc. C 61.27; H 7.62; N 1.46 found C 61.33; H 7.74; N 1.41 |
| 40) (3β,5α,25R)-3-[(6"-Deoxy-6"-(2-fluoro-phenylacetamido)-β-D-cellobiosyl)oxy]-spirostan-11-one | | | |
| >265° C. | 898 (M + Na)+ | $C_{46}H_{66}FNO_{14}$ +$H_2O$ | calc. C 60.58; H 7.74; N 1.54 found C 60.44; H 7.41; N 1.45 |
| 41) (3β,5α,25R)-3-[(4",6"-Bis(2-fluoro-benzylcarbamoyl)-β-D-cellobiosyl)oxy]-spirostan-11-one | | | |
| 212–213° C. | 1079 (M + Na)+ | HRMS Calc for: $C_{55}H_{74}F_2N_2O_{16}Na$ | 914.4550 |

-continued

| Example) m.p. | Name M.S. | formula | elemental analysis |
|---|---|---|---|
| | | | found 914.4631 |
| 42) (3β,5α,25R)-3-[(4",6"-Bis[2-thienyl-methylcarbamoyl]-β-D-cellobiosyl)oxy]-spirostan-11-one | | | |
| 220–222° C. | 1055 (M + Na)+ | $C_{51}H_{72}N_2O_{16}S_2$ +0.5 $H_2O$ | calc. C 58.77; H 7.06; N 2.69 found C 58.76; H 7.38; N 2.66 |
| 43) (3β,5α,25R)-3-[(4",6"-Bis[furan-2-yl-methylcarbamoyl]-β-D-cellobiosyl)oxy]-spirostan-11-one | | | |
| 244–246° C. | 1023 (M + Na)+ | $C_{51}H_{72}N_2O_{18}$ +0.4 $H_2O$ | calc. C 60.75; H 7.28; N 2.78 found C 60.73; H 7.54; N 2.73 |
| 44) (3β,5α,25R)-3-[(4",6"-Bis[2-ethoxycarbonyl-propylcarbamoyl]-β-D-cellobiosyl)-oxy]-spirostan-11-one | | | |
| 212–214° C. | 1091 (M + Na)+ | $C_{53}H_{84}N_2O_{20}$ +1 $H_2O$ | calc. C 58.55; H 7.97; N 2.58 found C 58.53; H 8.33; N 2.43 |
| 45) (3β,5α,25R)-3-[(4",6"-Bis[ethoxycarbonyl-methylcarbamoyl]-β-D-cellobiosyl)oxy]-spirostan-11-one | | | |
| 246–248° C. | 1035 (M + Na)+ | HRMS Calc for: $C_{49}H_{76}N_2O_{20}Na$ | 1035.4889 found 1035.4906 |
| 46) (3β,5α,25R)-3-[(6"-]1-ethoxycarbonyl-2-(2-thienyl)-ethylcarbamoyl]-β-D-cellobiosyl)oxy]-spirostan-11-one | | | |
| 241–244° C. | 1002 (M + Na)+ | $C_{49}H_{73}NO_{17}S$ +1 $H_2O$ | calc. C 58.96; H 7.57; N 1.40 found C 58.98; H 7.71; N 1.46 |
| 47) (3β,5α,25R)-3-[(6"-[1-ethoxycarbonyl-2-phenyl-ethylcarbamoyl]-β-D-cellobiosyl)oxy]-spirostan-11-one | | | |
| 241–244° C. | 996 (M + Na)+ | $C_{51}H_{75}NO_{17}$ +1.8 $H_2O$ | calc. C 60.86; H 7.87; N 1.39 found C 60.91; H 7.87; N 1.42 |
| 48) (3β,5α,25R)-3-[(4",6"-Bis[1-ethoxycarbonyl-2-phenyl-ethylcarbamoyl]-β-D-cellobiosyl)oxy]-spirostan-11-one | | | |
| 184–185° C. | 1215 (M + Na)+ | $C_{63}H_{88}N_2O_{20}$ +0.8 $H_2O$ | calc. C 62.65; H 7.48; N 2.32 found C 62.75; H 7.82; N 2.23 |
| 49) (3β,5α,25R)-3-[(4",6"-Bis[2-oxo-propylcarbamoyl]-β-D-cellobiosyl)oxy]-spirostan-11-one | | | |
| 258–259° C. dec | 975 (M + Na)+ | $C_{47}H_{72}N_2O_{18}$ +1.2 $H_2O$ | calc. C 57.92; H 7.69; N 2.87 found C 57.94; H 8.00; N 2.59 |
| 50) (3β,5α,12β,25R)-3-[(4",6 -Bis[ethoxycarbonyl-methylcarbamoyl]-β-D-cellobiosyl)oxy]-12-hydroxy-spirostan-11-one | | | |
| 221–222° C. dec | 1051 (M + Na)+ | $C_{49}H_{76}N_2O_{21}$ +1.5 $H_2O$ | calc. C 55.72; H 7.54; N 2.65 found C 55.73; H 7.65; N 2.88 |
| 51) (3β,5α,25R)-3-[(4",6"-Bis[2-methoxycarbonyl-ethylcarbamoyl]-β-D-cellobiosyl)oxy]-spirostan-11-one | | | |
| 234–238° C. | 1035 (M + Na)+ | $C_{49}H_{76}N_2O_{20}$ +1 $H_2O$ | calc. C 57.08; H 7.62; N 2.72 found C 57.25; H 7.82; N 2.56 |
| 52) (3β,5α,25R)-3-[(4",6"-Bis[tetrahydrofuran-2-yl-methylcarbamoyl]-β-D-cellobiosyl)oxy]-spirostan-11-one | | | |
| 259–262° C. | 1031 (M + Na)+ | $C_{51}H_{80}N_2O_{18}$ +1.2 $H_2O$ | calc. C 59.42; H. 8.06; N 2.72 found C 59.44; H 8.31; N 2.49 |
| 53) (3β,5α,25R)-3-[(4",6"-Bis[3-thienyl-methylcarbamoyl]-β-D-cellobiosyl)oxy]-spirostan-11-one | | | |
| 228–230° C. | 1055 (M + Na)+ | $C_{51}H_{72}N_2O_{16}S_2$ +1 $H_2O$ | calc. C 58.27; H 7.09; N 2.66 found C 58.31; H 7.22; N 2.63 |
| 54) (3β,5α,25R)-3-[(4",6"-Bis[2-(2-thienyl)-ethylcarbamoyl]-β-D-cellobiosyl)oxy]-spirostan-11-one | | | |
| 242–245° C. | 1083 (M + Na)+ | $C_{53}H_{76}N_2O_{16}S_2$ +1 $H_2O$ | calc. C 58.98; H 7.28; N 2.60 found C 59.11; H 7.52; N 2.44 |
| 55) (3β,5α,25R)-3-[(4",6"-Bis[3,4-methylenedioxy-benzylcarbamoyl]-β-D-cellobiosyl)oxy]-spirostan-11-one | | | |
| 209–210° C. | 1131 (M + Na)+ | $C_{57}H_{76}N_2O_{20}$ +1.2 $H_2O$ | calc. C 60.54; H 6.99; N 2.48 found C 60.68; H 7.30; N 2.48 |
| 56) (3β,5α,25R)-3-[(4", 6"-Bis[2-trifluoromethyl-benzylcarbamoyl]-β-D cellobiosyl)oxy]-spirostan-11-one | | | |
| 230–240° C. | 1179 (M + Na)+ | $C_{57}H_{74}F_6N_2O_{16}$ +0.7 $H_2O$ | calc. C 58.52; H 6.50; N 2.39 found C 58.56; H 6.45; N 2.45 |
| 57) (3β,5α,25R)-3-[(4",6"-Bis[5-methyl-2-thienyl-methylcarbamoyl]-β-D-cellobiosyl)oxy]-spirostan-11-one | | | |
| 214–215° C. | 1083 (M + Na)+ | $C_{53}H_{76}N_2O_{16}S_2$ +0.5 $H_2O$ | calc. C 59.48; H 7.25; N 2.62 found C 59.46; H 7.29; N 2.73 |
| 58) (3β,5α,25R)-3-[(4",6"-Bis[4-bromo-2-thienyl-methylcarbamoyl]-β-D-cellobiosyl)oxy]-spirostan-11-one | | | |
| 211–213° C. | 1213 (M + Na)+ | $C_{51}H_{70}Br_2N_2O_{16}S_2$ | calc. C 51.37; H 5.87; N 2.41 found C 51.43; H 5.92; N 2.35 |
| 59) (3β,5α,25R)-3-[(4",6"-Bis[5-bromo-2-thienyl-methylcarbamoyl]-β-D-cellobiosyl)oxy]-spirostan-11-one | | | |
| 226–227° C. | 1213 (M + Na)+ | $C_{51}H_{70}Br_2N_2O_{16}S_2$ +0.05 $H_2O$ | calc. C 51.04; H 5.96; N 2.33 found C 51.03; H 6.35; N 2.40 |
| 60) (3β,5α,25R)-3-[(4",6"-Bis[2-thienylcarbamoyl]-β-D-cellobiosyl)oxy]-spirostan-11-one | | | |
| 261–262° C. dec | 1027 (M + Na)+ | $C_{49}H_{68}N_2O_{16}S_2$ +2 $H_2O$ | calc. C 56.52; H 6.97; N 2.69 found C 56.48; H 7.13; N 2.74 |

-continued

| Example) m.p. | Name M.S. | formula | elemental analysis |
|---|---|---|---|
| 61) (3β,5α,12β,25R)-3-[(4",6"-Bis[3-thienyl-methylcarbamoyl]-β-D-cellobiosyl)oxy]-12-hydroxy-spirostan-11-one | | | |
| 238–239° C. | 1071 (M + Na)⁺ | $C_{51}H_{72}N_2O_{17}S_2$ +1.5 $H_2O$ | calc. C 56.91; H 7.02; N 2.60 found C 56.85; H 6.86; N 2.65 |
| 62) (3β,5α,25R)-3-[(4",6"-Bis[2-methoxycarbonyl-2-methyl-propylcarbamoyl]-β-D-cellobiosyl)oxy]-spirostan-11-one | | | |
| 239–240° C. | 1091 (M + Na)⁺ | $C_{53}H_{84}N_2O_{20}$ +1.7 $H_2O$ | calc. C 57.88; H 8.01; N 2.55 found C 57.83; H 8.11; N 2.66 |
| 63) (3β,5α,25R)-3-[(4",6"-Bis[2-oxo-2-(2-thienyl)-ethylcarbamoyl]-β-D-cellobiosyl)oxy]-spirostan-11-one | | | |
| 270–271° C. dec | 1111 (M + Na)⁺ | $C_{53}H_{72}N_2O_{18}S_2$ +1 $H_2O$ | calc. C 57.49; H 6.74; N 2.53 found C 57.37; H 6.73; N 2.57 |
| 64) (3β,5α,12β,25R)-3-[(4",6"-Bis[2-methoxycarbonyl-ethylcarbamoy]-β-D-cellobiosyl)oxy]-12-hydroxy-spirostan-11-one | | | |
| 232–236° C. dec | 1051 (M + Na)⁺ | $C_{49}H_{76}N_2O_{21}$ +1.7 $H_2O$ | calc. C 55.53; H 7.55; N 2.64 found C 55.58; H 7.62; N 2.60 |
| 65) (3β,5α,25R)-3-[(4",6"-Bis[thiazol-2-yl-methylcarbamoyl]-β-D-cellobiosyl)oxy]-spirostan-11-one | | | |
| 251–252° C. | 1057 (M + Na)⁺ | $C_{47}H_{70}N_4O_{16}S_2$ +1.3 $H_2O$ | calc. C 55.59; H 6.91; N 5.29 found C 55.74; H 7.16; N 4.97 |
| 66) (3β,5α,25R)-3-[(4",6"-Bis[benzylcarbamoyl]-β-D-cellobiosyl)oxy]-spirostan-11-one | | | |
| 254–255° C. dec | 1043 (M + Na)⁺ | $C_{55}H_{76}N_2O_{16}$ +1.5 $H_2O$ | calc. C 63.02; H 7.60; N 2.67 found C 63.00; H 7.61; N 2.79 |
| 67) (3β,5α,25R)-3-[(4",6"-Bis[5-trifluoromethyl-benzothiazol-2-yl-methyl carbamoyl]-β-D-cellobiosyl)oxy]-spirostan-11-one | | | |
| >265° C. | 1293 (M + Na)⁺ | $C_{59}H_{72}F_6N_4O_{16}S_2$ +1.8 $H_2O$ | calc. C 54.35; H 5.84; N 4.30 found C 54.16; H 5.96; N 4.28 |
| 68) (3β,5α,25R)-3-[(4",6"-Bis[4-methoxy-benzylcarbamoyl]-β-D-cellobiosyl)oxy]-spirostan-11-one | | | |
| 222–224° C. | 1103 (M + Na)⁺ | $C_{57}H_{80}N_2O_{18}$ +2.8 $H_2O$ | calc. C 60.50; H 7.62; N 2.48 found C 60.38; H 7.51; N 2.63 |
| 69) (3β,5α,25R)-3-[(4",6"-Bis[2-(2-fluorophenyl)ethylcarbamoyl]-β-D-cellobiosyl)oxy]-spirostan-11-one | | | |
| 221–223° C. | 1107 (M + Na)⁺ | $C_{57}H_{78}F_2N_2O_{16}$ +1.7 $H_2O$ | calc. C 61.35; H 7.35; N 2.51 found C 61.37; H 7.36; N 2.69 |
| 70) (3β,5α,12 cellobiosyl)oxy]-12-hydroxy-spirostan-11-one | | | |
| 229–232° C. dec | 1073 (M + Na)⁺ | $C_{49}H_{70}N_4O_{17}S_2$ +2.2 $H_2O$ | calc. C 53.95; H 6.87; N 5.14 found C 53.90; H 6.85; N 5.03 |
| 71) (3β,5α,25R)-3-[(4",6"-Bis[3-methyl-isoxazol-5-yl-methylcarbamoyl]-β-D-cellobiosyl)oxy]-spirostan-11-one | | | |
| 242–244° C. | 1053 (M + Na)⁺ | $C_{51}H_{74}N_4O_{18}$ +2.2 $H_2O$ | calc. C 57.21; H 7.38: N 5.23 found C 57.06; H 7.60; N 5.41 |
| 72) (3β,5α,25R)-3-[(4",6"-Bis[2-methoxycarbonyl-butylcarbamoyl]-β-D-cellobiosyl)oxy]-spirostan-11-one | | | |
| 216–217° C. | 1091 (M + Na)⁺ | $C_{53}H_{84}N_2O_{20}$ +2 $H_2O$ | calc. C 57.57; H 8.02; N2.53 found C 57.45; H 8.31; N 2.83 |
| 73) (3β,5α,25R)-3-[(6"-bromo-6"-deoxy-β-D-cellobiosyl)oxy]-spirostan-11-one | | | |
| 169–170° C. (dec) | 828 (M + Na)⁺ | $C_{39}H_{61}BrO_{13}$ +1.7 $H_2O$ | calc. C 55.21; H 7.65 found C 55.59; H 8.03 |
| 74) (3β,5α,25R)-3-[(6"-deoxy-β-D-cellobiosyl)oxy]-spirostan-11-one | | | |
| 257–260° C. (dec) | 760 (M + Na)⁺ | $C_{39}H_{62}O_{13}$ +2.6 $H_2O$ | calc. C 59.62; H 8.62 found C 59.58; H 8.97 |
| 75) (3β,5α,25R)-3-[(6"-deoxy-4"-[2-fluoro-phenylcarbamoyl]-β-D-cellobiosyl)oxy] spirostan-11-one | | | |
| 262–265° C. (dec) | 898 (M + Na)⁺ | $C_{46}H_{66}FNO_{14}$ +0.5$H_2O$ | calc. C 62.43; H 7.63; N 1.58 found C 62.13; H 8.02; N 1.89 |
| 76) (3β,5α,11β,25R)-3-[(4",6"-Bis[2-fluoro-phenylcarbamoyl]-β-D-cellobiosyl)oxy]-11-hydroxy-spirostane | | | |
| 268–270° C. | 1053 (M + Na)⁺ | HRMS calc for: $C_{53}H_{72}F_2N_2O_{16}$ | 1053.4748 found: 1053.47628 |
| 77) (3β,5α,25R)-3-[(4",6"-Bis[pyridin-3-yl-methylcarbamoyl]-β-D-cellobiosyl)oxy]-spirostan-11-one | | | |
| 234–237° C. | 1045 (M + Na)⁺ | $C_{53}H_{74}N_4O_{16}$ +3 $H_2O$ | calc. C 59.09; H 7.49; N 5.20 found C 59.16; H 7.83; N 5.26 |

EXAMPLE 78

(3β,5α,25R)-3[(4",6"-bis[2-fluoro-phenylcarbamoyl]-β-D-cellobiosyl)oxy] spirostan-11-one Deacetylation Using Potassium Cyanide To a solution of (3β,5α,25R)-3-[(4",6"-bis-[2-fluoro-phenylcarbamoyl]-penta acetyl-β-D-cellobiosyl)oxy]-spirostan-11-one (0.48 g, 0.39 mmol) in tetrahydrofuran (3 mL) and methanol (3 mL), potassium cyanide (38 mg, 0.58 mmol) was added. The reaction was stirred at room temperature under nitrogen atmosphere for 4 hours. Upon completion, methanol was added and the reaction mixture was concentrated in vacuo. Methanol, then water was added to the residual material, causing a precipitate to form. The precipitate was filtered, washed with water and dried in a vacuum oven. The crude product was purified via flash chromatography (2% methanol: chloroform). The isolated material was concentrated in vacuo, then triturated with methanol and water. The product was then filtered, washed with water and oven-dried to afford 33 mg (8.3% yield) of the title compound. $^1$HNMR (250 MHz; DMSO-$d_6$) δ 9.4 (s, 1H); 9.3 (s, 1H); 7.7–7.05 (m, 8H); 5.5 (d, 1H, J=7 Hz); 5.45 (d, 1H, J=7 Hz); 5.0 (d, 1H, J=7 Hz); 4.7–2.9 (m, 20H); 2.55–1.1 (m, 25H); 0.95 (s, 3H); 0.85 (d, 3H, J=8 Hz); 0.7 (d, 3H, J=8 Hz); 0.6 (s, 3H). FAB MS: 1051 (M+Na)$^+$; Analysis calculated for $C_{53}H_{70}F_2N_2O_{16}$–1 $H_2O$: C 60.79, H 6.93, N 2.67; found: C 60.63, H 6.72, N 2.83; m.p.>265° C.

EXAMPLES 79–83

The following compounds were prepared from the appropriate starting material in an analogous manner using the above procedures.

| Example) m.p. | Name M.S. | formula | | elemental analysis |
|---|---|---|---|---|
| 79) (3β,5α,25R)-3-[(4", 6"-Bis[2,4-difluoro-phenylcarbamoyl]-β-D-cellobiosyl)oxy]-spirostan-11-one | | | | |
| >265° C. (dec) | 1087(M + Na)$^+$ | $C_{53}H_{68}F_4N_2O_{16}$ +1 $H_2O$ | calc. found | C 58.77; H 6.51; N 2.59 C 58.79; H 6.47; N 2.49 |
| 80) (3β,5α,25R)-3-[(4",6"-Bis[2,6-dichloro-phenylcarbamoyl]-β-D-cellobiosyl)oxy]-spirostan-11-one | | | | |
| 262–264° C. | 1153(M + Na)$^+$ | HRMS calc. for $C_{53}H_{68}Cl_4N_2O_{16}$Na | found | 1151.3221 1151.3216 |
| 81) (3β,5α,25R)-3-[(4",6"-Bis[2-chloro-phenylcarbamoyl]-β-D-cellobiosyl)oxy]-spirostan-11-one | | | | |
| 247–250° | 1085(M + Na)$^+$ | $C_{53}H_{70}Cl_2N_2O_{16}$ +1.0 $H_2O$ | calc. found | C 58.94; H 6.72; N 2.59 C 58.70; H 6.65; N 2.70 |
| 82) (3β,5α,25R)-3-[(4",6"-Bis[2-methyl-phenylcarbamoyl]-β-D-cellobiosyl)oxy]-spirostan-11-one | | | | |
| 249–250° | 1043(M + Na)$^+$ | $C_{55}H_{76}N_2O_{16}$ + 1.0 $H_2O$ | calc. found | C 63.57; H 7.56; N. 2.69 C 63.39; H 7.46; N 2.99 |
| 83) (3β, 5α,25R)-3-[(4",6"-Bis[phenylcarbamoyl]-β-D-cellobiosyl)oxy]-spirostan-11-one | | | | |
| >265° C. | 1014(M + Na)$^+$ | $C_{53}H_{72}N_2O_{16}$ +1.5 $H_2O$ | calc. found | C 62.40; H 7.41; N 2.75 C 62.48; H 7.22; N 3.06 |

EXAMPLE 84

(3β,5α,25R)-3-[(6',6"-Bis[2,4-dichloro-phenylcarbamoyl]-β-D-cellobiosyl)oxy]-spirostan-11-one Carbamoylation A mixture of (3β,5α,25R)-3-[(β-D-cellobiosyl)oxy] spirostan-11-one (0.50 g, 0.66 mmol), pyridine (3 mL) and 4A molecular sieves (0.50 g) was stirred for 10 minutes at room temperature under nitrogen atmosphere. The reaction was then cooled to −40° C. and 2,4-dichlorophenyl isocyanate was added. The reaction mixture was gradually warmed to room temperature and stirred for 1.5 hours. Upon completion, the reaction was quenched with methanol. The quenched mixture was concentrated in vacuo twice with toluene in order to remove the pyridine. The crude material was purified via flash chromatography (2% to 10% methanol:chloroform). The first product isolated was the 6',6"-dicarbamate which was concentrated in vacuo, triturated with methanol/water, filtered and washed with water to afford 230 mg (40% yield) of the title compound. FAB MS: 1129 (M+H)$^+$; m.p. 182° C.

EXAMPLE 85

(3β,5α,25R)-3-[(6"-[2,4-dichloro-phenylcarbamoyl]-β-D-cellobiosyl)oxy]-spirostan-11-one Further elution of the column in Example 84 gave the 6"-monocarbamate, 35 mg (6% yield). FAB MS: 942 (M+H)$^+$; Analysis calculated for $C_{46}H_{65}Cl_2NO_{15}$+0.5 $H_2O$: C 58.04, H 6.99, N 1.47; found: C 58.01, H 6.86, N 1.48; m.p. 241–242° C.

EXAMPLES 86–119

The following compounds were prepared from the appropriate starting material and isocyanate or acid chloride in an analogous manner using the above procedures.

| Example) m.p. | Name M.S. | formula | | elemental analysis |
|---|---|---|---|---|
| 86) (3β,5α,25R)-3-[(6', 6"-Bis[4-chloro-phenylcarbamoyl]-β-D-cellobiosyl)oxy] spirostan-11-one | | | | |
| 233° C. (dec) | 1061(M + H)$^+$ | $C_{53}H_{70}Cl_2N_2O_{16}$ +1.2 $H_2O$ | calc. found | C 58.74; H 6.73; N 2.58 C 58.55; H 6.54; N 2.66 |

-continued

| Example) m.p. | Name M.S. | formula | elemental analysis |
|---|---|---|---|
| 87) (3β,5α,25R)-3-[(6',6"-Bis[2,6-dichloro-phenylcarbamoyl]-β-D-cellobiosyl)oxy]spirostan-11-one | | | |
| 260–265° C. (dec) | 1131 (M + H)+ | HRMS calc. for $C_{53}H_{68}N_2Cl_4O_{16}Na$ | 1151.3221 found 1151.3206 |
| 88) (3β,5α,25R)-3-[(6',6"-Bis [benzylcarbamoyl]-β-D-cellobiosyl)oxy]-spirostan-11-one | | | |
| 164–165° C. | 1043(M + Na)+ | HRMS calc. for $C_{55}H_{76}N_2O_{16}Na$ | 1043.5093 found: 1043.5178 |
| 89) (3β,5α,25R)-3-[(6',6"-Bis [2-fluoro-phenylcarbamoyl]-β-D-cellobiosyl)oxy]-spirostan-11-one | | | |
| 249° C. | 1051(M + Na)+ | $C_{53}H_{70}F_2N_2O_{16}$ +2 $H_2O$ | calc. C 59.76; H 7.02; N 2.63 found C 59.91; H 6.93; N 2.57 |
| 90) (3β,5α,25R)-3-[(6', 6"-Bis[2-chloro-phenylcarbamoyl]-β-D-cellobiosyl)oxy]-spirostan-11-one | | | |
| >265° C. | 1083(M + Na)+ | $C_{53}H_{70}Cl_2N_2O_{16}$ +1.0 $H_2O$ | calc. C 58.94; H 6.72; N 2.59 found C 58.66; H 6.58; N 2.74 |
| 91) (3β,5α,25R)-3-[(6',6"-Bis[2-methyl-phenylcarbamoyl]-β-D-cellobiosyl)oxy]-spirostan-11-one | | | |
| 205–208° C. | 1043(M + Na)+ | $C_{55}H_{76}N_2O_{16}$ +1.0 $H_2O$ | calc. C 63.57; H 7.56; N 2.69 found C 63.51; H 7.41; N 2.77 |
| 92) (3β,5α,25R)-3-[(6"-[4-chloro-phenylcarbamoyl]-β-D-cellobiosyl)oxy]-spirostan-11-one | | | |
| >265° C. | 930(M + Na)+ | $C_{46}H_{66}ClNO_{15}$ | calc. C 60.82; H 7.32; N 1.54 found C 60.71; H 7.24; N 1.33 |
| 93) (3β,5α, 25R)-3-[(6'-[4-chloro-phenylcarbamoyl]-β-D-cellobiosyl)oxy]-spirostan-11-one | | | |
| >255° C. | 908(M + H)+ 930(M + Na)+ | $C_{46}H_{66}ClNO_{15}$ +1.0 $H_2O$ | calc. C 59.63; H 7.40; N 1.51 found C 59.54; H 7.24; N 1.33 |
| 94) (3β, 5α,25R)-3-[(6"-[2,6-dichloro-phenylcarbamoyl]-β-D-cellobiosyl)oxy]-spirostan-11-one | | | |
| 253–254° C. | 964(M + Na)+ | $C_{46}H_{65}Cl_2NO_{15}$ | calc. C 58.59; H 6.59; N 1.48 found C 58.55; H 6.84; N 1.29 |
| 95) (3β,5α,25R)-3-[(6"-[2,4-difluoro-phenylcarbamoyl]-β-D-cellobiosyl)oxy]-spirostan-11-one | | | |
| >265° C. | 910(M + H)+ | $C_{46}H_{65}F_2NO_{15}$ | calc. C 60.71; H 7.20; N 1.54 found C 60.36; H 6.89; N 1.28 |
| 96) (3β,5α,25R)-3-[(6"-[2-fluoro-phenylcarbamoyl]-β-D-cellobiosyl)oxy]-spirostan-11-one | | | |
| >265° C. | 914(M + Na)+ | $C_{46}H_{66}FNO_{15}$ +1.0 $H_2O$ | calc. C 60.71; H 7.53; N 1.54 found C 60.92; H 7.45; N 1.76 |
| 97) (3β,5α,25R)-3-[(6"-[benzylcarbamoyl]-β-D-cellobiosyl)oxy]-spirostan-11-one | | | |
| >260° C. | 910(M + Na)+ | HRMS calc. for $C_{47}H_{69}NO_{15}Na$ | 910.4565 found 910.4633 |
| 98) (3β,5α,25R)-3-[(6"-[2-chloro-phenylcarbamoyl]-β-D-cellobiosyl)oxy]-spirostan-11-one | | | |
| 264–265° C. | 930(M + Na)+ | $C_{46}H_{66}ClNO_{15}$ +1.0 $H_2O$ | calc. C 60.69; H 7.33; N 1.53 found C 60.40; H 7.31; N 1.70 |
| 99) (3β,5α,25R)-3-[(6"-[2-methyl-phenylcarbamoyl]-β-D-cellobiosyl)oxy]-spirostan-11-one | | | |
| 254–256°C. | 910(M + Na)+ | $C_{47}H_{69}NO_{15}$ +1.0 $H_2O$ | calc. C 62.30; H 7.90; N 1.54 found C 62.17; H 7.87; N 1.61 |
| 100) (3β,5α,25R)-3-[(6', 6"-Bis[2,6-dichloro-benzoyl]-β-D-[lactosyl]oxy]-spirostan-11-one | | | |
| 255° C. (dec) | 1099(M + H)+ 1121(M + Na)+ | $C_{53}H_{66}Cl_4O_{16}$ | calc. C 57.82; H 6.04 found C 57.49; H 6.01 |
| 101) (3β,5α,25R)-3-[(6',6"-Bis[4-fluoro-benzoyl]-β-D-cellobiosyl)oxy]-spirostan-11-one | | | |
| 173–174° C. | 999(M + H)+ | $C_{53}H_{68}F_2O_{16}$ +1.2 $H_2O$ | calc. C 62.37; H 6.95 found C 62.13; H 6.92 |
| 102) (3β,5α,25R)-3-[(6',6"-Bis[furan-2-carbonyl]-β-D-cellobiosyl)oxy]-spirostan-11-one | | | |
| 248–250° C. (dec) | 943(M + H)+ 964(M + Na)+ | $C_{49}H_{66}O_{18}$ +0.75 $H_2O$ | calc. C 61.53; H 7.11 found C 61.45; H 7.01 |
| 103) (3β,5α,25R)-3-[(6',6"-Bis [2,6-dimethoxy-benzoyl]-β-D-cellobiosyl)oxy]-spirostan-11-one | | | |
| 257–258° C. | 1105(M + Na)+ | $C_{57}H_{78}O_{20}$ +2.0 $H_2O$ | calc. C 61.17; H 7.38 found C 61.10; H 7.19 |
| 104) (3β,5α,25R)-3-[(6"-[2,6-dichloro-benzoyl]-β-D-cellobiosyl)oxy]-spirostan-11-one | | | |
| 269–271° C. (dec) | 926(M + H)+ | $C_{46}H_{64}Cl_2O_{15}$ | calc. C 59.54; H 6.95 found C 59.39; H 6.74 |
| 105) (3β,5α,25R)-3-[(6"-[2,6-difluoro-benzoyl]-β-D-cellobiosyl)oxy]-spirostan-11-one | | | |
| 272–274° C. | 895(M + H)+ 917(M + Na)+ | $C_{46}H_{64}F_2O_{15}$ | calc. C 61.73; H 7.21 found C 61.58; H 6.94 |
| 106) (3β,5α,25R)-3-[(6"-[4-chloro-benzoyl]-β-D-cellobiosyl)oxy]-spirostan-11-one | | | |
| 254–255° C. | 893(M + H)+ | $C_{46}H_{65}ClO_{15}$ | calc. C 61.84; H 7.33 found C 61.47; H 7.09 |
| 107) (3β,5α,25R)-3-[(6"-[4-fluoro-benzoyl]-β-D-cellobiosyl)oxy]-spirostan-11-one | | | |
| 262–265° C. | 877(M + H)+ | $C_{46}H_{65}FO_{15}$ | calc. C 62.36; H 7.51 |

| Example) m.p. | Name M.S. | formula | elemental analysis |
|---|---|---|---|
| | | +0.5 $H_2O$ | found C 62.55; H 7.26 |
| 108) (3β,5α,25R)-3-[(6"-[2,6-dichloro-benzoyl]-β-D-lactosyl)oxy]-spirostan-11-one | | | |
| 247–248° C. | 927(M + H)$^+$ 949(M + Na)$^+$ | $C_{46}H_{64}Cl_2O_{15}$ | calc. C 59.54; H 6.95 found C 59.35; H 6.70 |
| 109) (3β,5α,25R)-3-[(6"-[furan-2-carbonyl]-β-D-cellobiosyl)oxy]-spirostan-11-one | | | |
| >265° C. | 849(M + H)$^+$ | $C_{44}H_{64}O_{16}$ | calc. C 62.25; H 7.60 found C 62.22; H 7.61 |
| 110) (3β,5α,25R)-3-[(6"-[2,4-difluoro-benzoyl]-β-D-cellobiosyl)oxy]-spirostan-11-one | | | |
| 261–262° C. | 895(M + H)$^+$ | $C_{46}H_{64}F_2O_{15}$ +0.8 $H_2O$ | calc. C 60.75; H 7.27 found C 60.74; H 6.89 |
| 111) (3β,5α,25R)-3-[(6"- [2,6-dimethoxy-benzoyl]-β-D-cellobiosyl)oxy]-spirostan-11-one | | | |
| 263–265° C. | 941(M + Na)$^+$ | $C_{48}H_{70}O_{17}$ | calc. C 62.73; H 7.68 found C 62.83; H 7.58 |
| 112) (3β,5α,25R)-3-[(6',6"-Bis[2,6-difluoro-benzoyl]-β-D-cellobiosyl)oxy]-spirostan-11-one | | | |
| 230° C. (dec) | 1035(M + H)$^+$ 1057(M + Na)$^+$ | $C_{57}H_{66}F_4O_{16}$ +1.5 $H_2O$ | calc. C 59.74; H 6.55 found C 59.70; H 6.45 |
| 113) (3β,5α,25R)-3-[(6',6"-Bis[2-methoxycarbonyl-phenylcarbamoyl]-β-D-cellobiosyl)oxy]-spirostan-11-one | | | |
| 249–251° C. dec | 1131 (M + Na)$^+$ | $C_{57}H_{76}N_2O_{20}$ +2$H_2O$ | calc. C 59.78; H 7.04; N 2.45 found C 59.54; H 7.00; N 2.55 |
| 114) (3β,5α,25R)-3-[(6"-[2-methoxycarbonyl-phenylcarbamoyl]-β-D-cellobiosyl)oxy]-spirostan-11-one | | | |
| >265° C. | 954 (M + Na)$^+$ | $C_{48}H_{69}NO_{17}$ +2.6 $H_2O$ | calc. C 58.89; H 7.64; N 1.43 found C 59.23; H 8.03; N 1.12 |
| 115) (3β,5α,25R)-3-[(6"-[2-phenyl-ethylcarbamoyl]-β-D-cellobiosyl)oxy]-spirostan-11-one | | | |
| >265°C. | 924 (M + Na)$^+$ | $C_{48}H_{71}NO_{15}$ +0.7 $H_2O$ | calc. C 63.03; H 7.98; N 1.53 found C 63.01; H 8.15; N 1.33 |
| 116) (3β,5α,25R)-3-[(6',6"-Bis[2-phenyl-ethylcarbamoyl]-β-D-cellobiosyl)oxy]-spirostan-11-one | | | |
| >235–237° C. dec | 1071 (M + Na)$^+$ | $C_{57}H_{80}N_2O_{16}$ +2.2 $H_2O$ | calc. C 62.87; H 7.81; N 2.57 found C 62.94; H 8.06; N 2.44 |
| 117) (3β,5α,25R)-3-[(6'-[2-fluoro-phenylcarbamoyl]-β-D-cellobiosyl)oxy]-spirostan 11-one | | | |
| 126–127° C. | 914 (M + Na)$^+$ | $C_{46}H_{66}FNO_{15}$ +4 $H_2O$ | calc. C 57.31; H 7.74; N 1.45 found C 57.30; H 7.59; N 1.42 |
| 118) (3β,5α,25R)-3-[(6"-[allylcarbamoyl]-β-D-cellobiosyl)oxy]-spirostan-11-one | | | |
| >265° C. | 860 (M + Na)$^+$ | $C_{43}H_{67}NO_{15}$ +2 $H_2O$ | calc. C 59.09; H 8.19; N 1.60 found C 59.07; H 8.16; N 1.50 |
| 119) (3β,5α,25R)-3-[(6"-[2-bromo-phenylcarbamoyl]-β-D-cellobiosyl)oxy]-spirostan-11-one | | | |
| 253–255° C. | 974 (M + Na)$^+$ | $C_{46}H_{66}BrNO_{15}$ +1 $H_2O$ | calc. C 56.90; H 7.06; N 1.44 found C 56.97; H 7.16; N 1.59 |

Preparation A1

(3β,5α,25R)-3-[(4",6"-Bis[2-oxo-propylcarbamoyl]-2',2",3',3",6'-penta-acetyl-β-D-cellobiosyl)oxy]-spirostan-11-one PCC Oxidation Pyridinium chlorochromate (1.0 g, 4.7 mmol) was added to a solution of (3β,5α,25R)-3-[(4",6"-bis [2-hydroxy-propylcarbamoyl]-2',2",3',3",6'-penta-acetyl-β-D-cellobiosyl)oxy]-spirostan-11-one (482 mg, 0.413 mmol) in methylene chloride (10 mL) containing dry Celite filter aid (1.5 g). After 5 h at room temperature an additional 350 mg of pyridinium chlorochromate was added and the reaction stirred overnight. The mixture was diluted with ether (20 mL) and the mixture was filtered through silica gel (eluting with ethyl acetate). The filtrate was concentrated and the residue was purified by flash chromatography (3% methanol/methylene chloride) to give 400 mg of the title compound as a colorless foam. $^1$H NMR (250 MHz, $CDCl_3$) δ 6.5 (bt, 1H, J=6.0 Hz); 6.0 (bt, 1H, J=6.0 Hz); 5.15 (m, 2H); 4.9 m (3H); 4.6–3.5 (m, 12H); 3.4 (dd, 1H, J=8.0, 8.0 Hz); 2.45 (m, 1H); 2.22 (s, 2H); 2.2 (s, 3H); 2.12 (s, 3H); 2.08 (s, 6H); 2.05 (s, 6H); 2.0 (s, 3H); 2.0–1.0 (m, 26H); 1.0 (s, 3H); 0.9 (d, 3H, J=7.0 Hz); 0.75 (d, 3H, J=7.0 Hz); 0.65 (s, 3H).

In an analogous manner, the following compound, Preparation A2 was prepared from the appropriate starting material using the above general procedure.

Preparation A2

(3β,5α,25R)-3-[(4",6"-Bis[2-oxo-2-(2-thienyl)-ethylcarbamoyl]-2',2",3',3",6'-penta-acetyl-β-D-cellobiosyl)oxy]-spirostan-11-one Preparation B1

(3β,5α, 25R)-3-[(4"-[2-fluoro-phenylcarbamoyl]-6"-triisopropylsilyl-β-D-cellobiosyl)oxy]-spirostan-11-one Deacylation of Silyl Substituted Compounds Sodium methoxide (21 mg) was added to a solution of (3β,5α,25R)-3-[(4"-[2-fluoro-phenylcarbamoyl]-2',2",3',3",6'-pentaacetyl-6"-triisopropylsilyl-β-D-cellobiosyl)oxy]-spirostan-11-one (668 mg, 0.53 mmol) in THF (1 mL) and methanol (2 mL). After 1 h, the mixture was concentrated and the residue was purified by flash chromatography (1–3% methanol/chloroform) to afford 322 mg product as a colorless foam (58%). $^1$H NMR (250 MHz, $CDCl_3$) δ 8.0 (bs, 1H); 7.05 (m, 4H); 4.88 (dd, 1H J=9.0, 9.0 Hz); 4.48 (m, 3H); 4.3 (s, 1H); 3.9–3.3 (m, 16H); 2.8 (t, 1H, J=6.0 Hz); 2.55 (d, 1H, J=1.5 Hz); 2.5 (m, 1H); 2.25 (s, 2H); 2.1–1.0 (m, 46H); 0.9 (d, 3H, J=7.0 Hz); 0.8 (d, 3H, J=7.0 Hz); 0.7 (s, 3H).

Preparation C1

(3β,5α,25R)-3-[(6',6"-Bis-[phenylcarbamoyl]-pentaacetyl-β-D-cellobiosyl)oxy]-spirostan-11-one Carbamoylation or Acylation A mixture of (3β,5α,25R)-3-[(2',2",3',3",4'-pentaacetyl-β-D-cellobiosyl)oxy] spirostan-11-one (0.50 g, 0.52 mmol), methylene chloride (5 mL), triethylamine (0.50 mL, 3.62 mmol) and diethylaminopyridine (0.10 g) was cooled to 0° C. under nitrogen atmosphere. Phenyl isocyanate (0.34 mL, 3.12 mmol) was added and the reaction was stirred at 0° C. for 15 minutes, then at room temperature for 30 minutes. Upon completion, the reaction was quenched with methanol. The quenched mixture was diluted with ethyl acetate, washed with water (1×), 1 N hydrochloric acid solution (3×), saturated sodium bicarbonate solution (2×) and brine (1×), dried over sodium sulfate, filtered and concentrated in vacuo. The residual material was triturated with hexanes, filtered, washed with hexanes and dried to afford >100% yield of the crude titled compound. $^1$HNMR (250 MHz, CDCl$_3$) δ 7.55–7.0 (m, 1OH); 6.85 (s, 1H); 6.65 (s, 1H); 5.3–3.52 (m, 17H); 3.45 (t, 1H, J=10 Hz); 2.5–1.05 (m, 40H); 1.0 (s, 3H); 0.95 (d, 3H, J=8 Hz); 0.8 (d, 3H, J=8 Hz); 0.7 (s, 3H).

In an analogous manner the following compounds, Preparations C2–C30, were prepared from the appropriate starting material using the above general procedure.

Preparation C2

(3β,5α,25R)-3-[(6',6"-Bis[2,4-difluoro-phenylcarbamoyl]-pentaacetyl-β-D-cellobiosyl)-oxy] spirostan-11-one Preparation C3

3β,5α,25R)-3-[(6"-[2,4-difluoro-phenylcarbamoyl]-pentaacetyl-β-D-cellobiosyl)oxy]spirostan-11-one Preparation C4

(3β,5α,25R)-3-[(4",6"-Bis[2,4-difluoro-phenylcarbamoyl]-pentaacetyl-β-D-cellobiosyl)oxy] spirostan-11-one Preparation C5

(3β,5α,25R)-3-[(4",6"-Bis[2,6-dichloro-phenylcarbamoyl]-pentaacetyl-β-D-cellobiosyl)oxy] spirostan-11one Preparation C6

(3β,5α,25R)-3-[(4",6"-Bis[2-chloro-phenylcarbamoyl]-pentaacetyl-β-D-cellobiosyl)oxy]spirostan-11-one Preparation C7

(3β,5α,25R)-3-[(4",6"-Bis[2-methyl-phenylcarbamoyl]-pentaacetyl -β-D-cellobiosyl)oxy]spirostan-11-one Preparation C8

(3β,5α,25R)-3-[(4",6"-Bis[phenylcarbamoyl]-pentaacetyl-β-D-cellobiosyl)oxy]spirostan-11-one Preparation C9

(3β,5α,25R)-3-[(4",6"-Bis[2-methoxy-phenylcarbamoyl]-pentaacetyl-β-D-cellobiosyl)oxy] spirostan-11-one Preparation C10

(3β,5α,25R)-3-[(6"-[2-methoxy-phenylcarbamoyl]-hexaacetyl-β-D-cellobiosyl)oxy]spirostan-11-one Preparation C11

(3β,5α,25R)-3-[(4"-[2"fluoro-phenylcarbamoyl]-hexaacetyl-β-D-cellobiosyl)oxy]spirostan-11-one Preparation C12

(3β,5α,25R)-3-[(4",6"-Bis[2,6-dimethyl-phenylcarbamoyl]-pentaacetyl-β-D-cellobiosyl)oxy] spirostan-11-one Preparation C13

(3β,5α,25R)-3-[(4",6"-Bis[2,5-difluoro-phenylcarbamoyl]-pentaacetyl-β-D-cellobiosyl)oxy] spirostan-11-one Preparation C14

(3β,5α,12β,25R)-3-[(4",6"-Bis[2-fluoro-phenylcarbamoyl]-pentaacetyl-β-D-cellobiosyl)oxy]12-acetoxy-spirostan-11-one Preparation C15

(3β,5α,25R)-3-[(4",6"-Bis [2-methoxycarbonyl-phenylcarbamoyl]-2',2",3',3",6'-penta-acetyl-β-D-cellobiosyl)oxy]-spirostan-11-one Preparation C16

(3β,5α,25R)-3-[(6"-[4-phenoxy-phenylcarbamoyl]-2',2",3',3",4",6'-hexa-acetyl -β-D-cellobiosyl)oxy]-spirostan-11-one Preparation C17

(3β,5α,25R)-3-[(4",6"-Bis[allylcarbamoyl]-2',2",3',3",6'-penta-acetyl -β-D-cellobiosyl)oxy]-spirostan-11-one Preparation C18

(3β,5α,25R)-3-[(4",6"-Bis[3,5-dimethoxy-phenylcarbamoyl]-2',2",3',3",6'-penta-acetyl-β-D-cellobiosyl)oxy]-spirostan-11-one Preparation C19

(3β,5α,25R)-3-[(6"-acetamido-6"-deoxy-4"-[2-fluoro-phenylcarbamoyl]-2',2",3',3",4',6'-hexa-acetyl-β-D-cellobiosyl)oxy]-spirostan-11-one Preparation C20

(3β,5α,25R)-3-[(6"-acetamido-6'-deoxy-2',2",3',3",4",6"-hexa-acetyl-β-D-cellobiosyl)oxy]-spirostan-11-one Preparation C21

(3β,5α,25R)-3-[(6"-deoxy-6"-[3-(2-fluoro-phenyl)-ureido]-2',2",3',3",4',6'-hexa-acetyI-β-D-cellobiosyl)oxy]-spirostan-11-one Preparation C22

(3β,5α,25R)-3-[(6"-[2-fluoro-phenylcarbamoyl]-2",2",3',3",4',6"-hexa-acetyl -β-D-lactosyl)oxy]-spirostan-11-one Preparation C23

(3β,5α,25R)-3-[(4",6"-Bis[3-nitro-phenylcarbamoyl]-2',2",3',3",6"-penta-acetyl -β-D-cellobiosyl)oxy]-spirostan-11-one Preparation C24

(3β,5α,25R)-3-[(6"-deoxy-6"-(2,6-dichloro-benzamido)-2',2",3',3",4',6"-hexa-acetyl -β-D-cellobiosyl)oxy]-spirostan-11-one Preparation C25

(3β,5α,25R)-3-[(6"-deoxy-6"-benzamido-2',2",3',3",4",6"-hexa-acetyl -β-D-cellobiosyl)oxy]-spirostan-11-one Preparation C26

(3β,5α,25R)-3-[(6"-deoxy-6"-(phenylacetamido)-2',2",3',3",4',6'-hexa-acetyl -β-3-D-cellobiosyl)oxy]-spirostan-11-one Preparation C27

(3β,5α,25R)-3-[(6"-Deoxy-6"-(2-fluoro-phenylacetamido)-2',2",3',3",4',6"-hexa-acetyl -β-D-cellobiosyl)oxy]-spirostan-11-one Preparation C28

(3β,5α,25R)-3-[(4",6"-Bis[2-thienylcarbamoyl]-2',2",3',3",6"-penta-acetyl -β-D-cellobiosyl)oxy]-spirostan-11-one Preparation C29

(3β,5α,25R)-3-[(6"-deoxy-4"-[2-fluoro-phenylcarbamoyl]-2',2",3',3",6"-pentaacetyl-β-D-cellobiosyl)oxy]-spirostan-11-one Preparation C30

(3β,5α,11β,25R)-3-[(4",6"-Bis[2-fluoro-phenylcarbamoyl]-2',2",3',3",6"-pentaacetyl-β-D-cellobiosyl)oxy]-11-acetoxy-spirostane Preparation D1

(3β,5α,25R)-3-[(4",6"-Bis[4-hydroxy-butylcarbamoyl]-pentaacetyl-β-D-cellobiosyl)oxy]spirostan-11-one Carbamoylation Using Carbonyl Dimidazole A mixture of (3β,5α,25R)-3-[(2',2",3',3",6"-pentaacetyl-β-D-cellobiosyl) oxy]spirostan-11-one (1.0 g, 1.04 mmol), carbonyl diimidazole (0.42 g, 2.6 mmol), and diisopropyl-ethyl amine (0.9 mL, 5.2 mmol) in dichloroethane (7 mL) was stirred at room temperature for 2 hours; 4-hydroxybutylamine (0.24 mL, 2.6 mmol) was added and the mixture was stirred for 5 hours at room temperature. The mixture was diluted with ethyl acetate and washed with 1 N hydrochloric acid (2×), saturated sodium bicarbonate solution (1×) and brine (1×), dried over sodium sulfate, filtered and concentrated in vacuo. The residue was purified by flash chromatography (1–3% methanol/chloroform) to afford 450 mg (37%) product as a colorless solid. $^1$H NMR (250 MHz, CDCl$_3$) δ 7.2 (bt, 2H); 5.1 (m, 2H); 4.8 (m, 2H); 4.55 (m, 1H); 4.3 (m, 2H); 4.1 (m, 1H); 3.8 (m, 2H); 3.6 (m, 1H); 3.4 (m, 4H); 3.2 (m, 1H); 2.9 (m, 4H); 2.5 (s, 2H); 2.3 (m, 2H); 2.0–1.0 (m, 52H); 0.9 (s, 3H); 0.85 (d, 3H, J=7Hz); 0.7 (d, 3H, J=7Hz); 0.6 (s, 3H).

In an analogous manner, the following compounds, Preparation D2–D38 were prepared from the appropriate starting material using the above general procedure.

Preparation D2

(3β,5α,25R)-3-[(4",6"-Bis[phenyl-thiocarbamoyl]-2',2",3',3",6'-penta-acetyl -β-D-cellobiosyl)oxy]-spirostan-11-one Preparation D3

(3β,5α,25R)-3-[(6"-phenyl-thiocarbamoyl -2',2",3',3",6"-penta-acetyl -β-D-cellobiosyl)oxy]-spirostan-11-one Preparation D4

(3β,5α,25R)-3-[(4",6"-Bis[pyrrolidin-1-ylcarbamoyl]-2',2",3',3",6'-penta-acetyl -β-D-cellobiosyl)oxy]-spirostan-11-one Preparation D5

(3β,5α,25R)-3-[(4",6"-Bis[morpholin-1-ylcarbamoyl]-2',2",3',3",6'-penta-acetyl -β-D-cellobiosyl)oxy]-spirostan-11-one Preparation D6

(3β,5α,25R)-3-[(6"-[α-methoxycarbonyl-benzyl carbamoyl]-2',2",3',3",6'-penta-acetyl-β-D-cellobiosyl)oxy]-spirostan-11-one Preparation D7

(3β,5α,25R)-3-[(4",6"-Bis[2-fluoro-benzylcarbamoyl]-2',2",3',3",6'-penta-acetyl -β-D-cellobiosyl)oxvl-spirostan-11-one Preparation D8

(3β,5α,25R)-3-[(4",6"-Bis[2-thienyl-methylcarbamoyl]-2',2",3',3",6'-penta-acetyl-β-D-cellobiosyl)oxy]-spirostan-11-one Preparation D9

(3β,5α,25R)-3-[(4",6"-Bis[2-furan-2-yl-methylcarbamoyl]-2',2",3',3",6'-penta-acetyl -β-D-cellobiosyl)oxy]-spirostan-11-one Preparation D10

(3β,5α,25R)-3-[(4",6"-Bis[2-ethoxycarbonyl-propylcarbamoyl]-2',2",3',3",6'-penta-acetyl-β-D-cellobiosyl)oxy]-spirostan-11-one Preparation D11

(3β,5α,25R)-3-[(4",6"-Bis[ethoxycarbonyl-methylcarbamoyl]-2',2",3',3",6'-penta-acetyl-β-D-cellobiosyl)oxy]-spirostan-11-one Preparation D12

(3β,5α,25R)-3-[(6"-[1-ethoxycarbonyl-2-(2-thienyl)-ethylcarbamoyl]-2',2",3',3",6'-penta-acetyl-β-D-cellobiosyl)oxy]-spirostan-11-one Preparation D13

(3β,5α,25R)-3-[(6"-1-ethoxycarbonyl-2-phenyl-ethylcarbamoyl]-2',2",3',3",6'-penta-acetyl-β-D-cellobiosyl)oxy]-spirostan-11-one Preparation D14

(3β,5α,25R)-3-[(4",6"-Bis[-ethoxycarbonyl-2-phenyl-ethyl)carbamoyl]-2',2",3',3",6'-penta-acetyl-β-D-cellobiosyl)oxy]-spirostan-11-one Preparation D15

(3β,5α,25R)-3-[(4",6"-Bis[2-hydroxy-propylcarbamoyl]-2',2",3',3",6'-penta-acetyl -β-D-cellobiosyl)oxy]-spirostan-11-one Preparation D16

(3β,5α,12β,25R)-3-[(4",6"-Bis[ethoxycarbonyl-methylcarbamoyl]-2',2",3',3",6'-penta acetyl-β-D-cellobiosyl)oxy]-12-acetoxy-spirostan-11-one Preparation D17

(3β,5α,25R)-3-[(4",6"-Bis[2-methoxycarbonyl-ethylcarbamoyl]-2',2",3',3",6'-penta-acetyl-β-D-cellobiosyl)oxy]-spirostan-11-one Preparation D18

(3β,5α,25R)-3-[(4",6"-Bis[tetrahydro-furan-2-yl-methylcarbamoyl]-2',2",3',3",6'-penta-acetyl-β-D-cellobiosyl)oxy]-spirostan-11-one Preparation D19

(3β,5α,25R)-3-[(4",6"-Bis[3-thienyl-methylcarbamoyl]-2',2",3',3",6'-penta-acetyl-β-D-cellobiosyl)oxy]-spirostan-11-one Preparation D20

(3β,5α,25R)-3-[(4",6"-Bis[2-(2-thienyl)-ethylcarbamoyl]-2',2",3',3",6'-penta-acetyl-β-D-cellobiosyl)oxy]-spirostan-11-one Preparation D21

(3β,5α,25R)-3-[(4", 6"-Bis[3,4-methylenedioxy-benzylcarbamoyl]-2', 2",3',3",6'-penta-acetyl-β-D-cellobiosyl)oxy]-spirostan-11-one Preparation D22

(3β,5α,25R)-3-[(4", 6"-Bis[2-trifluoromethyl-benzylcarbamoyl]-2',2",3',3",6'-penta-acetyl-β-D-cellobiosyl)oxy]-spirostan-11-one Preparation D23

(3β,5α,25R)-3-[(4",6"-Bis[5-methyl-2-thienyl-methylcarbamoyl]-2', 2",3',3",6'-penta-acetyl-β-D-cellobiosyl)oxy]-spirostan-11-one Preparation D24

(3β,5α,25R)-3-[(4",6"-Bis[4-bromo-2-thienyl-methylcarbamoyl]-2',2",3',3",6'-penta-acetyl-β-D-cellobiosyl)oxy]-spirostan-11-one Preparation D25

(3β,5α,25R)-3-[(4",6"-Bis[5-bromo-2-thienyl-methylcarbamoyl]-2',2",3',3",6'-penta-acetyl-β-D-cellobiosyl)oxy]-spirostan-11-one Preparation D26

3β,5α,12β,25R)-3-[(4",6"-Bis[3-thienyl-methylcarbamoyl]-2', 2', 3",6'-penta-acetyl-β-D-cellobiosyl)oxy]-12-hydroxy-spirostan-11-one Preparation D27

3β,5α,25R)-3-[(4", 6"-Bis[2-methoxycarbonyl-2-methyl-propylcarbamoyl]-2', 2",3',3",6'-penta-acetyl-β-D-cellobiosyl)oxy]-spirostan-11-one Preparation D28

(3β,5α,25R)-3-[(4",6"-Bis[2-hydroxy-2-(2-thienyl)-ethylcarbamoyl]-2', 2',3',3",6'-penta-acetyl-β-D-cellobiosyl)oxy]-spirostan-11-one Preparation D29

(3β,5α,12β,25R)-3-[(4",6"-Bis[2-methoxycarbonyl-ethylcarbamoyl]-2', 2",3',3",6'-penta-acetyl-β-D-cellobiosyl)oxy]-1 2-acetoxy-spirostan-11-one Preparation D30

(3β,5α,25R)-3-[(4",6"-Bis[thiazol-2-yl-methylcarbamoyl]-2', 2",3",6'-penta-acetyl -β-D-cellobiosyl)oxy]-spirostan-11-one Preparation D31

(3β,5α,25R)-3-[(4",6'-Bis[benzylcarbamoyl]-2', 2",3',3', 6'-penta-acetyl -β-D-cellobiosyl)oxy]-spirostan-11-one Preparation D32

(3β,5α,25R)-3-[(4", 6"-Bis[5-trifluoromethyl-benzothiazol-2-yl-methylcarbamoyl]-2', 2",3',3",6'-penta-acetyl-,-D-cellobiosyl) oxy]-spirostan-11-one Preparation D33

(3β,5α,25R)-3-[(4",6'-Bis[4-methoxy-benzylcarbamoyl]-2', 2",3',3",6'-penta-acetyl-β-D-cellobiosyl)oxy]-spirostan-11-one Preparation D34

(3β,5α,25R)-3-[(4",6"-Bis[2-(2-fluorophenyl)ethylcarbamoyl]-2',2",3',3',6'-penta-acetyl-β-D-cellobiosyl)oxy]-spirostan-11-one Preparation D35

(3β,5α,12β,25R)-3-[(4",6"-Bis[thiazol-2-yl-methylcarbamoyl]-2', 2",3',3",6'-penta-acetyl-β-D-cellobiosyl)oxy]-1 2-acetoxy-spirostan-11-one Preparation D36

(3β,5α,25R)-3-[(4",6'-Bis[3-methylisoxazol-5-yl-methylcarbamoyl]-2', 2",3',3",6'-penta-acetyl-β-D-cellobiosyl)oxy]-spirostan-11-one Preparation D37

(3β,5α,25R)-3-[(4",6"-Bis[2-methoxycarbonyl-butylcarbamoyl]-2', 2",3',3",6'-penta-acetyl-β-D-cellobiosyl)oxy]-spirostan-11-one Preparation D38

(3β,5α,25R)-3-[(4",6"-Bis[pyridin-3-yl-methylcarbamoyl]-2', 2",3',3",6'-pentaacetyl-β-D-cellobiosyl)oxy]-spirostan-11-one Preparation E (3β,5α,25R)-3-[(4",6"-Bis-[2-fluoro-phenylcarbamoyl]-2', 2",3',3",6'-pentachloroacetyl-β-D-cellobiosyl)oxy]-spirostan-11-one Carbamoylation Using Cuprous Chloride Cuprous chloride (1.74 g, 18 mmol) was added to a solution of (3β,5α,25R)-3-[(2', 2',3', 3",6'-pentachloroacetyl-,-D-cellobiosyl)oxy]-spirostan-11-one (5.0 g, 4.4 mmol) and 2-fluorophenylisocyanate (1.98 mL, 18 mmol) in dry dimethyl formamide (30 mL) at room temperature. After 2 h, the mixture was diluted with ethyl acetate (100 mL) and washed with 1N HCl (2×) and brine (1×), dried ($Na_2SO_4$) filtered and concentrated in vacuo. The residue was dissolved in methylene chloride (50 mL) and methanol (50 mL) was added. The methylene chloride was removed in vacuo and a solid precipitated from the methanol. The solid was filtered, washed with methanol and dried to afford 4.82 g product as a white solid (78%). m.p. 234–234.5° C. FAB MS: 1433 (M+Na)$^+$. $^1$H NMR (250 MHz, CDCl$_3$) 6 7.9 (m, 2H); 7.05 (m, 8H); 5.35 (dd, 1H, J=8.0, 7.0 Hz); 5.28 (dd, 1H, J=9.0, 8.0 Hz); 5.15 (dd, 1H, J=9.0, 9.0 Hz); 5.05 (dd, 1H, J=9.0, 8.0 Hz); 4.98 (dd, 1H, J=8.0, 7.0 Hz); 4.72 (d, 1H, J=9.0 Hz); 4.65–3.4 (m, 21 H); 3.35 (dd, 1H, J=10.0, 9.0 Hz); 2.45 (m, 1H); 2.2 (s, 2H); 2.1–1.1 (m, 22 H); 1.0 (s, 3H); 0.9 (d, 3H, J=7.0 Hz); 0.8 (d, 3H, J=7.0 Hz); 0.7 (s, 3 H).

Preparation F (3β,5α,25R)-3-[(6', 6"-dideoxy-pentaacetyl-β-D-cellobiosyl)oxy]spirostan-11-one Deiodination To a solution of (3β,5α,25R)-3-[(6', 6"-dideoxy-6',6'-diiodo-pentaacetyl-β-D-cellobiosyl)oxy]spirostan-11-one (150 mg, 0.128 mmol) and tri-n-butyl tin hydride (0.105 mL, 0.39 mmol) in anhydrous toluene (5 mL), azoisobutyrylnitrile (10 mg) was added at room temperature. The reaction mixture was gently refluxed under nitrogen atmosphere for 3 hours, cooled and concentrated in vacuo. The residual material was triturated with hexanes, filtered and dried to afford a colorless solid. The crude product was flash chromatographed (5% ethyl acetate/ methylene chloride) to afford 0.1 g (82%) of a white solid. $^1$HNMR (250 MHz, CDCl$_3$) δ 5.1 (m, 2H); 4.8 (m, 2H); 4.5 (m, 2H); 4.1 (q, 1H, J=7Hz); 3.4 (m, 4H); 2.45 (bd, 1H, J=14Hz); 2.25 (s, 2H); 2.12 (s, 3H); 2.10 (s, 3H); 2.09 (s, 3H); 2.06 (s, 3H); 1.98 (s, 3H); 1.9–1.3 (m, 25H); 1.3 (d, 3H, J=6Hz); 1.22 (d, 3H, J=6Hz); 1.0 (s, 3H); 0.9 (d, 3H, J=7Hz); 0.8 (d, 3H, J=7Hz); 0.7 (s, 3H).

Preparation G1

(3β,5α,25R)-3-[(6',6"-dideoxy-6', 6"-difluoro-pentaacetyl-β-D-cellobiosyl)oxy]spirostan-11-one Fluorination To a solution of (3β,5α,25R)-3-[(2', 2",3',3",4"-pentaacetyl-β-D-cellobiosyl)oxy] spirostan-11-one (250 mg, 0.259 mmol) in anhydrous dimethoxy ether (5 mL), DAST (0.34 mL, 2.59 mmol) was added at 0° C. After 20 minutes, the reaction was warmed to room temperature for 30 minutes, then to 40° C. for 1.5 hours. Upon completion, the reaction was cooled to 0° C., diluted with ethyl acetate (50 mL) and poured into iced water. The organic layer was washed with 1N hydrochloric acid solution (1×), sodium bicarbonate solution (1×) and brine (1×), dried over sodium sulfate, filtered and concentrated in vacuo. The crude product was purified via flash chromatography (40% ethyl acetate/hexanes) to afford 190 mg (76%) of a white solid.$^1$HNMR (250 MHz, CDCl$_3$) δ 5.15 (dd, 1H, J=8.8 Hz); 5.05 (dd, 1H, J=9.9 Hz); 4.9 (dd, 1H, J=9.8 Hz); 4.85 (dd, 1H, J=9.8 Hz); 4.7 (m, 1H); 4.5 (m, 4H); 3.85 (dd, 1H, J=9.0, 9.0 Hz); 3.6 (m, 1H); 3.5 (m, 1H); 3.35 (dd, 1H, J=10.0, 11.0 Hz); 2.5 (m, 1H); 2.2 (s, 2H); 2.01 (s, 3H); 2.0 (s,6H); 1.98 (s, 3H); 1.97 (s, 3H); 1.9–1.0 (m, 27H); 1.0 (s, 3H); 0.92 (d, 3H, J=7Hz); 0.75 (d, 3H, J=7Hz); 0.7 (s, 3H). MS: 969 (M+H)$^+$ m.p. 267–269° C.

In an analogous manner the following compounds, Preparations G2–G5, were prepared from the appropriate starting material using the above general procedure.

Preparation G2

(3β,5α,25R)-3-[(6"-deoxy-6"-fluoro-hexaacetyl-β-D-cellobiosyl)oxy]spirostan-11-one Preparation G3

(3B 5a,25R)-3-[(6', 6"-dideoxy-6', 6"-difluoro-pentaacetyl-β-D-maltosyl)oxy]spirostan-11-one Preparation G4

(3β,5α,12β,25R)-3-[(6',6"-dideoxy-6',6"-difluoro-pentaacetyl-β-D-cellobiosyl)oxy]-12-acetoxy-spirostan-11-one Preparation G5

(3β,5α,12β,25R)-3-[(6'-deoxy-6'-fluoro-hexaacetyl-β-D-cellobiosyl)oxy]-12-acetoxy-spirostan-11-one Preparation H1

(3β,5α,25R)-3-[(6', 6"-dideoxy-6',6"-diiodo-pentaacetyl-β-D-cellobiosyl)oxy]spirostan-11-one Iodination A mixture of (3β,5α,25R)-3-[(2',2",3',3",4'-pentaacetyl-β-D-cellobiosyl)oxy] spirostan-11-one (2.00 g, 2.08 mmol), imidazole (0.85 g, 12.0 mmol), and triphenylphosphine (3.26 g, 12.0 mmol) was dissolved in toluene (40 mL). Iodine (2.10 g, 8.30 mmol) was added and the reaction was gently refluxed overnight. Upon completion, the reaction was cooled, diluted with ethyl acetate, washed with 1N hydrochloric acid (1×), sodium bicarbonate solution (1×) and brine (1×), dried over sodium sulfate, filtered and concentrated in vacuo. The crude product was purified via flash chromatography (10% ethyl acetate/ methylene chloride) to afford 1.78 g (72.3%) of a white solid.

$^1$HNMR (250 MHz, CDCl$_3$) δ 5.25–3.0 (m, 18H); 2.6–1.05 (m, 42H); 0.95 (d, 3H, J=7 Hz); 0.80 (s, 3H); 0.75 (d, 3H, J=7 Hz); 0.60 (s, 3H). MS: 1171 (M+H)$^+$.

Preparation I1

(3β,5α,25R)-3-[(6',6"-dideoxy-6', 6"-dichloro-pentaacetyl-β-D-cellobiosyl)oxy]spirostan-11-one Chlorination A mixture of (3β,5α,25R)-3-[(6', 6"-dimesyl-pentaacetyl-β-D-cellobiosyl)oxy] spirostan-11-one (0.10 g, 0.09 mmol), lithium chloride (0.15 g) and N,N-dimethylformamide (2 mL) was heated to 85° C. and stirred for 3 hours. The reaction was then cooled, diluted with ethyl acetate (20 mL), washed with water (2×) and brine (1×), dried over sodium sulfate, filtered and concentrated in vacuo. The residual material was triturated with hexanes, filtered and dried to afford 0.079 g (88%) of a white solid.

$^1$HNMR (250 MHz, CDCl$_3$) δ 5.2–3.3 (m, 18H); 2.6–1.1 (m, 40H); 1.0 (s, 3H); 0.90 (d, 3H, J=7 Hz); 0.75 (d, 3H, J=7 Hz); 0.70 (s, 3H). MS: 1001 (M+H)+; m.p.>275° C.

In an analogous manner the following compound, Preparation I2, was prepared from the appropriate starting material using the above general procedure.

Preparation I2

(3β,5α,25R)-3-[(6', 6"-dideoxy-6', 6"-dichloro-pentaacetyl-β-D-lactosyl)oxy]spirostan-11-one Preparation J1

(3β,5α,25R)-3-[(6', 6"-dimethyl-pentaacetyl-β-D-cellobiosyl)oxy]spirostan-11-one Mesylation A solution of (3β,5α,25R)-3-[(2', 2",3',3",4'-pentaacetyl-β-D-cellobiosyl)oxy] spirostan-11-one (1.00 g, 1.04 mmol) and triethylamine (1.50 mL, 10.40 mmol) in dichloromethane (10 mL) was cooled to 0C. Mesyl chloride (0.48 mL, 6.22 mmol) and dimethylaminopyridine (0.02 g) were added and the reaction was stirred at 0° C. for 2 hours. The reaction was diluted with ethyl acetate (50 mL), washed with 1 N hydrochloric acid solution (2×), sodium bicarbonate solution (1×) and brine (1×), dried over sodium sulfate, filtered and concentrated in vacuo. The residual material was dissolved in dichloromethane(10 mL) and hexanes were added (20 mL). The dichloromethane was removed in vacuo and the resulting precipitate was filtered, washed with hexanes and dried under vacuum to afford 1.10 g (94%) of a white solid.

$^1$HNMR (250 MHz, CDCl$_3$) δ 5.25–3.3 (m, 18H); 3.1 (d, 6H, J=7 Hz); 2.6–1.1 (m, 40H); 1.0 (s, 3H); 0.95 (d, 3H, J=7 Hz); 0.77 (d, 3H, J=7 Hz); 0.7 (s, 3H).

In an analogous manner the following compound, Preparation J2, was prepared from the appropriate starting material using the above general procedure.

Preparation J2

(3β,5α,25R)-3-[(6', 6"-dimesyl-pentaacetyl-β-D-lactosyl)oxy]spirostan-11-one

Preparation K (3β,5α,25R)-3-[(6',6"-Bis-[ethoxymethyl-pentaacetyl-β-D-cellobiosyl)oxy]spirostan-11-one Ethoxymethylation A mixture of (3β,5α,25R)-3-[(2', 2",3', 3',4"-pentaacetyl-β-D-cellobiosyl)oxy] spirostan-11-one (0.50 g, 0.52 mmol), dichloroethane (5 mL), diisopropylethylamine (1 mL) and ethoxymethyl chloride (0.196 g, 2.07 mmol) was stirred at room temperature for 4 hours. At this time, the reaction was warmed to 50° C. for 2 hours. Upon completion, the reaction was cooled and quenched with methanol. The quenched mixture was diluted with ethyl acetate, washed with water (1×), 1 N hydrochloric acid (2×) and brine (1×). The organic layer was then dried over sodium sulfate, filtered and concentrated in vacuo. The crude product was purified via flash chromatography (60% ethyl acetate/ 40% hexanes) to afford 0.5054 g (46.7%). $^1$HNMR (250 MHz, CDCl$_3$) δ 5.15 (dd, 1H, J=8.8 Hz); 5.1 (m, 1H); 4.85 (m, 2H); 4.7 (s, 1H); 4.6 (s, 1H); 4.5 (dd, 1H, J=18.7 Hz); 4.45 (m, 1H); 4.1 (q, 2H, J=6Hz); 3.8 (m, 2H); 3.5 (m, 1OH); 2.5 (m, 1H); 2.2 (s, 2H); 2.01 (s, 3H); 2.0 (s, 6H); 1.98 (s, 3H); 1.97 (s, 3H); 1.9–1.0 (m, 26H); 1.2 (m, 6H); 1.0 (s, 3H); 0.92 (d, 3H, J=7Hz); 0.75 (d, 3H, J=7Hz); 0.7 (s, 3H).

Preparation L (3β,5α,25R)-3-[(6"-deoxy-2',2",3',3",6'-penta-acetyl-β-D-cellobiosyl)oxy]-spirostan-11-one 2,2'-Azo-bis-(2-methyl)propionitrile (0.5 g) was added to a solution of tri-n-butyl tin hydride (3.73 mL, 13.9 mmol) and (3β,5α,25R)-3-[(6"-bromo-6"-deoxy-2', 2',3',3",6'-pentaacetyl-β-D-cellobiosyl)oxy]-spirostan-11-one (9.54 g, 9.28 mmol) in dry toluene (200 mL) at room temperature. The mixture was heated to a gentle reflux for 3 h, was cooled and concentrated in vacuo. The product was purified by flash chromatography (70% ethyl acetate/hexanes) to afford 7.2 g of the title compound as a white solid (82%). m.p. 209–211° C. FAB MS: 971 (M+Na)$^+$. $^1$H NMR (250 MHz, CDCl$_3$) δ 5.05 (dd, 1H, J=10.0, 9.0 Hz); 4.85 (m, 3H); 4.48 (m, 4H); 4.05 (dd, 1H, J=12.0, 5.0 Hz); 3.7 (dd, 1H, J=9.0, 8.0 Hz); 3.45 (m, 6H); 2.45 (m, 1H); 2.2 (s, 2H); 2.1 (s, 3H); 2.05 (s, 3H); 2.0 (s, 9H); 2.0–1.1 (m, 23H); 1.0 (s, 3H); 0.95 (d, 3H, J=7.0 Hz); 0.90 (d, 3H, J=7.0 Hz); 0.8 (d, 3H, J=7.0 Hz); 0.7 (s, 3H).

Preparation M (3β,5α,25R)-3-[(6"-amino-6'-deoxy-2',2",3',3",6'-penta-acetyl-β-D-cellobiosyl)oxy]-spirostan-11-one formate Azide Reduction 10% Paladium on carbon (300 mg) was added to a solution of (3β,5α,25R)-3-(6"-azido-6"-deoxy-2', 2",3',3", 6'-pentaacetyl-β-D-cellobiosyl)oxy]-spirostan-11-one (953 mg, 0.96 mmol) in methanol (15 mL) containing 2 mL of formic acid. The mixture was placed under 35 psi of hydrogen and shaken in a Parr apparatus for 2 h. The flask was purged with nitrogen and the catalyst was removed by filtration. The filtrate was concentrated in vacuo and the residue was purified by flash chromatography (2 to 8% methanol/ethyl acetate) to afford the amine as its formate salt as a white solid (600 mg, 62%). FAB MS: 986 (M+Na)+. $^1$H NMR (250 MHz, CDl$_3$) δ 5.15 (dd,1H,J=8.0, 8.0 Hz); 4.98 (dd, 1H, J=7.0, 7.0 Hz); 4.8 (dd, 2H, J=7.0, 7.0 Hz); 4.5 (m, 4H); 4.05 (dd, 1H, J=12.0, 6.0 Hz); 3.7–3.0 (m, 12H); 2.5 (m, 1H); 2.25 (s, 2H); 2.12 (s, 3H); 2.08 (s, 3H); 2.02 (s, 3H); 2.0 (s, 6H); 2.0–1.0 (m, 22H); 1.0 (s, 3H); 0.9 (d, 3H, J =.7.0 Hz); 0.8 (d, 3H, J=7.0 Hz); 0.7 (s, 3H).

Preparation N (3β,5α,25R)-3-[(6"-azido-6"-deoxy-2',2",3',3",6'-pentaacetyl -β-D-cellobiosyl)oxy]-spirostan-11-one Bromide Displacement With Sodium Azide Sodium azide (1.98 g, 0.031 mol) was added to a solution of (3β,5α,25R)-3-[(6"-bromo-6"-deoxy-2', 2",3',3",6'-pentaacetyl-β-D-cellobiosyl)oxy]-spirostan-11-one (7.84 g, 7.63 mmol) in dry DMF (60 mL) at room temperature. The mixture was heated to 60° C. for 4.5 h, cooled, and diluted with ethyl acetate (100 mL). The mixture was washed with water (3×) and brine (1×), dried (Na$_2$SO$_4$) filtered and concentrated in vacuo. The product was triturated from ethyl acetate/hexanes, filtered and dried to afford 7.2 g of the title product as a white solid (95%). m.p. 164–166° C. FAB MS: 1012 (M+Na)+. $^1$H NMR (250 MHz, CDCl$_3$) δ 5.15 (dd, 1H,J=9.0, 8.0 Hz); 4.95 (dd, 1H, J=13.0, 8.0 Hz); 4.8 (dd, 2H, J=8.0, 7.0 Hz); 4.5 (m, 3H); 4.1 (dd, 1H, J=12.0, 6.0 Hz); 3.75 (dd, 1H, J=8.0, 7.0 Hz); 3.7–3.0 (m, 9H); 3.1 (d, 1H, J=5.0 Hz); 2.4 (m, 1H); 2.2 (s, 2H); 2.1 (s, 3H); 2.08 (s, 6H); 2.02 (s, 3H); 2.0 (s, 3H); 2.0–1.0 (m, 23H); 1.0 (s, 3H); 0.9 (d, 3H, J=7.0 Hz); 0.75 (d, 3H, J=7.0 Hz); 0.7 (s, 3H).

Preparation O (3β,5α,25R)-3-[(6"-bromo-6"-deoxy-2',2",3',3",6'-pentaacetyl-R-D-cellobiosyl)oxy]-spirostan-11-one Bromination Carbon tetrabromide (2.9 g, 8.7 mmol), triphenyl phosphine (5.4 g, 20.7 mmol) and pyridine (2.68 mL, 33 mmol) were added to a solution of (3β,5α,25R)-3-[(2', 2",3',3",6'-pentaacetyl-β-D-cellobiosyl)oxy]-spirostan-11-one (8.0 g, 8.3 mmol) in methylene chloride (60 mL) at room temperature. After 19 h, the reaction was quenched by the addition of methanol (2 mL), diluted with methylene chloride (100 mL) and washed with NaHCO$_3$ sol. (1×), 1N HCl (1×) and brine (1×). The solution was dried (Na$_2$SO$_4$) filtered and concentrated in vacuo. The residue was purified by flash chromatography (50% ethyl acetate/hexanes) to afford the bromide as a white solid (7.9 g, 93%). m.p. 218–220. FAB MS: 1050 (M+Na)+. $^1$H NMR (250 MHz, CDCl$_3$) δ 5.15 (dd,1H,J=9.0, 8.0 Hz); 4.95 (dd, 1H, J=13.0, 8.0 Hz); 4.8 (dd, 1H, J=9.0, 2.0 Hz); 4.5 (m, 3H); 4.1 (dd, 1H, J=12.0, 6.0 Hz); 3.85–3.4 (m, 1OH); 3.3 (dd,1H, J=9.0, 9.0 Hz); 2.98 (d, 1H, J=6.0 Hz); 2.45 (m, 1H); 2.2 (s, 2H); 2.1 (s, 6H); 2.08 (s, 3H); 2.02 (s, 6H); 2.0–1.0 (m, 22H); 1.0 (s, 3H); 0.9 (d, 3H, J=7.0 Hz); 0.75 (d, 3H, J=7.0 Hz); 0.7 (s, 3H).

Preparation P (3β,5α,25R)-3-[(2', 2",3', 3",6'-penta-acetyl-6"-triisopropylsilyl-β-D-cellobiosyl)oxy]-spirostan-11-one Monosilylation Triisopropyl silyl chloride (0.37 mL, 1.7 mmol) was added to a solution of (3β,5α,25R)-3-[(2', 2",3',3",6'-pentaacetyl-β-D-cellobiosyl)oxy]-spirostan-11-one (1.0 g, 1.04 mmol) in dry dimethyl formamide (5 mL) containing imidazole (141 mg, 2.07 mmol) and N,N-dimethyl 4-amino pyridine (50 mg). After 24 h, an additional 0.1 mL of triisopropyl silyl chloride was added and the mixture stirred another 24 h. The mixture was diluted with ethyl acetate (50 mL) and washed with water (3×), 1 N HCl (2×) and brine (1×), dried (Na$_2$SO$_4$) filtered and concentrated in vacuo. The residue was purified by flash chromatography (40% ethyl acetate/hexanes) to afford the title compound as a colorless foam (690 mg, 60%). $^1$H NMR (250 MHz, CDCl$_3$) δ 5.12 (dd, 1H, J=9.0, 8.0 Hz); 5.05 (dd, 1H, J=9.0, 8.0 Hz); 4.8 (ddd, 1H, J=8.0, 8.0, 2.0 Hz); 4.5 (m, 2H); 4.1 (m, 1H); 3.9–3.3 (m, 13H); 2.5 (m, 1H); 2.25 (s, 2H); 2.1 (s, 3H); 2.08 (s, 3H); 2.04 (s, 6H); 2.02 (s, 3H); 1.9–1.05 (m, 43H); 1.0 (s, 3H); 0.9 (d, 3H, J=7.0 Hz); 0.78 (d, 3H, J=7.0 Hz); 0.7 (s, 3H).

Preparation Q (3β,5α,25R)-3-[(2',2",3',3",6'-penta-chloroacetyl -β-D-cellobiosyl)oxy]-spirostan- 1 -one Paramethoxy Benzylidene Hydrolysis Trifluoroacetic acid (19 mL) was added to a solution of (3β,5α,25R)-3-[(4",6"-[4-methoxybenzylidene]-2', 2",3',3", 6'-penta-chloro-acetyl-β-D-cellobiosyl)oxy]-spirostan-11-one (23.7 g, 0.019 mol) in dichloromethane (150 mL) and methanol (50 mL). After 4 h, the mixture was washed with water (3×) NaHCO$_3$ (2×) and brine (1×), dried (Na$_2$SO$_4$) filtered and concentrated. The residue was dissolved in a minimal amount of ethyl acetate and precipitated with hexanes. The solid was filtered and washed with hexanes and dried to afford 19.7 g product as a white solid (92%). m.p. 228–229. FAB MS: 1159 (M+Na)+. $^1$H NMR (250 MHz, CDCl$_3$) δ 5.2 (dd, 1H, J=9.0, 9.0 Hz); 5.1 (dd, 1H, J=9.0, 9.0 Hz); 4.95 (m, 2H); 4.6 (m, 3H); 4.5 (ddd, 1H, J=8.0, 7.0, 7.0 Hz); 4.2–3.4 (m, 20H); 3.35 (dd, 1H, J=9.0, 9.0 Hz); 2.9 (d, 1H, J=6.0 Hz); 2.45 (m, 1H); 2.2 (s, 2H); 2.1–1.1 (m, 22H); 1.0 (s, 3H); 0.94 (d, 3H, J=7.0 Hz); 0.77 (d, 3H, J=7.0 Hz); 0.7 (s, 3H).

Preparation R (3β,5α,25R)-3-[(4",6"-[4-methoxybenzylidene]-2',2",3', 3",6'-penta-chloro-acetyl-β-D-cellobiosyl)oxy]-spirostan-11-one Paramethoxybenzylidene Formation and Chloroacetylation Camphorsulfonic acid (3 g) was added to a mixture of (3β,5α,25R)-3-[(β-D-cellobiosyl)oxy]-spirostan-11-one (50 g, 0.066 mol) and anisaldehyde dimethyl acetal (50 mL, 0.29 mol) in 1,2-dichloroethane (1500 mL). The suspension was heated to reflux temperature and 200 mL of solvent was distilled off. After 4 h at reflux temperature, the dark, gelatinous mixture was cooled to 0° C. and treated with pyridine (160 mL, 1.99 mol) and chloroacetic anhydride (170 g, 1 mmol). The reaction was allowed to warm to room temperature and after 2 h, the mixture was washed with 1N HCl (3×), NaHCO$_3$ (1×) and brine (1×), dried (Na$_2$SO$_4$), filtered and concentrated in vacuo. The residue was dissolved in a minimum amount of ethyl acetate and the product was precipitated with hexanes. The solid was filtered, washed with hexanes and dried to afford 77 g product as a white solid (93%). m.p. 256–257. FAB MS: 1277 (M+Na)⁺. ¹H NMR (250 MHz, CDCl₃) δ 7.35 (d, 2H, J=9.0 Hz); 6.88 (d, 2H, J=9.0 Hz); 5.45 (s, 1H); 5.3 (m, 2H); 5.0 (m, 2H); 4.7 (d, 1H, J=7.0 Hz); 4.6 (m, 2H); 4.5 (dd, 1H, J=8.0, 8.0 Hz); 4.38 (dd, 1H, J=11.0, 6.0 Hz); 4.2–3.5 (m, 15H); 3.8 (s, 3H); 3.4 (dd, 1H, J=11.0, 10.0 Hz); 2.5 (m, 1H); 2.25 (s, 2H); 2.1–1.0 (m, 25H); 1.0 (s, 3H); 0.94 (d, 3H, J=7.0 Hz); 0.78 (d, 3H, J=7.0 Hz); 0.7 (s, 3H).

Preparation S1

(3β,5α,25R)-3-[(2', 2',3',3',6'-pentaacetyl-β-D-cellobiosyl)oxy]spirostan-11-one Benzylidene Hydrolysis (3β,5α,25R)-3-[(4"6"-benzylidene-pentaacetyl-β-D-cellobiosyl)-oxy]spirostan-11-one (6.5 g, 6.16 mmol) was added to glacial acetic acid (80 mL) and water (20 mL). The reaction was heated to 80° C. and stirred for 2 hours under nitrogen atmosphere. Upon completion, the reaction was cooled and then was added to ice. The organic material was extracted with ethyl acetate, then washed with water (1×), saturated sodium bicarbonate solution (1×), water (1×) and brine (1×). The organic layer was dried over sodium sulfate, filtered and concentrated in vacuo. The residual material was triturated with hexanes, filtered, washed with hexanes and dried to afford 4.4 g (75% yield) of product.

¹HNMR (250 MHz, CDCl₃) δ 5.25–3.3 (m, 19H); 2.95 (d, 1H, J=7 Hz); 2.6–1.1 (m, 40H); 1.0 (s, 3H); 0.90 (d, 3H, J=7 Hz); 0.8 (d, 3H, J=7 Hz); 0.7 (s, 3H). MS: 965 (M+H)⁺ m.p 210–212° C.

In an analogous manner the following compounds, Preparation S2–S3, were prepared from the appropriate starting material using the above general procedure.

Preparation S2

(3β,5α,12β,25R)-3-[(2', 2",3',3",6'-pentaacetyl-β-D-cellobiosyl)oxy]12-acetoxyspirostan-11-one Preparation S3

(3β,5α,11β,25R)-3-[(2', 2",3',3",6'-pentaacetyl-β-D-cellobiosyl)oxy]-11-acetoxy-spirostane Preparation T1

(3β,5α,25R)-3-[(4",6"-benzylidene-pentaacetyl-β-D-cellobiosyl)oxy]spirostan-11-one Benzylidene Formation and Acetylation A mixture of (3β,5α,25R)-3-[(β-D-cellobiosyl)oxy]spirostan-11-one(5.00 g, 6.63 mmol), camphorsulphonic acid (0.75 g), chloroform (200 mL) and benzaldehyde dimethyl acetal (5.00 mL) was heated to reflux temperature under nitrogen atmosphere. The reaction was stirred at reflux temperature for 5 hours. Upon formation of the benzylidene, the reaction was cooled in an ice bath and pyridine (16 mL, 0.19 mol), dimethylaminopyridine (2.00 g) and acetic anhydride (10 mL, 0.11 mol) were added. The reaction was warmed to room temperature and stirred overnight. The reaction mixture was then washed with water once. The reaction was partially concentrated in vacuo to remove most of the chloroform. The remaining material was diluted with ethyl acetate, washed with 1 N hydrochloric acid solution (3×), water (1×) and brine (1×). The organic layer was then dried over sodium sulfate, filtered and concentrated in vacuo. The residual material was triturated with hexanes, filtered, washed with hexanes and dried to afford 6.5 g (93% yield) of product. ¹HNMR (250 MHz, CDCl₃) δ 7.45–7.3 (m, 5H); 5.5 (s, 1H); 5.3–3.3 (m, 18H); 2.5–1.05 (m, 40H); 1.0 (s, 3H); 0.90 (d, 3H, J=7 Hz); 0.8 (d, 3H, J=7 Hz); 0.7 (s, 3H).

In an analogous manner the following compounds, Preparation T2–T3, were prepared from the appropriate starting material using the above general procedure.

Preparation T2

(3β,5α,12β,25R)-3-[(4",6"-benzylidene-pentaacetyl-β-D-cellobiosyl)oxy]-12-acetoxy-spirostan-11-one Preparation T3

(3β,5α,11β,25R)-3-[(4",6"-benzylidene-pentaacetyl-β-D-cellobiosyl)oxy]-11-acetoxy-spirostane Preparation U1

(3β,5α,25R)-3-[(2', 2",3', 3",4"-pentaacetyl-β-D-cellobiosyl)oxy]spirostan-11-one Desilylation A mixture of (3β,5α,25R)-3-[(6', 6"-bis-[t-butyldiphenylsilyl]-pentaacetyl-β-D-cellobiosyl)oxy]spirostan-11-one (15.04 g, 0.01 mol) and pyridine (100 mL) was cooled to 0° C. under nitrogen atmosphere. Hydrogen fluoride in pyridine (36.64 mL) was added and the reaction was gradually warmed to room temperature and allowed to stir for 4 hours. Upon completion, the reaction was cooled and quenched with water. The quenched mixture was dissolved in ethyl acetate, washed with water (1×), 1N hydrochloric acid (4×), brine (1×), dried over sodium sulfate, filtered and concentrated in vacuo. The residual material was triturated with hexanes, filtered, washed with hexanes and dried to afford 7.22 g (74.8%) of product. ¹HNMR (250 MHz, CDCl₃) δ 5.25–3.3 (m, 20H); 2.65–1.05 (m, 40H); 1.0 (s, 3H); 0.95 (d, 3H, J=8 Hz); 0.8 (d, 3H, J=8 Hz); 0.7 (s, 3H). MS: 965 (M+H)+; m.p. 233–234° C.

In an analogous manner the following compounds, Preparations U2–U4, were prepared from the appropriate starting material using the above general procedure.

Preparation U2

(3β,5α,25R)-3-[(2', 2',3',3",4"-pentaacetyl-β-D-lactosyl)oxy]spirostan-11-one

Preparation U3

(3β,5α,25R)-3-[(2', 2",3',3",4"-pentaacetyl-β-D-maltosyl)oxy]spirostan-11-one

Preparation U4

(3β,6α,12β,25R)-3-[(2', 2',3',3",4"-pentaacetyl-β-D-cellobiosyl)oxy]-12-acetoxy-spirostan-11-one Preparation V1

(3β,5α,25R)-3-[(6', 6"-di-(t-butyidiphenylsilyl)-pentaacetyl-β-D-cellobiosyl)oxy]spirostan-11-one Silylation and Acetylation A mixture of (3β,5α,25R)-3-[(β-D-cellobiosyl)oxy]spirostan-11-one (25 g, 0.03 mot), imidazole (15.78 g, 0.23 mol), dimethylaminopyridine (20 g) and N,N-dimethylformamide (400 mL) was cooled to 0° C. under nitrogen atmosphere. Tert-butyidiphenylsilyl chloride (34.45 mL, 0.13 mot) was added, the mixture was warmed to room temperature and stirred for 5 hours. Pyridine (53.57 mL, 0.66 mol) and acetic anhydride (54.87 mL, 0.50 mol) were added and the reaction was stirred overnight. The reaction was then quenched with water, diluted with ethyl acetate, washed with water (2×), 1N hydrochloric acid solution (3×), brine (1×), dried over sodium sulfate, filtered and concentrated in vacuo to afford a foam as the product (66.05 g, >100%). ¹HNMR (250 MHz, CDCl₃) δ 7.85–7.3 (m, 20H); 5.3–3.3 (m, 18H); 2.6–1.0 (m, 61H); 0.90 (d, 3H, J=7 Hz); 0.8 (d, 3H, J=7 Hz); 0.7 (s, 3H). m.p. 135° C.

In an analogous manner the following compounds, Preparations V2–V4, were prepared from the appropriate starting material using the above general procedure.

Preparation V2

(3B3,5a.25R)-3-[(6', 6"-di-(t-butyldiphenyl silyl)-pentaacetyl-β-D-lactosyl)oxy]spirostan-11-one Preparation V3

(3β,5α,25R)-3-[(6', 6"-di-(t-butyldiphenylsilyl)-pentaacetyl-β-D-maltosyl)oxy]spirostan-11-one Preparation V4

(3β,5α,12β,25R)-3-[(6', 6"-di-(t-butyidiphenylsilyl)-pentaacetyl-β-D-cellobiosyl)oxy]-12-acetoxy-spirostan-11-one Preparation W1

(3β,5α,25R)-3-[(β-D-cellobiosyl)oxy]spirostan-11-one

Deacetylation

A mixture of (3β,5α,25R)-3-[(heptaacetyl-β-D-cellobiosyl)oxy]spirostan-11-one (6.57 g, 6.26 mmol), sodium methoxide (68 mg, 1.25 mmol), methanol (35 mL) and tetrahydrofuran (75 mL) was heated to reflux for 1 hour, followed by stirring at room temperature for 12 hours. A white precipitate formed within 30 minutes. The final suspension was concentrated in vacuo to give 6.0 g of crude product. This material was purified by flash chromatography (eluent: chloroform followed by 8:2 chloroform:methanol) to give 2.71 g (57% yield) of the title compound. High resolution CAB MS (m/e): calculated for $C_{39}H_{62}O_{14}Na$ 777.4037, found 777.4108. Analysis: calc. for $C_{39}H_{62}O_{14}·2H_2O$, C 59.22 H 8.41; found C 59.48, H 8.48. MP: >300° C.

In an analogous manner the following compounds W2–W5 were prepared from the appropriate starting material using the above general procedure.

Preparation W2

(3β,5α,25R)-3-[(β-D-lactosyl)oxy]-spirostan-11-one

Preparation W3

(3β,5α,25R)-3-[(β-D-maltosyl)oxy]-spirostan-11-one

Preparation W4

(3β,5α,12β,25R)-3-(β-D-cellobiosyl)oxy]-12-hydroxy-spirostan-11-one

Preparation W5

(3β,5α, 11β,25R)-3-(β-D-cellobiosyl)oxy]-11-hydroxy-spirostane

Preparation X (3β,5α,25R)-3-[(Heptaacetyl-α-D-cellobiosyl)oxy]spirostan-11-one

Anomerization

Hydrobromic acid (30% in acetic acid, 1.2 mL) was added to a room temperature solution of (3β, 5α,25R)-3-[(heptaacetyl-β-D-cellobiosyl)-oxy]spirostan-11-one (2.0 g) in methylene chloride (35 mL) and the resulting mixture was stirred at room temperature for 94 hours. The reaction was quenched by slow addition of saturated aqueous sodium bicarbonate (20 mL). The organic layer was separated, dried over magnesium sulfate, and dried in vacuo to give 1.637 g of a black solid. Purification by repeated flash chromatography (1:1 hexane:ethyl acetate eluent) provided 651 mg (33% yield) of the title compound.

MS (m/e): 1049 (M+H), 1071 (M+Na). Analysis: calc. for $C_{53}H_{76}O_{21}·H_2O$, C 59.65 H 7.37; found C 59.66 H 7.00. MP: 248–249° C.

Preparation Y1

(3β,5α,25R)-3-[(Heptaacetyl-β-D-cellobiosyl)oxy]spirostane-11-one

Zinc Fluoride Promoted Coupling of Free Spirostane

A suspension of (3β,5α,25R)-3-hydroxyspirostan-11-one (3.0 g, 6.97 mmol) and anhydrous zinc fluoride (2.88 g, 27.9 mmol) in dry acetonitrile (175 mL) was dried by removal of 75 mL of acetonitrile by distillation. The suspension was allowed to cool, heptaacetyl-β-D-cellobiosyl bromide (9.75 g, 13.9 mmol) was added and the resulting suspension was heated to 65° C. for 3 hours. After cooling to room temperature, methylene chloride (150 mL) was added, the suspension was stirred for 10 minutes and filtered. The filtrate was concentrated in vacuo to give 10 g of crude product. This material was dissolved in 8:2 chloroform:methanol, preadsorbed on silica gel and purified by flash chromatography (eluent: 1:1 ethyl acetate:hexane followed by pure ethyl acetate) to give 6.81 g (93% yield) of the title material.

MS (m/e): 1049 (M+H). Analysis: calc. for $C_{53}H_{76}O_{21}·H_2O$, C 59.65, H 7.37; found C 59.86, H 7.25. MP: 210–212° C.

In an analogous manner the following compounds Y2–Y4 were prepared from the appropriate starting material using the above general procedure.

Preparation Y2

(3β,5α, 25R)-3-[(Hepta-acetyl-β-D-lactosyl)oxy]-spirostan-11-one

Preparation Y3

(3β,5α,12β,25R)-3-[(Hepta-acetyl-β-D-cellobiosyl)oxy]-12-acetoxy-spirostan-11-one Preparation Y4

(3β,5α,11β,25R)-3-[(Hepta-acetyl-β-D-cellobiosyl)oxy]-11-acetoxy-spirostane

Preparation Z (3β,5α,25R)-3-[(heptaacetyl-β-D-maltosyl)oxy]-spirostan-11-one

Mercuric Bromide/Mercuric Cyanide Promoted Coupling of Silylated Spirostane

Powdered 4A molecular sieves (4 g) were added to a solution of 3-trimethylsilyloxy-(3β,5α,25R)spirostan-11-one (3.90 g, 7.76 mmol) and acetobromomaltose (8.15 g, 11.7 mmol) in dichloromethane (60 mL) at room temperature. After stirring for 15 minutes $Hg(CN)_2$ (7.85 g, 31 mmol) and $HgBr_2$ (11.2 g, 31 mmol) were added and the mixture stirred at room temperature for 7 hours. The mixture was diluted with ethyl acetate and washed with 1 N hydrochloric acid (3×) and brine (1×), dried over sodium sulfate, filtered and concentrated in vacuo. The product was purified by flash chromatography (30–60% EtOAc/hexanes) and afforded 3.5 g (43%) of the title product. $^1$H NMR (250 MHz, $CDCl_3$) δ 5.4 (d, 1H, J=3Hz); 5.3 (dd, 1H, J=9.9 Hz); 5.2 (dd, 1H, J=8.8 Hz); 5.05 (dd, 1H, J=9.9 Hz);4.88 (dd, 1H, J=11.3 Hz); 4.7 (dd, 1H, J=10.8 Hz); 4.4 (m, 2H); 4.2 (m, 2H); 4.0 (m, 3H); 3.5 (m, 4H); 2.5 (m, 1H); 2.2 (s, 2H); 2.16 (s, 3H); 2.1 (s, 3H); 2.02 (s, 3H); 2.0 (s, 3H); 1.98 (s, 3H); 1.96 (s, 3H); 1.95 (s, 3H); 1.95–1.0 (m, 23H); 1.0 (s, 3H); 0.9 (d, 3H, J=7Hz); 0.65 (d, 3H, J=7Hz); 0.55 (s, 3H).

Preparation M (3β,5α,25R)3-trimethylsilyloxy-spirostan-11-one

Silylation of Spirostanes

Trimethylsilylchloride (3.27 mL, 25.8 mmol) was added to a solution of (3β,5α,25R)3-hydroxy-spirostan-11-one (4.0 g, 9.3 mmol) and triethylamine (6.5 mL, 46 mmol) in dichloromethane (60 mL) at room temperature. One gram of dimethyl aminopyridine was added and the reaction was stirred for 12 hours. The reaction was quenched with methanol (1 mL) and diluted with ethyl acetate, washed with water (5×) and brine (1×), dried ($Na_2SO_4$), filtered and concentrated in vacuo. The product was triturated with methanol, filtered and dried to afford 3.94 g (85%) product as a white solid. $^1$H NMR (250 MHz, CDCl$_3$) δ 4.5 (q, 1H, J=6Hz); 3.45 (m, 2H); 2.35 (t, 1H, J=10 Hz); 2.4 (dt, 1H, J=12.2 Hz); 2.2 (s, 2H); 2.1–1.1 (m, 12H); 1.02 (s, 3H); 0.9 (d, 3H, J=7.0 Hz); 0.78 (d, 3H, J=7 Hz); 0.69 (s, 3H); 0.1 (s, 9H).

Preparation BB1

(3β,5α,11β,12α,25R)-spirostan-3,11,12-triol (3β,5α,11α, 25R)-11,23-dibromo-3-acetoxyspirostan-12-one: The title compound was synthesized from (3β,5α,25R)-3-acetoxyspirostan-12-one according to the procedure described in *J. Chem. Soc.*, 1956, 4344.

(3β,5α, 11α,12β,25R)-11,23-dibromospirostan-3,12-diol: (3β,5α, 11α,25R)-11,23-dibromo-3-acetoxyspirostan-12-one (20.00 g, azeotropically dried with toluene) was dissolved in THF (600 mL) and cooled to –78° C. Lithium aluminum hydride (96.0 mL of 1.0 M THF solution) was slowly added and the resulting mixture was stirred at –78° C. for 2 hours and 0° C. for 0.5 hour. Using a cannula, the mixture was cautiously transferred into stirred 3 M aqueous ammonium chloride (200 mL). The organic phase was separated, combined with THF washes of the solid residues, and concentrated to give the title compound.

(3β,5α,11β,12β,25R)-23-bromo-11,12-epoxyspirostan-3-ol: The following procedure is a variation of that described in *Helv. Chim. Act.*, 1953, 36, 1241. (3β,5α,11α,12β,25R)-11,23-dibromospirostan-3,12-diol (18.08 g) was dissolved in pyridine (500 mL) at room temperature and treated with silver oxide (70.0 g). The resulting mixture was stirred in the dark for 71 hours. The mixture was filtered and the solid washed with ether and then chloroform. These washes were combined with the filtrate and concentrated. The resulting solid was purified by flash chromatography (1:1 hexane-:ethyl acetate) to give 12.2 g of a 1:1 mixture of the title compound and (3β,5α,25R)-23-bromospirostan-3-ol-12-one. Further chromatography (7:3 hexane:ethyl acetate) provides pure title compound. (3β,5α,11β,12α,25R)-23-bromo-12-(trichloroacetoxy)spirostan-3,11 -diol: Using the procedure described in *J. Chem. Soc.*, 1956, 4330, (3β,5α, 11β,12β,25R)-23-bromo-11,12-epoxyspirostan-3-ol was treated with trichloroacetic acid in toluene at room temperature for 3 days to give the title compound. (3β,5α, 11β,12α, 25R)-23-bromo-spirostan-3,11,12-triol: Using the procedure described in *J. Chem. Soc.*, 1956, 4330, (3β,5α,11β,12α, 25R)-23-bromo-12-(trichloroacetoxy)spirostan-3,11-diol was saponified with sodium hydroxide in water and ethanol to give the title compound.

(3β,5α, 11β,12α,25R)-spirostan-3,11,12-triol: Using the procedure described in *J. Chem. Soc.*, 1956, 4330, (3β,5α, 11β,12α,25R)-23-bromo-12-(trichloroacetoxy)-spirostan-3,11-diol was reduced with zinc and acetic acid to give the title compound.

Preparation BB2

(3β,5α, 12α,25R)spirostan-3,12-diol-11-one (3β,5α, 11β, 12α,25R)-3, 12-di(acetoxy)spirostan-11-ol: Using the procedure described in *J. Chem. Soc.*, 1956, 4330, (3β,5α, 11β,12α,25R)-spirostan-3,11,12-triol(preparation G1) was selectively acetylated with acetic anhydride and pyridine to give the title compound.

(3β,5α, 12α,25R)-3,12-di(acetoxy)spirostan-11-one: Using the procedure described in *Org. Syn.*, 1976, 55, 84, (3β,5α, 11β,12α,25R)-3,12-di(acetoxy)-spirostan-11-ol was oxidized with chromium trioxide and pyridine in methylene chloride to give the title compound.

(3β,5α, 12α,25R)-spirostan-3,12-diol-11-one: Using the procedure described in *Syn.*, 1973, 790, (3β,5α, 12α,25R)-3,12-di(acetoxy)spirostan-11-one was saponified with potassium cyanide in water, methanol and THF to give the title compound.

Preparation BB3

(3β,5α, 11β.25R)spirostan-3,11 -diol (3β,5α,25R)spirostan-3-ol-11-one (Aldrich Chemical Company, Milwaukee, Wis. or Steraloids Inc., Wilton, N.H., or see preparation G13) was converted into the title compound via reduction with lithium aluminum hydride in THF at room temperature according to the procedure described in *J. Am. Chem. Soc.*, 1951, 73, 1777.

Preparation BB4

(3β,5α,11α,25R)spirostan-3,11-diol (3β,5α,25R)spirostan-3-ol-11-one (Aldrich Chemical Company, Milwaukee, Wis. or Steraloids Inc., Wilton, N.H., or see preparation G13) was converted into the title compound via reduction with lithium and ammonia according to the procedure described in *J. Am. Chem. Soc.*, 1953, 75, 1282.

Preparation BB5

(3β,5α,11β,12β,25R)spirostan-3,11,12-triol (3β,5α,12β,25R)-3,12-di(acetoxy)spirostan-11-one (purchased from Steraloids, Inc., or see preparationG13) was converted into the title compound via reduction with lithium aluminum hydride in THF at room temperature according to the procedure described in *J. Am. Chem. Soc.*, 1951, 73, 1777.

Preparation BB6

(3β,5α,11α,12β,25R)spirostan-3,11,12-triol (3β,5α,12β,25R)spirostan-3,12-diol-11-one: (3β,5α,12β,25R)-3,12-di(acetoxy)-spirostan-11-one (purchased from Steraloids, Inc., or see preparation G13) was saponified with potassium carbonate in water, methanol and THF to provide the title compound.

(3β,5α,11α,12β,25R)spirostan-3,11,12-triol: (3β,5α,12β,25R)spirostan-3,12-diol-11-one was converted into the title compound via reduction with lithium and ammonia according to the procedure described in *J. Am. Chem. Soc.*, 1953, 75, 1282.

Preparation BB7

(3β,5α,25R)-spirostan-3-ol-11,12-dione (3β,5α,12β,25R)-3-(t-butyldimethylsilyloxy)spirostan-12-ol-11-one: Using the procedure described in *J. Am. Chem. Soc.*, 1972, 94, 6190, (3β,5α,12β,25R)-spirostan-3,12-diol-11-one (see preparation G6) was silylated with t-butyldimethylchlorosilane and imidazole in DMF to give the title compound.

(3β,5α,25R)-3-(t-butyldimethylsilyloxy)spirostan-11,12-dione: Using the procedure described in *Org. Syn.*, 1976, 55, 84, (3β,5α,12β,25R)-3-(t-butyldimethylsilyloxy)-spirostan-12-ol-11-one was oxidized with chromium trioxide and pyridine in methylene chloride to give the title compound.

(3β,5α,25R)-spirostan-3-ol-11,12-dione: Using the procedure described in *J. Am. Chem. Soc.*, 1972, 94, 6190, (3β,5α,25R)-3-(t-butyldimethylsilyloxy)spirostan-11,12-dione was desilylated with hydrofluoric acid in acetonitrile to give the title compound.

Preparation BB8

(3β,5α,11β,25R)-spirostan-3,11 -diol-12-one (3β,5α,11β, 12β,25R)-3-(t-butyldimethylsilyloxy)spirostan-11,12-diol: (3β,5α, 12β,25R)-3-(t-butyldimethylsilyloxy)spirostan-12-ol-11-one (see procedure G8) was converted into the title compound via reduction with lithium aluminum hydride in THF at room temperature according to the procedure described in *J. Am. Chem. Soc.,* 1951, 73, 1777.

(3β,5α,11β,12β,25R)-3-(t-butyldimethylsilyloxy)-12-acetoxyspirostan-11-ol: (3β,5α,11β,12β,25R)-3-(t-butyldimethylsilyloxy)spirostan-11,12-diol was selectively acetylated with acetic anhydride, pyridine and dimethylaminopyridine in methylene chloride to give the title compound.

(3β,5α,11β,12β,25R)-3-(t-butyldimethylsilyloxy)-11-(trimethylsilyloxy)-12-acetoxyspirostane: (3β,5α,11β,12β,25R)-3-(t-butyldimethylsilyloxy)-12-acetoxyspirostan-11-ol was silylated with trimethylsilyltriflate and 2,6-lutidine in methylene chloride according to the procedure described in *Tetrahedron Letters,* 1981, 22, 3455.

(3β,5α,11β,12β,25R)-3-(t-butyldimethylsilyloxy)-11-(trimethylsilyloxy)spirostan-12-ol: (3β,5α,11β,12β,25R)-3-(t-butyldimethylsilyloxy)-11 -(trimethylsilyloxy)-12-acetoxyspirostane was deacetylated by treatment with lithium aluminum hydride in THF followed by catious addition aqueous ammonium chloride. The resulting title compound suffered 11 to 12 silyl group migration on silica gel, and thus had to be used unpurified.

(3β,5α,11β,25R)-3-(t-butyldimethylsilyloxy-11-(trimethylsilyloxy)spirostan-12-one: (3β,5α,11β,12β,25R)-3-(t-butyldimethylsilyloxy)-11-(trimethylsilyloxy)spirostan-12-ol was oxidized with chromium trioxide and pyridine in methylene chloride according to the procedure described in *Org. Syn.,* 1976, 55, 84 to give the title compound.

(3β,5α11β,25R)-spirostan-3,11-diol-12-one: (3β,5α,11β,25R)-3-(t-butyldimethylsilyloxy)-11-(trimethylsilyloxy)spirostan-12-one was desilylated with hydrofluoric acid in acetonitrile according to the procedure describedin *J. Am. Chem. Soc.,* 1972, 94, 6190 to give the title compound. The title compound must be carefully handled because it will rearrange to (3β,5α,12β,25R)-spirostan-3,12-diol-11-one if exposed to base.

Preparation BB9

(3β,5α,11α,25R)spirostan-3,11 -diol-12-one (3β,5α,11α,12β,25R)3,11-di(acetoxy)spirostan-12-ol: (3β,5α,11α,12β,25R)-spirostan-3,11,12-triol (see preparation G6) was acetylated according to the procedure described in *J. Am. Chem. Soc.,* 1955, 77, 1632 to give a mixture of acetates from which the title compound could be isolated.

(3β,5α,11α,25R)3,11-di(acetoxy)spirostan-12-one: (3β,5α,11α,12β,25R)3,11-di(acetoxy)spirostan-12-ol was oxidized with chromium trioxide and pyridine in methylene chloride according to the procedure described in *Org. Syn.,* 1976, 55, 84 to give the title compound.

(3β,5α, 11α,25R)spirostan-3,11-diol-12-one: (3β,5α,11α,25R)-3,11-di(acetoxy)spirostan-12-one was saponified with sodium methoxide in methanol and THF to give the title compound.

Preparation BB10

(3β,5α,11α, 12α,25R)spirostan-3,11,12-triol (3β,5α,25R)spirostan-3-ol-12-tosylhydrazone: (3β,5α,25R)spirostan-3-ol-12-one (8.00 g) was dissolved in glacial acetic acid (200 mL) and warmed to 50° C. Paratoluenesulfonylhydrazide (6.928 g) was added and the solution was stirred at 50° C. for 30 min. After an additional 2 hours of stirring at room temperature, water (200 mL) was added. The resulting solid was collected, washed with water (100 mL), dried, triturated with refluxing acetone (300 mL), filtered hot and dried to give 3.903 g of the title compound.

(3β,5α,25R)spirost-11-en-3-ol: A mixture of (3β,5α,25R) spirostan-3-ol-12-tosylhydrazone (9.100 g) and sodium methoxide (8.379 g) in DMF (200 mL) was heated to 150° C. for 35 minutes, then cooled to room temperature. The mixture was then poured into ice water (1200 mL) and the resulting suspension filtered. The collected solid was washed with water (100 mL), air-dried, and dissolved in methylene chloride (700 mL). This solution was washed with water (2×200 mL), dried with MgSO4, and concentrated to give a white solid. Following flash chromatography, 2.384 g of the title compound (mp 179–181° C., lit. 188–192° C. —*J. Am. Chem. Soc.,* 1954, 76 4013) was isolated.

(3β,5α,11α,12α,25R)spirostan-3,11,12-triol: (3β,5α,25R)spirost-11 -en-3-ol was oxidized to the title compound with osmium tetroxide and N-methylmorpholine-N-oxide in water, t-butanol and acetone according to the procedure describe in *Tetrahedron Letters,* 1976, 1973.

Preparation BB11

(3β,5α, 12β,25R)spirostan-3,12-diol-11-one (3β,5α,11β,25R)-11-bromospirostan-3-ol-12-one: A glass lined reactor was charged with 50 gallons of methanol then subsurface sparged with hydrochloric acid gas until 7.7 Kg (5.0 eq) were charged. Upon completion of this sparge, the reactor was charged with 18.8 Kg (42.2 mole) of (3β,5α,25R) spirostan-3-ol-12-one, 50 gallons of methanol and 10 gallons of methylene chloride. This mixture was cooled to 10° C. and a solution of 8.4 Kg bromine (52.7 mole, 1.25 eq) in 10 gallons of methylene chloride was added over 2 hours while a pot temperature of approximately 10° C. was maintained. Once the addition was complete the reaction was allowed to warm to room temperature and was stirred for 2 hours. TLC at this point indicated complete reaction.

The reaction was diluted with 50 gallons of water and stirred for 10 minutes. After separation of layers, the aqueous layer was extracted twice with 30 gallons of methylene chloride. The three combined organic extracts were washed twice with 30 gallons of water, once with 30 gallons of saturated brine, then dried using 7.0 Kg of magnesium sulfate. The drying agent was removed by filtration on a 30 inch Lapp followed by two 3 gallon methylene chloride washes. The filtrate and washes were combined and atmospherically distilled to a 7 gallon total volume. Two 10 gallon methanol charges were made followed by continued distillation. When a final volume of <10 gallons had been reached the mixture was cooled to room temperature. The resulting suspension was granulated for 2 hours, filtered on a 30 inch Lapp, and the filter cake was washed twice with 3 gallons of methanol. Vacuum drying the filter cake at 45–50° C. yielded 12.6 Kg (58.6% yield) of the title compound.

(3β,5α,12β,25R)spirostan-3,12-diol-11-one: A glass lined reactor was charged with 12.4 Kg of (3β,5α,11β,25R)-11-bromospirostan-3-ol-12-one (24.34 mole), 33 gallons of t-butanol, 33 gallons of water and 7.5 Kg (189 mole, 7.75 eq) of sodium hydroxide pellets. The reaction was heated to reflux over 1.5 hours, maintained at -reflux for 4.5 hours (pot temperature was 83° C.), then cooled to room temperature. TLC at this point indicated complete reaction.

The reaction was distilled to remove the t-butanol. This was accomplished both by vacuum and atmospheric distillation. During the concentration two 32.5 gallon charges of water were added. Once the t-butanol had been removed, the aqueous suspension was cooled to room temperature and granulated for 2 hours. The suspension was filtered on a 30 inch Lapp, washed twice with 3 gallons of water, and the filter cake was air dried at 60° C. This afforded 11.1 Kg of the title compound.

Preparation BB12

(3β,5α,25R)spirostan-3-ol-11-one (3β,5α,12β,25R)-3,12-diacetoxyspirostan-11-one: A glass lined reactor was charged with 26 gallons of pyridine, 26 gallons of acetic anhydride and 11.0 Kg of (3β,5α,12β, 25R)spirostan-3,12-diol-11-one (preparation G12). This mixture was refluxed for 2 hours (pot temperature 128° C.) and allowed to cool to room temperature. The reaction was vacuum distilled to a total volume of 15 gallons (pot temperature approximately 45° C. during distillation). The suspension was diluted with 25 gallons of acetic acid and further vacuum distilled to a 15 gallon total volume (pot temperature at end approximately 80° C.). The mixture was diluted with 87 gallons of water and cooled to room temperature. After 5 hours of granulation, the title compound was isolated by filtration on a 30 inch Lapp followed by two 3 gallon water washes. The filter cake was dried at 60° C. under vacuum to yield 12.2 Kg (93.3%).

(3β,5α,25R)spirostan-3-ol-11-one: A stainless steel reactor was cooled to –80° C. by passing liquid nitrogen through internal coils. Ammonia was added to the reactor until 54.5 Kg (80 liters, 3,200 mole, 170 eq) had been charged.

At the same time that the ammonia charge was commencing, a glass lined reactor was charged with 10.0 Kg of (3β,5α,12β,25R)-3,12-diacetoxyspirostan-11-one 18.84 mole) and 40 gallons of THF. This solution was atmospherically distilled until a 26 gallon total volume had been reached.

At the completion of the ammonia charge, 2.8 Kg of calcium turnings (69.0 gram atoms, 3.7 eq) were added over 30 minutes while maintaining a pot temperature of –50° C. At the completion of this addition the THF solution of (3β,5α,12β,25R)-3,12-diacetoxyspirostan-11-one was added over 20 minutes (pot temperature at the end of the addition was –35° C.). followed by a 1.0 gallon THF rinse. The reaction mixture was stirred for 30 minutes at –35° C. to 40° C. While the reaction was at –35° C. to –40° C., 3.33 liters of bromobenzene (4.98 Kg, 31.7 mole, 1.68 eq) were added followed by 3.33 liters of water.

After this addition, the distillation of ammonia from the reactor was initiated. This distillation was directed to a water scrubber. Once all of the ammonia had been removed, the reaction (now at 24° C.) was transferred to a glass lined reactor followed by a 4 gallon THF rinse. The solution and rinse combined were vacuum distilled to a thick oil. To this was added 35 gallons of methanol and 3.3 Kg (59 mole) of potassium hydroxide pellets. This mixture was heated at reflux for 1 hour, cooled, then 10 liters of acetic acid and 44 gallons of water were charged. This suspension was further cooled to room temperature and granulated for 1 hour. The title compound was isolated by filtration on a 30 inch Lapp followed by a 5 gallon 3:1 water/methanol wash. Vacuum drying at 55° C. yielded 7.05 Kg (86.9%).

Preparation BB: Physical Data

Satisfactory MS and IR data was obtained on all of the (3β,5α,25R)spirostan-3-ols described in the above BB preparations (see table 2). The various diol and triol products could be distinguished by proton NMR (see table 3)

TABLE 2

Diagnostic Mass Spectrometry and infrared Data
LSMIS IR

| compound | molecular formula | parent ion (m/z) | diagnostic resonances (cm-1 intensity, solvent) |
|---|---|---|---|
| 11α-ol | $C_{27}H_{44}O_4$ | 433 | 3575 (m), 3440 (m) (CHCl$_3$) |
| 11β-ol | $C_{27}H_{44}O_4$ | 433 | 3560 (m), 3425 (m) (CHCl$_3$) |
| 12α-ol | $C_{27}H_{44}O_4$ | 433 | 3590 (m), 3420 (m) (CHCl$_3$) |
| 12β-ol | $C_{27}H_{44}O_4$ | 433 | — |
| 11α,12α-diol | $C_{27}H_{44}O_5$ | 449 | 3424 (m) (KBr) |
| 11α,12β-diol | $C_{27}H_{44}O_5$ | 449 | 3550 (m), 3450 (m) (CHCl$_3$) |
| 11β,12α-diol | $C_{27}H_{44}O_5$ | 449 | 3441 (m) (KBr) |
| 11β,12β-diol | $C_{27}H_{44}O_5$ | 449 | 3600 (m), 3450 (m) (CHCl$_3$) |
| 11α-ol-12-one | $C_{27}H_{42}O_5$ | 447 | 3515 (m), 1705 (s) (KBr) |
| 11β-ol-12-one | $C_{27}H_{42}O_5$ | 447 | 3450 (m), 1712(s) (KBr) |
| 12α-ol-11-one | $C_{27}H_{42}O_5$ | 447 | 3410 (m), 1 706 (s) (KBr) |
| 12β-ol-11-one | $C_{27}H_{42}O_5$ | 447 | 3475 (m), 1708 (s) (CHCl$_3$) |
| 11,12-dione | $C_{27}H_{40}O_5$ | 445 | 3600 (w), 3400 (m), 1710 (w) 1670 (s), 1605 (m) (CHCl$_3$)[1] |
| 11-one | $C_{27}H_{42}O_4$ | 431 | 3600 (w), 3450 (m), 1705 (s) (CHCl$_3$) |

[1]IR data suggest that this compound readily tautomerizes enol ketone form in CHCl$_3$.

TABLE 3

Diagnostic Proton Nuclear Magnetic Resonance Data[2]

| compound | peaks >2 ppm |
|---|---|
| 11α-ol | 3.90 (ddd, 6,6 & 4 Hz, 1H), 2.26 (dt, 13 & 4, 1H) |
| 11β-ol | 4.22 (brs, 1 H) |
| 12α-ol | 3.67 (s, 1 H), 2.37 (dd, 8 & 7 Hz, 1H) |
| 12β-ol | 3.26 (dd, 10 & 4 Hz, 1H) |

TABLE 3-continued

Diagnostic Proton Nuclear Magnetic Resonance Data[2]

| compound | peaks >2 ppm |
| --- | --- |
| 11α,12α-diol | 3.91(m, 1H), 3.56 (d, 3H, 1H), 2.45 (dd, 9 & 7 Hz, 1H) |
| 11α,12β-diol | 3.55(m, 1H), 3.03 (d, 8H, 1H), 2.21 (dt,12 & 4 Hz, 1H) |
| 11β,12α-diol | 4.12 (br s, 1H), 3.55 (d, 2 Hz, 1H), 2.36 (dd, 9 & 7 Hz, 1H) |
| 11β,12β-diol | 4.07 (br s, 1H), 3.13 (d, 3 Hz, 1H) |
| 11α-ol-12-one | 3.72 (m, 1H), 2.39 (dt, 13 & 4 Hz, 1H) |
| 11β-ol-12-one | 3.96 (m, 1H), 2.2 (m, 1H) |
| 12α-ol-11-one | 3.51 (s, 1H), 2.57 (dd, 8 & 7 Hz, 1H), 2.2 (complex, 7H) |
| 12β-ol-11-one | 3.78 (s, 1H), 2.39 (dt,13 & 4 Hz, 1H), 2.1 (m, 2H) |

[2]All samples run in $CDCl_3$ except 11β-ol-12-one which was run in DMSO-$d_6$. Peaks for $H_{16}$, $H_3$, $H_{26eq}$ and $H_{26ax}$ are also observed at >2 ppm. In $CDCl_3$, these are observed at 4.37 (ddd, J = 9, 9 & 7 Hz, 1H), 3.56 (heptet, J = 4 Hz, 1H), 3.45 (ddd, J = 10, 6 & 2 Hz, 1H), 3.35 (t, J = 11 Hz, 1H).

Preparation CC1

5-Methyl-2-thienyl-methylamine

Methoxylamine hydochloride (3.5 g, 41.7 mmol) and pyridine (6.75 mL, 83.5 mmol) was added to a solution of 5-methylthiophene-2-carboxaldehyde (3.5 g, 27.8 mmol) in methanol (20 mL) at room temperature. After 3 h, the mixture was concentrated in vacuo, diluted with ethyl acetate (100 mL) and washed with 1 N HCl (3×) and brine (1×), dried ($Na_2SO_4$), filtered and concentrated in vacuo to give a mixture of oxime isomers.

Trifluoroacetic acid (4.97 mL, 65 mmol) was added dropwise to a suspension of sodium borohydride (2.44 g, 65 mmol) in THF (40 mL) at 0° C. A solution of the oxime prepared above (2.0 g, 13 mmol) in THF (5 mL) was then added dropwise. After 2 h, the reaction was heated to a gentle reflux for 2 h, cooled, and quenched by the addition of water (10 mL). The mixture was diluted with methylene chloride (50 mL) and washed with brine (2×) and dried ($MgSO_4$) filtered and concentrated in vacuo. The residue was dissolved in 100 mL of diethyl ether and treated with sat HCl in ether (3 mL). The precipitate was collected by vacuum filtration and washed with ether and dried to afford the titled amine as a white solid as its hydrochloride salt (1.2 g). $^1$H NMR (250 MHz, d6 DMSO) δ 8.5 (bs, 3H); 7.0 (d, 1H, J=2.0 Hz); 6.7 (m, 1H); 4.1 (bs, 2H); 2.4 (s, 3H).

In an analogous manner, the following compounds, Preparation CC2-CC3 were prepared from the appropriate starting material using the above general procedure.

Preparation CC2

5-Bromo-2-thienyl-methylamine

Preparation CC3

4-Bromothienyl-methylamine

Preparation DD 3-thienyl-methylamine hydrochloride

3-Thiophenecarbonitrile (2.0 g, 18.3 mmol) was added dropwise as a solution in THF (20 mL) to a suspension of lithium aluminum hydride (695 mg, 18.3 mmol) in THF (20 mL) at 0° C. After 1 h at room temperature, the reaction was quenched by the sequential addition of $H_2O$ (700 μL), 15% NaOH (700 μL) and $H_2O$ (2.1 mL). The mixture was diluted with ether (50 mL) and dried ($MgSO_4$) filtered and concentrated in vacuo. The residue was dissolved in ether (50 mL) and treated with sat HCl/ether (3 mL). The resulting precipitate was filtered and washed with ether and dried to afford the title compound as an off-white solid. $^1$H NMR (250 MHz, d6 DMSO) δ 8.5 (bs, 3H); 7.65 (bs, 1H); 7.52 (dd, 1H, J=6.0, 2.0 Hz); 7.3 (dd, 1H, J=6.0 Hz); 4.0 (d, 2H, J=6.0 Hz).

Preparation EE

α-(2-thienyl)-2-yl-α-trimethylsiloxy-acetonitrile

Cyanohydrin Formation

Zinc iodide (5 mg) was added to a solution of trimethylsilyl cyanide (3.27 mL, 0.025 mol) and 2-thiophenecarboxaldehyde (2.08 mL, 0.022 mol) in dichloromethane (50 mL) at room temperature. After 24 h, the mixture was concentrated and used without purification. $^1$H NMR (250 MHz, $CDCl_3$) δ 7.35(dd, 1H, J=5.0, 1.0 Hz); 7.2 (dd, 1H, J=4.0 1.0 Hz); 7.0 (dd, 1H, J=5.0, 4.0 Hz); 5.2 (s, 1H); 0.2 (s, 9H).

Preparation FF1

2-amino-1 -(2-thienyl)-ethanol

Nitrile Reduction

A solution of α-(2-thienyl)-α-trimethylsiloxy-acetonitrile (4.77 g, 0.024 mol) in THF (10 mL) was added dropwise to a suspension of lithium aluminum hydride (1.0 g, 0.027 mol) in THF (20 mL) at 0C. After 1.5 h at room temperature, the reaction was quenched by the sequential addition of $H_2O$ (1mL), 15% NaOH (1mL) and $H_2O$ (3 mL). The mixture was diluted with ether (50 mL), dried ($MgSO_4$) filtered and concentrated to give 2.7 g product as an oil. $^1$H NMR (250 MHz, $CDCl_3$) 6 7.2 (m, 1H); 7.0 (m, 2H); 4.9 (m, 1H); 3.0 (ddd, 1H, J 15.0, 12.0, 5.0 Hz); 2.9 (ddd, 1H, J=12.0, 5.0, 2.0 Hz); 2.0 (bs, 2H).

Preparation GG1

Thiazol-2-yl-methylamine

Azide Reduction

Triphenylphosphine (2.08 g, 7.9 mmol) was added to a solution of 2-azidomethyl-thiazole (1.11 g, 7.9 mmol) in THF (20 mL). After 1 h, $H_2O$ (214 μL) and ammonium hydroxide sol (0.5 mL) were added sequentially. The reaction stirred overnight, was concentrated in vacuo, and purified by flash chromatography (5% methanol/methylene chloride) to afford 645 mg of the title product as a tan oil (72%). $^1$H NMR (250 MHz, $CDCl_3$) 6 7.7 (d, 1H, J=2.0 Hz); 7.25 (d, 1H, J=2.0 Hz); 4.2 (s, 2H); 1.7 (bs, 2H).

In an analogous manner, the following compound, Preparation GG2 was prepared from the appropriate starting material using the above general procedure.

Preparation GG2

3-Methyllsoxazol-5-yl-methylamine

Preparation HH1

2-azidomethyl-thiazole

Diphenylphosphoryl azide (3.25 mL, 0.015 mol) and 1,8-diazabicyclo[5.4.0]undec-7-ene (2.25 mL, 0.025 mol)

were added to a solution of thiazol-2-yl-methanol (1.44 g, 0.013 mol) in toluene (20 mL) at 0° C. After 1 h the reaction was warmed to room temperature and stirred overnight. The mixture was diluted with toluene (20 mL) and washed with H$_2$O (3×) brine (1×), dried (Na$_2$SO$_4$), filtered and concentrated in vacuo. The residue was purified by flash chromatography (30% ethyl acetate/hexanes) to afford the azide as a tan oil (1.1 g, 63%). IR 2098 cm. $^1$H NMR (250 MHz, CDCl$_3$) δ 7.8 (d, 1H, J=2.0 Hz); 7.4 (d, 1H, J=2.0 Hz); 4.7 (s, 2H).

In an analogous manner, the following compound, Preparation HH2 was prepared from the appropriate starting material using the above general procedure.

Preparation HH2

5-azidomethyl-3methylisoxazole

Preparation II 1

3-amino-2,2-dimethyl-propionic acid methyl ester

Raney nickel (2 g) was washed with water then methanol and added to a solution of methyl 2,2-dimethyl cycano acetate (2.0 g, 0.016 mol) in methanol (75 mL). The mixture was shaken under 40 psi of hydrogen in a Parr aparatus. After 3 h, the reaction was purged with nitrogen. The catalyst was removed by filtration and the filtrate was acidified by the addition of sat HCl/ether (5 mL). The solution was concentrated to approx. 5 mL and added to 200 mL of vigorously stirred ether. The resulting solid was collected by vacuum filtration, washed with ether and dried to afford 1.25 g of amine hydrochloride as a white solid. m.p. 168–170° C. $^1$H NMR (250 MHz, CDCl$_3$) δ 8.3 (bs, 3H); 3.6 (s, 3H); 2.92 (m, 2H); 1.2 (s, 6H).

In an analogous manner, the following compound, Preparation 112 was prepared from the appropriate starting material using the above general procedure.

Preparation 112

2-aminomethyl-butyricacid methyl ester

Preparation JJ 2-thienyl isocyanate

Sodium azide (2.5 g, 0.039 mol) as a solution in H$_2$O (10 mL) was added dropwise to a solution of 2-thiophenecarbonyl chloride (5.7 g, 0.039 mol) in toluene (80 mL) at 0° C. After 30 min the layers were separated and the aqueous layer extracted with ether. The combined organic layers were dried (MgSO$_4$), filtered and the ether was removed in vacuo. The solution of 2-thiophenecarbonyl azide was heated at 85° C. for 3 h producing a solution of 2-thienyl-isocyanate which was used as is.

I claim:

1. A spirostanyl glycoside compound of Formula I

Formula I

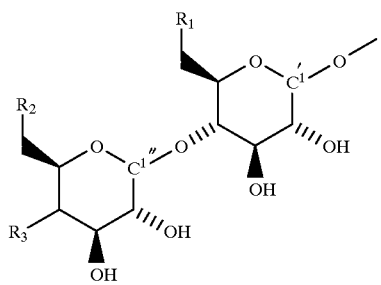

-continued

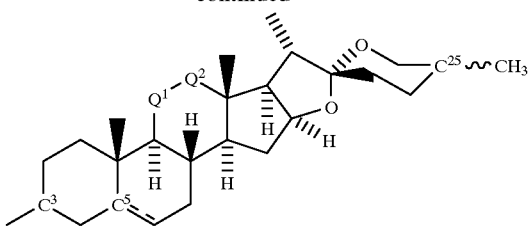

and the pharmaceutically-acceptable salts and hydrates thereof
wherein
Q$^1$ is carbonyl,

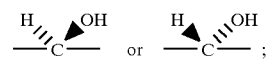

Q$^2$ is methylene, carbonyl,

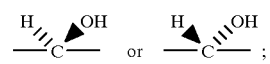

R$_1$, R$_2$, and R$_3$ are each hydroxy or —Z—R$_4$;
Z for each occurrence is independently —NH—C(=O)—, —O—C(=O)—N(R$_5$)—, —NH—C(=O)—N(R$^5$)— or —O—C(=S)—N(R$^5$)—;
R$_4$ for each occurrence is independently aryl, aryl(C$_1$–C$_6$)alkyl, (C$_2$–C$_4$)alkenyl, (C$_1$–C$_6$)alkyl, cyclo(C$_3$–C$_7$)alkyl or cyclo(C$_3$–C$_7$)alkyl(C$_1$–C$_6$)alkyl; each R$_4$ optionally mono-, di-, or tri-substituted independently with halo, (C$_1$–C$_4$)alkyl, hydroxy, phenoxy, trifluoromethyl, nitro, (C$_1$–C$_4$)alkoxy, methylenedioxy, oxo, (C$_1$–C$_4$)alkylsulfanyl, (C$_1$–C$_4$)alkylsulfinyl, (C$_1$–C$_4$)alkylsulfonyl, dimethylamino, mono-or di-(C$_1$–C$_4$)alkylaminocarbonyl, (C$_1$–C$_4$)alkylcarbonyl, (C$_1$–C$_4$)alkoxycarbonyl, pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and
R$_5$ for each occurrence is independently hydrogen, (C$_1$–C$_4$)alkyl or R$_5$ is such that when taken together with the nitrogen to which it is attached and with R$_4$, wherein R$_4$ is a covalent bond, it forms pyrrolidinyl, piperidinyl, N-methylpiperazinyl, indolinyl or morpholinyl and such cyclic group may be substituted on carbon with (C$_1$–C$_4$)alkoxycarbonyl;
with the proviso that R$_1$, R$_2$ and R$_3$ are not all hydroxy.

2. A compound according to claim 1 wherein R$_1$, R$_2$ and R$_3$ are each independently hydroxy or —Z—R$_4$, Z is —O—C(=O)—N(R$_5$)— and R$_5$ is hydrogen.

3. A compound according to claim 2 wherein the C$^{1'''}$ anomeric oxy is beta, the C$^{1'}$ anomeric oxy is beta, R$_3$ is alpha, the C$^5$ hydrogen is alpha, C$^{25}$ is (R), the C$^3$ oxy is beta, Q$^1$ is carbonyl, Q$^2$ is methylene and R$_1$ is hydroxy.

4. A compound according to claim 3 wherein R$_3$ is hydroxy, R$_2$ is —Z—R$_4$ and R$_4$ is 2,4-difluorophenyl.

5. A compound according to claim 3 where R$_2$ and R$_3$ are —Z—R$_4$ and R$_4$ is 2-fluorophenyl.

6. A compound according to claim 3 where R$_2$ and R$_3$ are —Z—R$_4$ and R$_4$ is 2,4-difluorophenyl.

7. A compound according to claim 3 wherein R$_2$ and R$_3$ are —Z—R$_4$ and R$_4$ is 2-methylphenyl.

8. A compound according to claim 3 where $R_2$ and $R_3$ are —Z—$R_4$ and $R_4$ is phenyl.

9. A compound according to claim 3 wherein $R_2$ is —Z—$R_4$, $R_4$ is 2,6-dichlorophenyl and $R_3$ is hydroxy.

10. A compound according to claim 3 wherein $R_2$ is —Z—$R_4$, $R_4$ is 2-fluorophenyl and $R_3$ is hydroxy.

11. A compound according to claim 3 wherein $R_2$ and $R_3$ are Z—$R_4$ and $R_4$ is 2-thienyl-methyl.

12. A compound according to claim 3 wherein $R_2$ and $R_3$ are Z—$R_4$ and $R_4$ is 2-methoxycarbonyl-ethyl.

13. A compound according to claim 3 wherein $R_2$ and $R_3$ are Z—$R_4$ and $R_4$ is thiazol-2-yl-methyl.

14. A compound according to claim 3 wherein $R_2$ and $R_3$ are Z—$R_4$ and $R_4$ is 2-methoxycarbonyl-butyl.

15. A compound according to claim 2 wherein the $C^1$ anomeric oxy is beta, the $C^1$ anomeric oxy is beta, $R_3$ is alpha, the $C^5$ hydrogen is alpha, $C^{25}$ is (R), the $C^3$ oxy is beta, $Q^1$ is carbonyl, $Q^2$ is

and $R_1$ is hydroxy.

16. A compound according to claim 15 wherein $R_2$ and $R_3$ are Z—$R_4$, and $R_4$ is 2-fluorophenyl.

17. A compound according to claim 15 wherein $R_2$ and $R_3$ are Z—$R_4$ and $R_4$ is 2-thienyl-methyl.

18. A compound according to claim 15 wherein $R_2$ and $R_3$ are Z—$R_4$ and $R_4$ is 2-methoxycarbonyl-ethyl.

19. A compound according to claim 15 wherein $R_2$ and $R_3$ are Z—$R_4$ and $R_4$ is thiazol-2-yl-methyl.

20. A method of treating hypercholesterolemia which comprises administering to a mammal in need of such treatment a therapeutically effective amount of a compound of claim 1.

21. A pharmaceutical composition for the treatment of hypercholesterolemia in a mammal which comprises a therapeutically effective amount of compound of claim 1 and a pharmaceutically acceptable carrier.

22. A method of treating atherosclerosis which comprises administering to a mammal in need of such treatment a therapeutically effective amount of a compound of claim 1.

23. A pharmaceutical composition for the treatment of atherosclerosis in a mammal which comprises a therapeutically effective amount of compound of claim 1 and a pharmaceutically acceptable carrier.

* * * * *